US 7,645,570 B2

(12) United States Patent
Fernandez-Salas et al.

(10) Patent No.: US 7,645,570 B2
(45) Date of Patent: Jan. 12, 2010

(54) BOTULINUM TOXIN SCREENING ASSAYS

(75) Inventors: Ester Fernandez-Salas, Fullerton, CA (US); Patton E. Garay, Long Beach, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 12/047,441

(22) Filed: Mar. 13, 2008

(65) Prior Publication Data

US 2008/0182799 A1 Jul. 31, 2008

Related U.S. Application Data

(63) Continuation-in-part of application No. 10/598,073, filed as application No. PCT/US2005/006421 on Feb. 23, 2005.

(60) Provisional application No. 60/547,591, filed on Feb. 24, 2004.

(51) Int. Cl.
*A61K 39/02* (2006.01)
*A61P 31/00* (2006.01)
*C12Q 1/02* (2006.01)

(52) U.S. Cl. .............................. 435/4; 435/23; 435/69.1
(58) Field of Classification Search ........................ None
See application file for complete search history.

(56) References Cited

U.S. PATENT DOCUMENTS

| 5,731,161 | A | 3/1998 | Aoki et al. |
| 5,750,365 | A | 5/1998 | Chiu et al. |
| 5,925,528 | A | 7/1999 | Chiu et al. |
| 5,962,637 | A | 10/1999 | Shone et al. |
| 7,465,549 | B2 * | 12/2008 | Lynch et al. ................. 435/7.1 |
| 2001/0008759 | A1 | 7/2001 | Marks et al. |
| 2004/0014024 | A1 | 1/2004 | Yayon et al. |
| 2004/0072270 | A1 * | 4/2004 | Fernandez-Salas et al. . 435/7.32 |
| 2004/0106147 | A1 * | 6/2004 | Lynch et al. ................. 435/7.1 |
| 2004/0170651 | A1 * | 9/2004 | Roux et al. ............. 424/239.1 |
| 2005/0060761 | A1 * | 3/2005 | Vazquez-Martinez et al. .. 800/3 |
| 2005/0288247 | A1 * | 12/2005 | Svoboda et al. ............... 514/44 |
| 2006/0153876 | A1 * | 7/2006 | Sanders ................... 424/239.1 |
| 2008/0003240 | A1 * | 1/2008 | Fernandez-Salas et al. ............................... 424/ |
| 2008/0081832 | A1 * | 4/2008 | Kenda et al. ................. 514/394 |
| 2008/0182799 | A1 * | 7/2008 | Fernandez-Salas et al. .... 514/23 |
| 2008/0279896 | A1 * | 11/2008 | Heinen et al. ... 424/239.1 236.1 |

FOREIGN PATENT DOCUMENTS

| WO | WO 02/102854 | 12/2002 |
| WO | WO 02/102972 | 12/2002 |
| WO | WO 02/102973 | 12/2002 |
| WO | WO 2004/110487 | 12/2004 |
| WO | 2005/082096 | * 9/2005 |

OTHER PUBLICATIONS

Dong, M et al, Science Apr. 28, 2006, vol. 12, pp. 592-596, SV2 is the protein receptor for Botulinum Neurotoxin A.*

(Continued)

*Primary Examiner*—Robert B Mondesi
*Assistant Examiner*—Ginny Portner
(74) *Attorney, Agent, or Firm*—Dean G. Stathakis; Joel B. German; Debra D. Condino

(57) ABSTRACT

Methods for detecting BoNT/A activity in a sample, methods for screening molecules able to compete with BoNT/A receptor binding, methods for reducing BoNT/A activity in a human and methods of marketing a neurotoxin capable of selectively binding to FGFR3 to a governmental or regional regulatory authority.

20 Claims, 13 Drawing Sheets

OTHER PUBLICATIONS

Keller, James E. et al, FEBS Letters, vol. 456, 1999, pp. 137-142, Persistence of botulinum neurotoxin actin in cultured spinal cord cells.*

L-M. Sturla et al., FGFR3IIIS: a novel soluble FGFR3 spliced variant that modulates growth is frequently expressed in tumour cells, 89(7) Br. J. Cancer 1276-1284 (2003).

M. Kanai et al., Signal transduction pathway of human fibroblast growth factor receptor 3. Identification of a novel 66-kDa phosphoprotein, 272(10) J. Biol. Chem. 6621-6628 (1997).

Janet E. Henderson et al., Expression of FGFR3 with the G380R achondroplasia mutation inhibits proliferation and maturation of CFK2 chondrocytic cells, 15(1) J. Bone Miner. Res. 155-165 (2000).

Noriko Yokosawa et al., Binding of Clostridium botulinum type C neurotoxin to different neuroblastoma cell lines, 57(1) Infect. Immun. 272-277 (1989).

Noriko Yokosawa et al., Binding of botulinum type C1, D and E neurotoxins to neuronal cell lines and synaptosomes, 29(2) Toxicon 261-264 (1991).

Tei-ichi Nishiki et al., Identification of protein receptor for Clostridium botulinum type B neurotoxin in rat brain synaptosomes, 269(14) J. Biol. Chem. 10498-10503 (1994).

Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999).

Elizabeth E. Plowright et al., Ectopic expression of fibroblast growth factor receptor 3 promotes myeloma cell proliferation and prevents apoptosis, 95(3) Blood 992-998 (2000).

Yukako Fujinaga et al., Molecular characterization of binding subcomponents of Clostridium botulinum type C progenitor toxin for intestinal epithelial cells and erythrocytes, 150(Pt 5) Microbiology 1529-1538 (2004).

Atsushi Nishikawa et al., The receptor and transporter for internalization of Clostridium botulinum type C progenitor toxin into HT-29 cells, 319(2) Biochem. Biophys. Res. Commun. 327-333 (2004).

Erik A. Mijan and Eric G. Bremer, Regulation of Growth Factor Receptors by Gangliosides, 2002(160)Sci. STKE.RE15(2002).

Akio Shimizu et al, A novel alternatively spliced fibroblast growth factor receptor 3 isoform lacking the acid box domain is expressed during chondrogenic differentiation of ATDC5 cells, 276(14) J. Biol. Chem. 11031-11040 (2001).

C. J. Powers et al., Fibroblast growth factors, their receptors and signaling 7(3)Endocr. Relat. Cancer. 165-197 (2000).

Bernhard Reuss & Oliver von Bohlen und Halbach, Fibroblast growth factors and their receptors in the central nervous system, 313(2) Cell Tissue Res. 139-157 (2003).

Office Action Date Mailed Jun. 20, 2008, in U.S. Appl. No. 10/598,073.

Keller, James E. et al, FEBS Letters, vol. 456, 1999, pp. 137-142, Persistence of botulinum neurotoxin action in cultured spinal cord cells.

* cited by examiner

SNAP-25₁₉₇ ▶

Neuro-2A

Neuro-2A

FIG. 10a.

Control | BoNT/A-SBED Treated

◄ 250 kDa Complex

FIG. 10b.

| Cell Lyaste | Immunoprecipitated Samples |

Control | BoNT/A-SBED Treated | Control | BoNT/A-SBED Treated | Control | BoNT/A-SBED Treated ◄ BoNT/A 150 kDa
◄ BoNT/A 100 kDa

FGFR3 ►

```
                              SEQUENCE LISTING

<160> NUMBER OF SEQ ID NOS: 36

<210> SEQ ID NO 1
<211> LENGTH: 2427
<212> TYPE: DNA
<213> ORGANISM: Homo sapiens FGFR3IIIb

<400> SEQUENCE: 1
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg gggatgctgt ggagctgagc     180 tgtccccgc ccggggggtgg tcccatgggg cccactgtct gggtcaagga tggcacaggg     240
ctggtgccct cggagcgtgt cctggtgggg ccccagcggc tgcaggtgct gaatgcctcc     300
cacgaggact ccgggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct ccgctgccc agccgctggc     540 aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag tcctggatca gtgagagtgt ggaggccgac     960
gtgcgcctcc gcctggccaa tgtgtcggag cgggacgggg gcgagtacct ctgtcgagcc    1020
accaatttca taggcgtggc cgagaaggcc ttttggctga cgcttcacgg gccccgagca    1080
gccgaggagg agctggtgga ggctgacgag gcgggcagtg tgtatgcagg catcctcagc    1140 tacgggtgg gcttcttcct gttcatcctg gtggtggcg ctgtgacgct ctgccgcctg    1200
cgcagccccc ccaagaaagg cctgggctcc cccaccgtgc acaagatctc ccgcttcccg    1260
ctcaagcgac aggtgtccct ggagtccaac gcgtccatga gctccaacac accactggtg    1320
cgcatcgcaa ggctgtcctc agggagggc cccacgctgg ccaatgtctc cgagctcgag    1380
ctgcctgccg accccaaatg ggagctgtct cgggccggc tgacccctggg caagcccctt    1440 ggggagggct gcttcggcca ggtggtcatg gcggaggcca tcggcattga caaggaccgg    1500
```

-continued

```
gccgccaagc ctgtcaccgt agccgtgaag atgctgaaag acgatgccac tgacaaggac    1560
ctgtcggacc tggtgtctga gatggagatg atgaagatga tcgggaaaca caaaaacatc    1620
atcaacctgc tgggcgcctg cacgcagggc gggcccctgt acgtgctggt ggagtacgcg    1680
gccaagggta acctgcggga gtttctgcgg gcgcggcggc cccgggcct  ggactactcc    1740 ttcgacacct gcaagccgcc cgaggagcag ctcaccttca aggacctggt gtcctgtgcc    1800
taccaggtgg cccggggcat ggagtacttg gcctcccaga agtgcatcca cagggacctg    1860
gctgcccgca atgtgctggt gaccgaggac aacgtgatga agatcgcaga cttcgggctg    1920
gcccgggacg tgcacaacct cgactactac aagaagacaa ccaacggccg gctgcccgtg    1980
aagtggatgg cgcctgaggc cttgtttgac cgagtctaca ctcaccagag tgacgtctgg    2040
tcctttgggg tcctgctctg ggagatcttc acgctggggg ctccccgta  ccccggcatc    2100 cctgtggagg agctcttcaa gctgctgaag gagggccacc gcatggacaa gcccgccaac    2160
tgcacacacg acctgtacat gatcatgcgg gagtgctggc atgccgcgcc ctcccagagg    2220
cccaccttca gcagctggt  ggaggacctg gaccgtgtcc ttaccgtgac gtccaccgac    2280
gagtacctgg acctgtcggc gccttttcgag cagtactccc cgggtggcca ggacaccccc    2340
agctccagct cctcagggga cgactccgtg tttgcccacg acctgctgcc cccggcccca    2400
cccagcagtg ggggctcgcg gacgtga                                         2427
```

<210> SEQ ID NO 2
<211> LENGTH: 808
<212> TYPE: PRT
<213> ORGANISM: Homo sapiens FGFR3IIIb

<400> SEQUENCE: 2

```
Met Gly Ala Pro Ala Cys Ala Leu Ala Leu Cys Val Ala Val Ala Ile
  1               5                  10                  15

Val Ala Gly Ala Ser Ser Glu Ser Leu Gly Thr Glu Gln Arg Val Val
             20                  25                  30

Gly Arg Ala Ala Glu Val Pro Gly Pro Glu Pro Gly Gln Gln Glu Gln
         35                  40                  45

Leu Val Phe Gly Ser Gly Asp Ala Val Glu Leu Ser Cys Pro Pro Pro
     50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                 85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205
```

```
Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
```

```
                625                 630                 635                 640
Ala Arg Asp Val His Asn Leu Asp Tyr Tyr Lys Lys Thr Thr Asn Gly
                    645                 650                 655

Arg Leu Pro Val Lys Trp Met Ala Pro Glu Ala Leu Phe Asp Arg Val
                660                 665                 670

Tyr Thr His Gln Ser Asp Val Trp Ser Phe Gly Val Leu Leu Trp Glu
            675                 680                 685

Ile Phe Thr Leu Gly Gly Ser Pro Tyr Pro Gly Ile Pro Val Glu Glu
            690                 695                 700

Leu Phe Lys Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                    725                 730                 735

Pro Ser Gln Arg Pro Thr Phe Lys Gln Leu Val Glu Asp Leu Asp Arg
                740                 745                 750

Val Leu Thr Val Thr Ser Thr Asp Glu Tyr Leu Asp Leu Ser Ala Pro
                755                 760                 765

Phe Glu Gln Tyr Ser Pro Gly Gly Gln Asp Thr Pro Ser Ser Ser Ser
            770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 3
<211> LENGTH: 2421
<212> TYPE: DNA
<213> ORGANISM: Homo sapiens FGFR3IIIc

<400> SEQUENCE: 3
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg gccagcagga gcagttggtc ttcggcagcg ggatgctgtg gagctgagc     180 tgtcccccgc ccgggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt ttggcagcat ccggcagacg     720
tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag acggcgggcg ctaacaccac cgacaaggag     960
ctagaggttc tctccttgca aacgtcacc tttgaggacg ccggggagta cacctgcctg    1020
gcgggcaatt ctattgggtt ttctcatcac tctgcgtggc tggtggtgct gccagccgag    1080
```

-continued

```
gaggagctgg tggaggctga cgaggcgggc agtgtgtatg caggcatcct cagctacggg    1140
gtgggcttct tcctgttcat cctggtggtg gcggctgtga cgctctgccg cctgcgcagc    1200
ccccccaaga aaggcctggg ctcccccacc gtgcacaaga tctcccgctt cccgctcaag    1260
cgacaggtgt ccctggagtc caacgcgtcc atgagctcca cacaccact ggtgcgcatc     1320
gcaaggctgt cctcagggga gggccccacg ctggccaatg tctccgagct cgagctgcct    1380
gccgaccca aatgggagct gtctcgggcc cggctgaccc tgggcaagcc ccttggggag     1440
ggctgcttcg gccaggtggt catggcggag ccatcggca ttgacaagga ccgggccgcc     1500
aagcctgtca ccgtagccgt gaagatgctg aaagacgatg ccactgacaa ggacctgtcg    1560
gacctggtgt ctgagatgga gatgatgaag atgatcggga acacaaaaa catcatcaac    1620
ctgctgggcg cctgcacgca gggcgggccc ctgtacgtgc tggtggagta cgcggccaag    1680
ggtaacctgc gggagtttct gcgggcgcgg cggccccgg gcctggacta ctccttcgac     1740
acctgcaagc cgcccgagga gcagctcacc ttcaaggacc tggtgtcctg tgcctaccag    1800
gtggcccggg gcatggagta cttggcctcc cagaagtgca tccacaggga cctggctgcc    1860
cgcaatgtgc tggtgaccga ggacaacgtg atgaagatcg cagacttcgg gctggcccgg    1920
gacgtgcaca acctcgacta ctacaagaag acaaccaacg gccggctgcc cgtgaagtgg    1980
atggcgcctg aggccttgtt tgaccgagtc tacactcacc agagtgacgt ctggtccttt    2040
ggggtcctgc tctgggagat cttcacgctg gggggctccc cgtaccccgg catccctgtg    2100
gaggagctct tcaagctgct gaaggagggc accgcatgg acaagcccgc caactgcaca     2160
cacgacctgt acatgatcat gcgggagtgc tggcatgccg cgcctccca gaggcccacc     2220
ttcaagcagc tggtggagga cctggaccgt gtccttaccg tgacgtccac cgacgagtac    2280
ctggacctgt cggcgccttt cgagcagtac tccccgggtg gccaggacac ccccagctcc    2340
agctcctcag gggacgactc cgtgtttgcc cacgacctgc tgcccccggc cccacccagc    2400
agtgggggct cgcggacgtg a                                              2421
```

<210> SEQ ID NO 4
<211> LENGTH: 806
<212> TYPE: PRT
<213> ORGANISM: Homo sapiens FGFR3IIIc

<400> SEQUENCE: 4

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
```

-continued

```
            130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                    165                 170                 175
Pro Ala Ala Gly Asn Pro Thr Pro Ser Ile Ser Trp Leu Lys Asn Gly
                180                 185                 190
Arg Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                    245                 250                 255
Ala Gly Leu Pro Ala Asn Gln Thr Ala Val Leu Gly Ser Asp Val Glu
                260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                    325                 330                 335
Tyr Thr Cys Leu Ala Gly Asn Ser Ile Gly Phe Ser His His Ser Ala
                340                 345                 350
Trp Leu Val Val Leu Pro Ala Glu Glu Leu Val Glu Ala Asp Glu
            355                 360                 365
Ala Gly Ser Val Tyr Ala Gly Ile Leu Ser Tyr Gly Val Gly Phe Phe
370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                    405                 410                 415
Phe Pro Leu Lys Arg Gln Val Ser Leu Glu Ser Asn Ala Ser Met Ser
                420                 425                 430
Ser Asn Thr Pro Leu Val Arg Ile Ala Arg Leu Ser Ser Gly Glu Gly
            435                 440                 445
Pro Thr Leu Ala Asn Val Ser Glu Leu Glu Leu Pro Ala Asp Pro Lys
450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                    485                 490                 495
Asp Arg Ala Ala Lys Pro Val Thr Val Ala Val Lys Met Leu Lys Asp
                500                 505                 510
Asp Ala Thr Asp Lys Asp Leu Ser Asp Leu Val Ser Glu Met Glu Met
            515                 520                 525
Met Lys Met Ile Gly Lys His Lys Asn Ile Ile Asn Leu Leu Gly Ala
530                 535                 540
Cys Thr Gln Gly Gly Pro Leu Tyr Val Leu Val Glu Tyr Ala Ala Lys
545                 550                 555                 560
```

```
Gly Asn Leu Arg Glu Phe Leu Arg Ala Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                725                 730                 735

Gln Arg Pro Thr Phe Lys Gln Leu Val Glu Asp Leu Asp Arg Val Leu
            740                 745                 750

Thr Val Thr Ser Thr Asp Glu Tyr Leu Asp Leu Ser Ala Pro Phe Glu
        755                 760                 765

Gln Tyr Ser Pro Gly Gly Gln Asp Thr Pro Ser Ser Ser Ser Ser Gly
    770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 5
<211> LENGTH: 2085
<212> TYPE: DNA
<213> ORGANISM: Homo sapiens FGFR3IIIS

<400> SEQUENCE: 5
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc      120
ccagagcccg ccagcagga gcagttggtc ttcggcagcg gggatgctgt ggagctgagc      180 tgtccccgc cgggggtgg tcccatgggg cccactgtct gggtcaagga tggcacaggg      240
ctggtgccct cggagcgtgt cctggtgggg ccccagcggc tgcaggtgct gaatgcctcc      300
cacgaggact ccgggcccta cagctgccgg cagcggctca gcagcgcgt actgtgccac      360 ttcagtgtgc gggtgacaga cgctccatcc tcgggagatg acgaagacgg ggaggacgag      420
gctgaggaca caggtgtgga cacaggggcc ccttactgga cacggcccga gcggatggac      480
aagaagctgc tggccgtgcc ggccgccaac accgtccgct ccgctgccc agccgctggc      540 aaccccactc cctccatctc ctggctgaag aacggcaggg agttccgcgg cgagcaccgc      600
attggaggca tcaagctgcg gcatcagcag tggagcctgg tcatggaaag cgtggtgccc      660
```

-continued

```
tcggaccgcg gcaactacac ctgcgtcgtg gagaacaagt ttggcagcat ccggcagacg      720
tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga acggcagcaa ggtgggcccg      900
gacggcacac cctacgttac cgtgctcaag gtgtccctgg agtccaacgc gtccatgagc      960
tccaacacac cactggtgcg catcgcaagg ctgtcctcag gggagggccc cacgctggcc     1020
aatgtctccg agctcgagct gcctgccgac cccaaatggg agctgtctcg ggcccggctg     1080
accctgggca agccccttgg ggagggctgc ttcggccagg tggtcatggc ggaggccatc     1140
ggcattgaca aggaccgggc cgccaagcct gtcaccgtag ccgtgaagat gctgaaagac     1200
gatgccactg acaaggacct gtcggacctg gtgtctgaga tggagatgat gaagatgatc     1260
gggaaacaca aaacatcat caacctgctg ggcgcctgca cgcagggcgg gcccctgtac     1320
gtgctggtgg agtacgcggc caagggtaac ctgcgggagt tcctgcgggc gcggcggccc     1380
ccgggcctgg actactcctt cgacacctgc aagccgcccg aggagcagct caccttcaag     1440
gacctggtgt cctgtgccta ccaggtggcc cggggcatgg agtacttggc ctcccagaag     1500
tgcatccaca gggacctggc tgcccgcaat gtgctggtga ccgaggacaa cgtgatgaag     1560
atcgcagact cgggctggcc cgggacgtg cacaacctcg actactacaa gaagacaacc     1620
aacggccggc tgcccgtgaa gtggatggcg cctgaggcct tgtttgaccg agtctacact     1680
caccagagtg acgtctggtc ctttggggtc ctgctctggg agatcttcac gctgggggc     1740 tcccccgtacc ccggcatccc tgtggaggag ctcttcaagc tgctgaagga gggccaccgc     1800
atggacaagc ccgccaactg cacacacgac ctgtacatga tcatgcggga gtgctggcat     1860
gccgcgccct cccagaggcc caccttcaag cagctggtgg aggacctgga ccgtgtcctt     1920
accgtgacgt ccaccgacga gtacctggac ctgtcggcgc ctttcgagca gtactccccg     1980
ggtggccagg acacccccag ctccagctcc tcaggggacg actccgtgtt tgcccacgac     2040
ctgctgcccc cggccccacc cagcagtggg ggctcgcgga cgtga                     2085
```

<210> SEQ ID NO 6
<211> LENGTH: 694
<212> TYPE: PRT
<213> ORGANISM: Homo sapiens FGFR3IIIS

<400> SEQUENCE: 6

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

```
Pro Ser Ser Gly Asp Asp Glu Asp Gly Glu Asp Glu Ala Glu Asp Thr
    130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
            180                 185                 190
Arg Glu Phe Arg Gly Glu His Arg Ile Gly Ile Lys Leu Arg His
        195                 200                 205
Gln Gln Trp Ser Leu Val Met Glu Ser Val Val Pro Ser Asp Arg Gly
    210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
        275                 280                 285
Lys His Val Glu Val Asn Gly Ser Lys Val Gly Pro Asp Gly Thr Pro
    290                 295                 300
Tyr Val Thr Val Leu Lys Val Ser Leu Glu Ser Asn Ala Ser Met Ser
305                 310                 315                 320
Ser Asn Thr Pro Leu Val Arg Ile Ala Arg Leu Ser Ser Gly Glu Gly
                325                 330                 335
Pro Thr Leu Ala Asn Val Ser Glu Leu Glu Leu Pro Ala Asp Pro Lys
            340                 345                 350
Trp Glu Leu Ser Arg Ala Arg Leu Thr Leu Gly Lys Pro Leu Gly Glu
        355                 360                 365
Gly Cys Phe Gly Gln Val Val Met Ala Glu Ala Ile Gly Ile Asp Lys
    370                 375                 380
Asp Arg Ala Ala Lys Pro Val Thr Val Ala Val Lys Met Leu Lys Asp
385                 390                 395                 400
Asp Ala Thr Asp Lys Asp Leu Ser Asp Leu Val Ser Glu Met Glu Met
                405                 410                 415
Met Lys Met Ile Gly Lys His Lys Asn Ile Ile Asn Leu Leu Gly Ala
            420                 425                 430
Cys Thr Gln Gly Gly Pro Leu Tyr Val Leu Val Glu Tyr Ala Ala Lys
        435                 440                 445
Gly Asn Leu Arg Glu Phe Leu Arg Ala Arg Arg Pro Pro Gly Leu Asp
    450                 455                 460
Tyr Ser Phe Asp Thr Cys Lys Pro Pro Glu Glu Gln Leu Thr Phe Lys
465                 470                 475                 480
Asp Leu Val Ser Cys Ala Tyr Gln Val Ala Arg Gly Met Glu Tyr Leu
                485                 490                 495
Ala Ser Gln Lys Cys Ile His Arg Asp Leu Ala Ala Arg Asn Val Leu
            500                 505                 510
Val Thr Glu Asp Asn Val Met Lys Ile Ala Asp Phe Gly Leu Ala Arg
        515                 520                 525
Asp Val His Asn Leu Asp Tyr Tyr Lys Lys Thr Thr Asn Gly Arg Leu
    530                 535                 540
```

```
Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
                660                 665                 670

Asp Asp Ser Val Phe Ala His Asp Leu Leu Pro Pro Ala Pro Pro Ser
            675                 680                 685

Ser Gly Gly Ser Arg Thr
    690

<210> SEQ ID NO 7
<211> LENGTH: 2409
<212> TYPE: DNA
<213> ORGANISM: Bos taurus FGFR3IIIc

<400> SEQUENCE: 7
atgggcgccc cggctcgcgc cctcgcgttt tgcgtggcag tggcggtcat gaccggcgcc      60
gccctcgggt ccccgggcgt ggagccccgc gtcgcgcgga gagcggcaga ggtcccgggc     120
cccgagccca gccccgcagga gcgggccttt ggcagcgggg acaccgtgga gctgagctgc     180
cgcttgccgg cggggggtgcc cacagagccc accgtctggg tgaaggacgg cgtgggcctg     240
gcgccctcgg accgcgtcct ggtggggccg cagcggctac aggtgctcaa cgcctcccac     300
gaggacgccg agcctacag ctgccgccag cgcctctccc agcggctgct gtgcctcttc     360
agcgtgcgcg tgacagatgc tccgtcctca ggggatgacg agggtgggga cgacgaggcc     420
gaggacacag ctggggcccc ttactggacg cggcctgagc ggatggacaa gagctgcta     480
gcggtgccgg ccgccaacac ggttcgcttc cgctgcccag ctgctggcaa ccccacgcca     540
tccatcacct ggctgaagaa cggcaaggag ttccggggcg agcaccgcat cggggggaatc     600
aaactgcggc agcagcagtg gagcctggtc atggagagcg tggtgccctc ggaccgcggc     660
aactacacgt gcgtcgtgga gaacaagttc ggcagaatcc agcagaccta cacctggac     720
gtgctggagc gctctccgca ccggcccatc ctacaggccg gctgcccgc taaccagaca     780
gccgtgctgg gcagcgatgt ggagttccac tgcaaggtct acagcgacgc ccagccccac     840
atccagtggc tcaagcacgt ggaggtgaac ggcagcaagg tggggcccga cggcacgccc     900
tacgtcaccg tgctcaagac ggcgggcgct aacaccaccg acaaggagct agaggttcta     960
tccttgcgca atgtcacctt tgaggacgcg ggggagtaca catgtctggc gggcaattct    1020
atcgggtttt cccatcactc tgcgtggctg gtggtgctgc agctgaggag ggagctggtg    1080
gaagccggtg aggctggcgg tgtgttcgcg ggtgtcctca gctacgggct gggcttcctc    1140
ctcttcatcc tggccgtggc cgccgttacg ctctaccgcc tgaggagccc ccctaagaag    1200
ggcctgggct cgcccgcggt gcacaaggtc tcccgcttcc cgctcaagcg acaggtgtcc    1260
```

```
ttggagtcca gctcatccat gagctccaac acaccgctgg tacgcattgc ccggctgtca      1320
tcgggcgagg gccccaccct ggccaacgtc tctgagctcg agctgcccgc cgaccccaag      1380
tgggagctgt cccgggcccg gctgaccctg ggcaagcctc ttggggaggg ctgcttcggc      1440
caggtggtca tggcagaggc cattggcatc gacaaggacc gagctgccaa gcctgtcacg      1500
gtggccgtga gatgctgaaa gatgacgcc acggataagg acttatcgga cctggtgtcc      1560
gagatggaga tgatgaagat gatcggaaaa cacaagaaca ttatcaacct gctaggcgcc      1620
tgcacgcagg gcgggcccct gtacgtgctg gtggagtacg cggccaaggg caacctgcgg      1680
gaatacctgc gggcacggcg gccccccggc actgactact ccttcgacac ctgccggctg      1740
cccgaggagc agctcacctt caaagacctg gtgtcctgcg cctaccaggt ggcgcggggc      1800
atggagtacc tggcctcgca gaagtgcatc cacagggacc tggcggcccg caacgtgctg      1860
gtgactgagg acaacgtgat gaaaatcgcc gacttcggcc tggctcgtga cgtgcacaac      1920
ctcgactact acaaaaagac cacaaacggc cgcctgcccg tgaagtggat ggcacccgag      1980
gccttgtttg accgcgtcta cacccaccaa agtgacgtct ggtccttcgg ggtcctgctc      2040
tgggagatct tcacgctggg gggctcgccg taccccggca tccccgtgga ggagctcttc      2100
aagctgctga aggaaggcca ccgcatggac aagccggcca actgcacgca tgacctgtac      2160
atgatcatgc gcgagtgctg gcacgccgcg ccctcgcaga ggcccacctt caagcagctg      2220
gtggaggacc tggaccgtgt gctcaccgtg acgtccaccg acgagtacct ggacctgtcg      2280
gtgcccttcg agcagtactc gccgggcggc caggacaccc ccagctccgg ctcctcgggg      2340
gacgactccg tgttcgctca cgacctgctg cccccggccc catccggcag cggaggctcg      2400
cggacgtga                                                              2409
```

<210> SEQ ID NO 8
<211> LENGTH: 802
<212> TYPE: PRT
<213> ORGANISM: Bos taurus FGFR3IIIc

<400> SEQUENCE: 8

```
Met Gly Ala Pro Ala Arg Ala Leu Ala Phe Cys Val Ala Val Ala Val
1               5                   10                  15

Met Thr Gly Ala Ala Leu Gly Ser Pro Gly Val Glu Pro Arg Val Ala
            20                  25                  30

Arg Arg Ala Ala Glu Val Pro Gly Pro Glu Pro Ser Pro Gln Glu Arg
        35                  40                  45

Ala Phe Gly Ser Gly Asp Thr Val Glu Leu Ser Cys Arg Leu Pro Ala
    50                  55                  60

Gly Val Pro Thr Glu Pro Thr Val Trp Val Lys Asp Gly Val Gly Leu
65                  70                  75                  80

Ala Pro Ser Asp Arg Val Leu Val Gly Pro Gln Arg Leu Gln Val Leu
                85                  90                  95

Asn Ala Ser His Glu Asp Ala Gly Ala Tyr Ser Cys Arg Gln Arg Leu
            100                 105                 110

Ser Gln Arg Leu Leu Cys Leu Phe Ser Val Arg Val Thr Asp Ala Pro
        115                 120                 125

Ser Ser Gly Asp Asp Glu Gly Gly Asp Asp Glu Ala Glu Asp Thr Ala
    130                 135                 140

Gly Ala Pro Tyr Trp Thr Arg Pro Glu Arg Met Asp Lys Lys Leu Leu
145                 150                 155                 160
```

-continued

```
Ala Val Pro Ala Ala Asn Thr Val Arg Phe Arg Cys Pro Ala Ala Gly
                165                 170                 175
Asn Pro Thr Pro Ser Ile Thr Trp Leu Lys Asn Gly Lys Glu Phe Arg
                180                 185                 190
Gly Glu His Arg Ile Gly Ile Lys Leu Arg Gln Gln Gln Trp Ser
            195                 200                 205
Leu Val Met Glu Ser Val Val Pro Ser Asp Arg Gly Asn Tyr Thr Cys
210                 215                 220
Val Val Glu Asn Lys Phe Gly Arg Ile Gln Gln Thr Tyr Thr Leu Asp
225                 230                 235                 240
Val Leu Glu Arg Ser Pro His Arg Pro Ile Leu Gln Ala Gly Leu Pro
                245                 250                 255
Ala Asn Gln Thr Ala Val Leu Gly Ser Asp Val Glu Phe His Cys Lys
                260                 265                 270
Val Tyr Ser Asp Ala Gln Pro His Ile Gln Trp Leu Lys His Val Glu
            275                 280                 285
Val Asn Gly Ser Lys Val Gly Pro Asp Gly Thr Pro Tyr Val Thr Val
            290                 295                 300
Leu Lys Thr Ala Gly Ala Asn Thr Thr Asp Lys Glu Leu Glu Val Leu
305                 310                 315                 320
Ser Leu Arg Asn Val Thr Phe Glu Asp Ala Gly Glu Tyr Thr Cys Leu
                325                 330                 335
Ala Gly Asn Ser Ile Gly Phe Ser His His Ser Ala Trp Leu Val Val
            340                 345                 350
Leu Pro Ala Glu Glu Glu Leu Val Glu Ala Gly Glu Ala Gly Gly Val
            355                 360                 365
Phe Ala Gly Val Leu Ser Tyr Gly Leu Gly Phe Leu Leu Phe Ile Leu
370                 375                 380
Ala Val Ala Ala Val Thr Leu Tyr Arg Leu Arg Ser Pro Pro Lys Lys
385                 390                 395                 400
Gly Leu Gly Ser Pro Ala Val His Lys Val Ser Arg Phe Pro Leu Lys
                405                 410                 415
Arg Gln Val Ser Leu Glu Ser Ser Ser Ser Met Ser Ser Asn Thr Pro
                420                 425                 430
Leu Val Arg Ile Ala Arg Leu Ser Ser Gly Glu Gly Pro Thr Leu Ala
                435                 440                 445
Asn Val Ser Glu Leu Glu Leu Pro Ala Asp Pro Lys Trp Glu Leu Ser
450                 455                 460
Arg Ala Arg Leu Thr Leu Gly Lys Pro Leu Gly Glu Gly Cys Phe Gly
465                 470                 475                 480
Gln Val Val Met Ala Glu Ala Ile Gly Ile Asp Lys Asp Arg Ala Ala
                485                 490                 495
Lys Pro Val Thr Val Ala Val Lys Met Leu Lys Asp Asp Ala Thr Asp
                500                 505                 510
Lys Asp Leu Ser Asp Leu Val Ser Glu Met Glu Met Met Lys Met Ile
            515                 520                 525
Gly Lys His Lys Asn Ile Ile Asn Leu Leu Gly Ala Cys Thr Gln Gly
            530                 535                 540
Gly Pro Leu Tyr Val Leu Val Glu Tyr Ala Ala Lys Gly Asn Leu Arg
545                 550                 555                 560
Glu Tyr Leu Arg Ala Arg Arg Pro Pro Gly Thr Asp Tyr Ser Phe Asp
                565                 570                 575
Thr Cys Arg Leu Pro Glu Glu Gln Leu Thr Phe Lys Asp Leu Val Ser
```

```
                    580                585                590
Cys Ala Tyr Gln Val Ala Arg Gly Met Glu Tyr Leu Ala Ser Gln Lys
            595                600                605

Cys Ile His Arg Asp Leu Ala Ala Arg Asn Val Leu Val Thr Glu Asp
            610                615                620

Asn Val Met Lys Ile Ala Asp Phe Gly Leu Ala Arg Asp Val His Asn
625                630                635                640

Leu Asp Tyr Tyr Lys Lys Thr Thr Asn Gly Arg Leu Pro Val Lys Trp
                645                650                655

Met Ala Pro Glu Ala Leu Phe Asp Arg Val Tyr Thr His Gln Ser Asp
            660                665                670

Val Trp Ser Phe Gly Val Leu Leu Trp Glu Ile Phe Thr Leu Gly Gly
            675                680                685

Ser Pro Tyr Pro Gly Ile Pro Val Glu Glu Leu Phe Lys Leu Leu Lys
            690                695                700

Glu Gly His Arg Met Asp Lys Pro Ala Asn Cys Thr His Asp Leu Tyr
705                710                715                720

Met Ile Met Arg Glu Cys Trp His Ala Ala Pro Ser Gln Arg Pro Thr
                725                730                735

Phe Lys Gln Leu Val Glu Asp Leu Asp Arg Val Leu Thr Val Thr Ser
            740                745                750

Thr Asp Glu Tyr Leu Asp Leu Ser Val Pro Phe Glu Gln Tyr Ser Pro
            755                760                765

Gly Gly Gln Asp Thr Pro Ser Ser Gly Ser Ser Gly Asp Asp Ser Val
            770                775                780

Phe Ala His Asp Leu Leu Pro Pro Ala Pro Ser Gly Ser Gly Gly Ser
785                790                795                800

Arg Thr

<210> SEQ ID NO 9
<211> LENGTH: 2409
<212> TYPE: DNA
<213> ORGANISM: Mus musculus FGFR3IIIb

<400> SEQUENCE: 9
atggtagtcc cggcctgcgt gctagtgttc tgcgtggcgg tcgtggctgg agctacttcc      60
gagcctcctg gtccagagca gcgagttgtg cggagagcgg cagaggttcc agggcctgaa     120
cctagccagc aggagcaggt ggccttcggc agtggggaca ccgtggagct gagctgccat     180
cctcctggag gtgcccccac agggcccacg gtctgggcta aggatggtac aggtctggtg     240 gcctccacc gcatcctggt ggggcctcag aggctgcaag tgctaaatgc ctcccacgaa     300
gatgcagggg tctacagctg ccagcaccgg ctcactcggc gtgtgctgtg ccacttcagt     360
gtgcgtgtaa cagatgctcc atcctcagga gatgacgaag atggggagga cgtggctgaa     420
gacacagggg ctccttattg gactcgcccg gagcgaatgg ataagaaact gctggctgtg     480
ccagccgcaa acactgtccg cttccgctgc ccagctgctg caacccctac ccctccatc      540 tcctggctga agaatggcaa agaattccga ggggagcatc gcattggggg catcaagctc     600
cggcaccagc agtggagctt ggtcatggaa agtgtggtac cctccgatcg tggcaactat     660
acctgtgtag ttgagaacaa gtttggcagc atccggcaga catacacact ggatgtgctg     720
gagcgctccc cacaccggcc catcctgcag gctgggctgc cggccaacca gacagccatt     780
ctaggcagtg acgtggagtt ccactgcaag gtgtacagcg atgcacagcc acacatccag     840
```

```
tggctgaagc acgtggaagt gaacggcagc aaggtgggcc ctgacggcac gccctacgtc    900
actgtactca agtcctggat cagtgagaat gtggaggcag acgcacgcct ccgcctggcc    960
aatgtgtcgg agcgggacgg gggcgagtac ctctgtcgag ccaccaattt cataggcgtg   1020
gctgagaagg cctttggct gcgtgttcac gggcccaag cagctgagga ggagctgatg    1080
gaaactgatg aggctggcag cgtgtacgca ggcgtcctca gctacgggt ggtcttcttc    1140
ctcttcatcc tggtggtggc agctgtgata ctctgccgcc tgcgcagtcc cccaaagaag   1200
ggcttgggct cgcccaccgt gcacaaggtc tctcgcttcc cgcttaagcg acaggtgtcc   1260
ttggaatcta actcctctat gaactccaac acacccttg tccggattgc ccggctgtcc    1320
tcaggagaag gtcctgttct ggccaatgtt tctgaacttg agctgcctgc tgaccccaag   1380
tgggagctat ccaggacccg gctgacactt ggtaagcctc ttggagaagg ctgctttgga   1440
caggtggtca tggcagaagc tattggcatc gacaaggacc gtactgccaa gctgtcacc    1500
gtggccgtga gatgctgaa agatgatgcg actgacaagg acctgtcgga cctggtatct   1560
gagatggaga tgatgaaaat gattggcaag cacaagaaca tcattaaacct gctggggggcg   1620
tgcacacagg gtgggcccct gtatgtgctg gtggagtacg cagccaaggg caatctccgg   1680
gagttccttc gggcgcggcg gcctccaggc atggactact cctttgatgc ctgcaggctg   1740
ccagaggaac agctcacctg caaggatcta gtgtcctgtg cctaccaggt ggcacggggc   1800
atggaatact ggcttctca gaagtgtatt cacagagact ggctgccag aaacgtcctg   1860
gtgaccgagg acaatgtgat gaagattgcg actttggcc tggctcgaga tgtgcacaac   1920
ctggactact acaagaagac cacaaatggc cggctacctg tgaagtggat ggcaccagag   1980
gccctttttg accgagtcta cacccaccag agtgatgttt ggtctttttgg tgtcctcctc   2040
tgggagatct ttacgctggg gggctcaccg tatcctggca tcccagtgga agagcttttc   2100
aagctgttga agagggcca ccgcatggac aagccagcca gctgcacaca tgacctgtac   2160
atgatcatgc gggaatgttg gcatgcggtg ccttcacaga ggcccacctt caagcagttg   2220
gtagaggatt tagaccgcat cctcactgtg acatcaaccg acgagtactt ggacctctcc   2280
gtgccgttg agcagtactc gccaggtggc caggacacgc ctagctccag ctcgtccgga   2340
gatgactcgg tgttcaccca tgacctgcta cccccaggtc cacccagtaa cgggggacct   2400
cggacgtga                                                          2409
```

<210> SEQ ID NO 10
<211> LENGTH: 802
<212> TYPE: PRT
<213> ORGANISM: Mus musculus FGFR3IIIb

<400> SEQUENCE: 10

```
Met Val Val Pro Ala Cys Val Leu Val Phe Cys Val Ala Val Ala
 1               5                  10                  15

Gly Ala Thr Ser Glu Pro Pro Gly Pro Glu Gln Arg Val Val Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95
```

```
Ala Ser His Glu Asp Ala Gly Val Tyr Ser Cys Gln His Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Val Gly Pro Asp Gly Thr Pro Tyr Val Thr Val Leu Lys
    290                 295                 300

Ser Trp Ile Ser Glu Asn Val Glu Ala Asp Ala Arg Leu Arg Leu Ala
305                 310                 315                 320

Asn Val Ser Glu Arg Asp Gly Gly Glu Tyr Leu Cys Arg Ala Thr Asn
                325                 330                 335

Phe Ile Gly Val Ala Glu Lys Ala Phe Trp Leu Arg Val His Gly Pro
            340                 345                 350

Gln Ala Ala Glu Glu Glu Leu Met Glu Thr Asp Glu Ala Gly Ser Val
        355                 360                 365

Tyr Ala Gly Val Leu Ser Tyr Gly Val Val Phe Phe Leu Phe Ile Leu
    370                 375                 380

Val Val Ala Ala Val Ile Leu Cys Arg Leu Arg Ser Pro Pro Lys Lys
385                 390                 395                 400

Gly Leu Gly Ser Pro Thr Val His Lys Val Ser Arg Phe Pro Leu Lys
                405                 410                 415

Arg Gln Val Ser Leu Glu Ser Asn Ser Ser Met Asn Ser Asn Thr Pro
            420                 425                 430

Leu Val Arg Ile Ala Arg Leu Ser Ser Gly Glu Gly Pro Val Leu Ala
        435                 440                 445

Asn Val Ser Glu Leu Glu Leu Pro Ala Asp Pro Lys Trp Glu Leu Ser
    450                 455                 460

Arg Thr Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Thr Ala
                485                 490                 495

Lys Pro Val Thr Val Ala Val Lys Met Leu Lys Asp Asp Ala Thr Asp
            500                 505                 510
```

```
Lys Asp Leu Ser Asp Leu Val Ser Glu Met Glu Met Met Lys Met Ile
            515                 520                 525
Gly Lys His Lys Asn Ile Ile Asn Leu Leu Gly Ala Cys Thr Gln Gly
        530                 535                 540
Gly Pro Leu Tyr Val Leu Val Glu Tyr Ala Ala Lys Gly Asn Leu Arg
545                 550                 555                 560
Glu Phe Leu Arg Ala Arg Arg Pro Pro Gly Met Asp Tyr Ser Phe Asp
                565                 570                 575
Ala Cys Arg Leu Pro Glu Glu Gln Leu Thr Cys Lys Asp Leu Val Ser
                580                 585                 590
Cys Ala Tyr Gln Val Ala Arg Gly Met Glu Tyr Leu Ala Ser Gln Lys
            595                 600                 605
Cys Ile His Arg Asp Leu Ala Ala Arg Asn Val Leu Val Thr Glu Asp
        610                 615                 620
Asn Val Met Lys Ile Ala Asp Phe Gly Leu Ala Arg Asp Val His Asn
625                 630                 635                 640
Leu Asp Tyr Tyr Lys Lys Thr Thr Asn Gly Arg Leu Pro Val Lys Trp
                645                 650                 655
Met Ala Pro Glu Ala Leu Phe Asp Arg Val Tyr Thr His Gln Ser Asp
                660                 665                 670
Val Trp Ser Phe Gly Val Leu Leu Trp Glu Ile Phe Thr Leu Gly Gly
            675                 680                 685
Ser Pro Tyr Pro Gly Ile Pro Val Glu Glu Leu Phe Lys Leu Leu Lys
        690                 695                 700
Glu Gly His Arg Met Asp Lys Pro Ala Ser Cys Thr His Asp Leu Tyr
705                 710                 715                 720
Met Ile Met Arg Glu Cys Trp His Ala Val Pro Ser Gln Arg Pro Thr
                725                 730                 735
Phe Lys Gln Leu Val Glu Asp Leu Asp Arg Ile Leu Thr Val Thr Ser
                740                 745                 750
Thr Asp Glu Tyr Leu Asp Leu Ser Val Pro Phe Glu Gln Tyr Ser Pro
            755                 760                 765
Gly Gly Gln Asp Thr Pro Ser Ser Ser Ser Gly Asp Asp Ser Val
        770                 775                 780
Phe Thr His Asp Leu Leu Pro Pro Gly Pro Pro Ser Asn Gly Gly Pro
785                 790                 795                 800
Arg Thr

<210> SEQ ID NO 11
<211> LENGTH: 2403
<212> TYPE: DNA
<213> ORGANISM: Mus musculus FGFR3IIIc

<400> SEQUENCE: 11
atggtagtcc cggcctgcgt gctagtgttc tgcgtggcgg tcgtggctgg agctacttcc      60
gagcctcctg gtccagagca gcgagttgtg cggagagcgg cagaggttcc agggcctgaa     120
cctagccagc aggagcaggt ggccttcggc agtggggaca ccgtggagct gagctgccat     180
cctcctggag gtgcccccac agggcccacg gtctgggcta aggatggtac aggtctggtg     240
gcctcccacc gcatcctggt ggggcctcag aggctgcaag tgctaaatgc ctcccacgaa     300
gatgcagggg tctacagctg ccagcaccgg ctcactcggc gtgtgctgtg ccacttcagt     360
gtgcgtgtaa cagatgctcc atcctcagga gatgacgaag atggggagga cgtggctgaa     420
gacacagggg ctccttattg gactcgcccg gagcgaatgg ataagaaact gctggctgtg     480
```

```
ccagccgcaa acactgtccg cttccgctgc ccagctgctg gcaaccctac cccctccatc    540
tcctggctga agaatggcaa agaattccga ggggagcatc gcattggggg catcaagctc    600
cggcaccagc agtggagctt ggtcatggaa agtgtggtac cctccgatcg tggcaactat    660
acctgtgtag ttgagaacaa gtttggcagc atccggcaga catacacact ggatgtgctg    720
gagcgctccc cacaccggcc catcctgcag gctgggctgc cggccaacca gacagccatt    780
ctaggcagtg acgtggagtt ccactgcaag gtgtacagcg atgcacagcc acacatccag    840
tggctgaagc acgtggaagt gaacggcagc aaggtgggcc ctgacggcac gccctacgtc    900
actgtactca agactgcagg cgctaacacc accgacaagg agctagaggt tctgtccttg    960
cacaatgtca cctttgagga cgcggggggag tacacctgcc tggcgggcaa ttctattggg   1020
ttttcccatc actctgcgtg gctggtggtg ctgccagctg aggaggagct gatggaaact   1080
gatgaggctg gcagcgtgta cgcaggcgtc ctcagctacg gggtggtctt cttcctcttc   1140
atcctggtgg tggcagctgt gatactctgc cgcctgcgca gtcccccaaa gaagggcttg   1200
ggctcgccca ccgtgcacaa ggtctctcgc ttcccgctta agcgacaggt gtccttggaa   1260
tctaactcct ctatgaactc caacacaccc cttgtccgga ttgcccggct gtcctcagga   1320
gaaggtcctg ttctggccaa tgtttctgaa cttgagctgc ctgctgaccc caagtgggag   1380
ctatccagga cccggctgac acttggtaag cctcttggag aaggctgctt tggacaggtg   1440
gtcatggcag aagctattgg catcgacaag accgtactgc caagcctgt caccgtggcc   1500 gtgaagatgc tgaaagatga tgcgactgac aaggacctgt cggacctggt atctgagatg   1560
gagatgatga aaatgattgg caagcacaag aacatcatta acctgctggg ggcgtgcaca   1620
cagggtgggc ccctgtatgt gctggtggag tacgcagcca agggcaatct ccgggagttc   1680
cttcgggcgc ggcggcctcc aggcatggac tactcctttg atgcctgcag gctgccagag   1740
gaacagctca cctgcaagga tctagtgtcc tgtgcctacc aggtggcacg gggcatggaa   1800
tacttggctt ctcagaagtg tattcacaga gacttggctg ccagaaacgt cctggtgacc   1860
gaggacaatg tgatgaagat tgcggacttt ggcctggctc gagatgtgca aacctggac   1920 tactacaaga gaccacaaa tggccggcta cctgtgaagt ggatggcacc agaggccctt   1980
tttgaccgag tctacaccca ccagagtgat gtttggtctt ttggtgtcct cctctgggag   2040
atctttacgc tggggggctc accgtatcct ggcatcccag tggaagagct tttcaagctg   2100
ttgaaagagg ccaccgcat ggacaagcca gccagctgca cacatgacct gtacatgatc   2160
atgcgggaat gttggcatgc ggtgccttca cagaggccca ccttcaagca gttggtagag   2220
gatttagacc gcatcctcac tgtgacatca accgacgagt acttggacct ctccgtgccg   2280
tttgagcagt actcgccagg tggccaggac acgcctagct ccagctcgtc cggagatgac   2340
tcggtgttca cccatgacct gctacccca ggtccaccca gtaacggggg acctcggacg   2400
tga                                                                  2403
```

<210> SEQ ID NO 12
<211> LENGTH: 800
<212> TYPE: PRT
<213> ORGANISM: Mus musculus FGFR3IIIc

<400> SEQUENCE: 12

Met Val Val Pro Ala Cys Val Leu Val Phe Cys Val Ala Val Ala
1               5                   10                  15

Gly Ala Thr Ser Glu Pro Pro Gly Pro Glu Gln Arg Val Val Arg Arg

-continued

```
                20                  25                  30
Ala Ala Glu Val Pro Gly Pro Glu Pro Ser Gln Gln Glu Gln Val Ala
         35                  40                  45
Phe Gly Ser Gly Asp Thr Val Glu Leu Ser Cys His Pro Pro Gly Gly
         50                  55                  60
Ala Pro Thr Gly Pro Thr Val Trp Ala Lys Asp Gly Thr Gly Leu Val
 65                  70                  75                  80
Ala Ser His Arg Ile Leu Val Gly Pro Gln Arg Leu Gln Val Leu Asn
                 85                  90                  95
Ala Ser His Glu Asp Ala Gly Val Tyr Ser Cys Gln His Arg Leu Thr
                100                 105                 110
Arg Arg Val Leu Cys His Phe Ser Val Arg Val Thr Asp Ala Pro Ser
                115                 120                 125
Ser Gly Asp Asp Glu Asp Gly Glu Asp Val Ala Glu Asp Thr Gly Ala
        130                 135                 140
Pro Tyr Trp Thr Arg Pro Glu Arg Met Asp Lys Lys Leu Leu Ala Val
145                 150                 155                 160
Pro Ala Ala Asn Thr Val Arg Phe Arg Cys Pro Ala Ala Gly Asn Pro
                165                 170                 175
Thr Pro Ser Ile Ser Trp Leu Lys Asn Gly Lys Glu Phe Arg Gly Glu
                180                 185                 190
His Arg Ile Gly Gly Ile Lys Leu Arg His Gln Gln Trp Ser Leu Val
                195                 200                 205
Met Glu Ser Val Val Pro Ser Asp Arg Gly Asn Tyr Thr Cys Val Val
        210                 215                 220
Glu Asn Lys Phe Gly Ser Ile Arg Gln Thr Tyr Thr Leu Asp Val Leu
225                 230                 235                 240
Glu Arg Ser Pro His Arg Pro Ile Leu Gln Ala Gly Leu Pro Ala Asn
                245                 250                 255
Gln Thr Ala Ile Leu Gly Ser Asp Val Glu Phe His Cys Lys Val Tyr
                260                 265                 270
Ser Asp Ala Gln Pro His Ile Gln Trp Leu Lys His Val Glu Val Asn
                275                 280                 285
Gly Ser Lys Val Gly Pro Asp Gly Thr Pro Tyr Val Thr Val Leu Lys
        290                 295                 300
Thr Ala Gly Ala Asn Thr Thr Asp Lys Glu Leu Glu Val Leu Ser Leu
305                 310                 315                 320
His Asn Val Thr Phe Glu Asp Ala Gly Glu Tyr Thr Cys Leu Ala Gly
                325                 330                 335
Asn Ser Ile Gly Phe Ser His His Ser Ala Trp Leu Val Val Leu Pro
                340                 345                 350
Ala Glu Glu Glu Leu Met Glu Thr Asp Glu Ala Gly Ser Val Tyr Ala
                355                 360                 365
Gly Val Leu Ser Tyr Gly Val Val Phe Phe Leu Phe Ile Leu Val Val
        370                 375                 380
Ala Ala Val Ile Leu Cys Arg Leu Arg Ser Pro Pro Lys Lys Gly Leu
385                 390                 395                 400
Gly Ser Pro Thr Val His Lys Val Ser Arg Phe Pro Leu Lys Arg Gln
                405                 410                 415
Val Ser Leu Glu Ser Asn Ser Ser Met Asn Ser Asn Thr Pro Leu Val
                420                 425                 430
Arg Ile Ala Arg Leu Ser Ser Gly Glu Gly Pro Val Leu Ala Asn Val
                435                 440                 445
```

| | | | | | | | | | | | |
|---|---|---|---|---|---|---|---|---|---|---|---|
| Ser | Glu | Leu | Glu | Leu | Pro | Ala | Asp | Pro | Lys | Trp | Glu | Leu | Ser | Arg | Thr |
| | 450 | | | | 455 | | | | | 460 | |

Ser Glu Leu Glu Leu Pro Ala Asp Pro Lys Trp Glu Leu Ser Arg Thr
    450                 455                     460

Arg Leu Thr Leu Gly Lys Pro Leu Gly Glu Gly Cys Phe Gly Gln Val
465             470                 475                     480

Val Met Ala Glu Ala Ile Gly Ile Asp Lys Asp Arg Thr Ala Lys Pro
                485                 490                 495

Val Thr Val Ala Val Lys Met Leu Lys Asp Asp Ala Thr Asp Lys Asp
            500                 505                 510

Leu Ser Asp Leu Val Ser Glu Met Glu Met Met Lys Met Ile Gly Lys
        515                 520                 525

His Lys Asn Ile Ile Asn Leu Leu Gly Ala Cys Thr Gln Gly Gly Pro
    530                 535                 540

Leu Tyr Val Leu Val Glu Tyr Ala Ala Lys Gly Asn Leu Arg Glu Phe
545                 550                 555                 560

Leu Arg Ala Arg Arg Pro Pro Gly Met Asp Tyr Ser Phe Asp Ala Cys
                565                 570                 575

Arg Leu Pro Glu Glu Gln Leu Thr Cys Lys Asp Leu Val Ser Cys Ala
            580                 585                 590

Tyr Gln Val Ala Arg Gly Met Glu Tyr Leu Ala Ser Gln Lys Cys Ile
        595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Val Leu Leu Trp Glu Ile Phe Thr Leu Gly Gly Ser Pro
        675                 680                 685

Tyr Pro Gly Ile Pro Val Glu Glu Leu Phe Lys Leu Leu Lys Glu Gly
    690                 695                 700

His Arg Met Asp Lys Pro Ala Ser Cys Thr His Asp Leu Tyr Met Ile
705                 710                 715                 720

Met Arg Glu Cys Trp His Ala Val Pro Ser Gln Arg Pro Thr Phe Lys
                725                 730                 735

Gln Leu Val Glu Asp Leu Asp Arg Ile Leu Thr Val Thr Ser Thr Asp
            740                 745                 750

Glu Tyr Leu Asp Leu Ser Val Pro Phe Glu Gln Tyr Ser Pro Gly Gly
        755                 760                 765

Gln Asp Thr Pro Ser Ser Ser Ser Gly Asp Asp Ser Val Phe Thr
    770                 775                 780

His Asp Leu Leu Pro Pro Gly Pro Pro Ser Asn Gly Gly Pro Arg Thr
785                 790                 795                 800

<210> SEQ ID NO 13
<211> LENGTH: 2349
<212> TYPE: DNA
<213> ORGANISM: Mus musculus FGFR3III-delAcid

<400> SEQUENCE: 13
atggtagtcc cggcctgcgt gctagtgttc tgcgtggcgg tcgtggctgg agctacttcc    60
gagcctcctg gtccagagca gcgagttgtg cggagagcgg cagaggttcc agggcctgaa   120

```
cctagccagc aggagcaggt ggccttcggc agtggggaca ccgtggagct gagctgccat        180
cctcctggag gtgccccac agggcccacg gtctgggcta aggatggtac aggtctggtg        240
gcctcccacc gcatcctggt ggggcctcag aggctgcaag tgctaaatgc ctcccacgaa        300
gatgcagggg tctacagctg ccagcaccgg ctcactcggc gtgtgctgtg ccacttcagt        360
gtgcgtgtaa caggggctcc ttattggact cgcccggagc gaatggataa gaaactgctg        420
gctgtgccag ccgcaaacac tgtccgcttc cgctgcccag ctgctggcaa ccctaccccc        480
tccatctcct ggctgaagaa tggcaaagaa ttccgagggg agcatcgcat tgggggcatc        540
aagctccggc accagcagtg gagcttggtc atggaaagtg tggtaccctc cgatcgtggc        600
aactatacct gtgtagttga aacaagttt ggcagcatcc ggcagacata cacactggat        660
gtgctggagc gctccccaca ccggcccatc ctgcaggctg gctgccggc caaccagaca        720 gccattctag gcagtgacgt ggagttccac tgcaaggtgt acagcgatgc acagccacac        780
atccagtggc tgaagcacgt ggaagtgaac ggcagcaagg tgggccctga cggcacgccc        840
tacgtcactg tactcaagac tgcaggcgct aacaccaccg acaaggagct agaggttctg        900
tccttgcaca atgtcacctt tgaggacgcg ggggagtaca cctgcctggc gggcaattct        960
attgggtttt cccatcactc tgcgtggctg gtggtgctgc agctgaggga ggagctgatg       1020
gaaactgatg aggctggcag cgtgtacgca ggcgtcctca gctacggggt ggtcttcttc       1080
ctcttcatcc tggtggtggc agctgtgata ctctgccgcc tgcgcagtcc cccaaagaag       1140
ggcttgggct cgcccaccgt gcacaaggtc tctcgcttcc cgcttaagcg acaggtgtcc       1200
ttggaatcta actcctctat gaactccaac acaccccttg tccggattgc ccggctgtcc       1260
tcaggagaag gtcctgttct ggccaatgtt tctgaacttg agctgcctgc tgaccccaag       1320
tgggagctat ccaggacccg gctgacactt ggtaagcctc ttggagaagg ctgctttgga       1380
caggtggtca tggcagaagc tattggcatc gacaaggacc gtactgccaa gcctgtcacc       1440
gtggccgtga agatgctgaa agatgatgcg actgacaagg acctgtcgga cctggtatct       1500
gagatggaga tgatgaaaat gattggcaag cacaagaaca tcattaacct gctgggggcg       1560
tgcacacagg gtgggcccct gtatgtgctg gtggagtacg cagccaaggg caatctccgg       1620
gagttccttc gggcgcggcg gcctccaggc atggactact cctttgatgc ctgcaggctg       1680
ccagaggaac agctccacctg caaggatcta gtgtcctgtg cctaccaggt ggcacggggc       1740
atgaatactc tggcttctca gaagtgtatt cacagagact ggctgccag aaacgtcctg       1800 gtgaccgagg acaatgtgat gaagattgcg gactttggcc tggctcgaga tgtgcacaac       1860
ctggactact acaagaagac cacaaatggc cggctacctg tgaagtggat ggcaccagag       1920 gcccttttg accgagtcta cacccaccag agtgatgttt ggtcttttgg tgtcctcctc       1980
tgggagatct ttacgctggg gggctcaccg tatcctggca tcccagtgga agagcttttc       2040
aagctgttga agagggcca ccgcatggac aagccagcca gctgcacaca tgacctgtac       2100
atgatcatgc gggaatgttg gcatgcggtg ccttcacaga ggcccacctt caagcagttg       2160
gtagaggatt tagaccgcat cctcactgtg acatcaaccg acgagtactt ggacctctcc       2220
gtgccgtttg agcagtactc gccaggtggc caggacacgc ctagctccag ctcgtccgga       2280
gatgactcgg tgttcaccca tgacctgcta ccccaggtc cacccagtaa cgggggacct       2340
cggacgtga                                                              2349
```

<210> SEQ ID NO 14
<211> LENGTH: 782

<212> TYPE: PRT
<213> ORGANISM: Mus musculus FGFR3III-delAcid

<400> SEQUENCE: 14

```
Met Val Val Pro Ala Cys Val Leu Val Phe Cys Val Ala Val Ala
1               5                   10                  15

Gly Ala Thr Ser Glu Pro Pro Gly Pro Glu Gln Arg Val Val Arg Arg
                20                  25                  30

Ala Ala Glu Val Pro Gly Pro Glu Pro Ser Gln Gln Glu Gln Val Ala
                35                  40                  45

Phe Gly Ser Gly Asp Thr Val Glu Leu Ser Cys His Pro Pro Gly Gly
50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
                100                 105                 110

Arg Arg Val Leu Cys His Phe Ser Val Arg Val Thr Gly Ala Pro Tyr
                115                 120                 125

Trp Thr Arg Pro Glu Arg Met Asp Lys Lys Leu Leu Ala Val Pro Ala
                130                 135                 140

Ala Asn Thr Val Arg Phe Arg Cys Pro Ala Ala Gly Asn Pro Thr Pro
145                 150                 155                 160

Ser Ile Ser Trp Leu Lys Asn Gly Lys Glu Phe Arg Gly Glu His Arg
                165                 170                 175

Ile Gly Gly Ile Lys Leu Arg His Gln Gln Trp Ser Leu Val Met Glu
                180                 185                 190

Ser Val Val Pro Ser Asp Arg Gly Asn Tyr Thr Cys Val Val Glu Asn
                195                 200                 205

Lys Phe Gly Ser Ile Arg Gln Thr Tyr Thr Leu Asp Val Leu Glu Arg
                210                 215                 220

Ser Pro His Arg Pro Ile Leu Gln Ala Gly Leu Pro Ala Asn Gln Thr
225                 230                 235                 240

Ala Ile Leu Gly Ser Asp Val Glu Phe His Cys Lys Val Tyr Ser Asp
                245                 250                 255

Ala Gln Pro His Ile Gln Trp Leu Lys His Val Glu Val Asn Gly Ser
                260                 265                 270

Lys Val Gly Pro Asp Gly Thr Pro Tyr Val Thr Val Leu Lys Thr Ala
                275                 280                 285

Gly Ala Asn Thr Thr Asp Lys Glu Leu Glu Val Leu Ser Leu His Asn
                290                 295                 300

Val Thr Phe Glu Asp Ala Gly Glu Tyr Thr Cys Leu Ala Gly Asn Ser
305                 310                 315                 320

Ile Gly Phe Ser His His Ser Ala Trp Leu Val Val Leu Pro Ala Glu
                325                 330                 335

Glu Glu Leu Met Glu Thr Asp Glu Ala Gly Ser Val Tyr Ala Gly Val
                340                 345                 350

Leu Ser Tyr Gly Val Val Phe Phe Leu Phe Ile Leu Val Val Ala Ala
                355                 360                 365

Val Ile Leu Cys Arg Leu Arg Ser Pro Lys Lys Gly Leu Gly Ser
                370                 375                 380

Pro Thr Val His Lys Val Ser Arg Phe Pro Leu Lys Arg Gln Val Ser
385                 390                 395                 400
```

```
Leu Glu Ser Asn Ser Ser Met Asn Ser Asn Thr Pro Leu Val Arg Ile
                405                 410                 415
Ala Arg Leu Ser Ser Gly Glu Gly Pro Val Leu Ala Asn Val Ser Glu
            420                 425                 430
Leu Glu Leu Pro Ala Asp Pro Lys Trp Glu Leu Ser Arg Thr Arg Leu
        435                 440                 445
Thr Leu Gly Lys Pro Leu Gly Glu Gly Cys Phe Gly Gln Val Val Met
450                 455                 460
Ala Glu Ala Ile Gly Ile Asp Lys Asp Arg Thr Ala Lys Pro Val Thr
465                 470                 475                 480
Val Ala Val Lys Met Leu Lys Asp Asp Ala Thr Asp Lys Asp Leu Ser
                485                 490                 495
Asp Leu Val Ser Glu Met Glu Met Met Lys Met Ile Gly Lys His Lys
            500                 505                 510
Asn Ile Ile Asn Leu Leu Gly Ala Cys Thr Gln Gly Gly Pro Leu Tyr
        515                 520                 525
Val Leu Val Glu Tyr Ala Ala Lys Gly Asn Leu Arg Glu Phe Leu Arg
    530                 535                 540
Ala Arg Arg Pro Pro Gly Met Asp Tyr Ser Phe Asp Ala Cys Arg Leu
545                 550                 555                 560
Pro Glu Glu Gln Leu Thr Cys Lys Asp Leu Val Ser Cys Ala Tyr Gln
                565                 570                 575
Val Ala Arg Gly Met Glu Tyr Leu Ala Ser Gln Lys Cys Ile His Arg
            580                 585                 590
Asp Leu Ala Ala Arg Asn Val Leu Val Thr Glu Asp Asn Val Met Lys
        595                 600                 605
Ile Ala Asp Phe Gly Leu Ala Arg Asp Val His Asn Leu Asp Tyr Tyr
    610                 615                 620
Lys Lys Thr Thr Asn Gly Arg Leu Pro Val Lys Trp Met Ala Pro Glu
625                 630                 635                 640
Ala Leu Phe Asp Arg Val Tyr Thr His Gln Ser Asp Val Trp Ser Phe
                645                 650                 655
Gly Val Leu Leu Trp Glu Ile Phe Thr Leu Gly Gly Ser Pro Tyr Pro
            660                 665                 670
Gly Ile Pro Val Glu Glu Leu Phe Lys Leu Leu Lys Glu Gly His Arg
        675                 680                 685
Met Asp Lys Pro Ala Ser Cys Thr His Asp Leu Tyr Met Ile Met Arg
    690                 695                 700
Glu Cys Trp His Ala Val Pro Ser Gln Arg Pro Thr Phe Lys Gln Leu
705                 710                 715                 720
Val Glu Asp Leu Asp Arg Ile Leu Thr Val Thr Ser Thr Asp Glu Tyr
                725                 730                 735
Leu Asp Leu Ser Val Pro Phe Glu Gln Tyr Ser Pro Gly Gly Gln Asp
            740                 745                 750
Thr Pro Ser Ser Ser Ser Gly Asp Asp Ser Val Phe Thr His Asp
        755                 760                 765
Leu Leu Pro Pro Gly Pro Pro Ser Asn Gly Gly Pro Arg Thr
    770                 775                 780

<210> SEQ ID NO 15
<211> LENGTH: 2409
<212> TYPE: DNA
<213> ORGANISM: Rattus norvegicus FGFR3IIIb
```

<400> SEQUENCE: 15

```
atggtagtcc cggcctgcgt gctagtgttc tgcgtggcgg tcgtggctgg agttacttcc        60
gagcctcccg gtccagagca gcgagttggt cggagagcgg cagaggttcc agggcctgaa       120
cctagccagc aggagcaggt ggccttcggc agtggggaca ctgtggagct gagctgccat       180
ccgcctggag gtgcccccac aggcccact ctctgggcta aggacggtgt ggggctggtg        240
gcctccacc gtatcctggt ggggcctcag aggcttcaag tgctaaacgc cacccatgag        300
gatgctgggg tctacagctg ccagcagcgg ctaacccggc gtgtgctgtg ccactttagt       360
gtgcgtgtaa cagatgctcc gtcctcagga gatgacgaag atggggagga cgtggctgaa       420
gacacagggg ctccttactg gactcgaccg gagcgtatgg ataagaaact gctggctgtg       480
ccagctgcaa acactgtacg cttccgctgc cagctgctg caacccccac ccctccatc         540
ccctggctga agaacggcaa agaattccga ggggagcacc gcattggggg cattaagctc       600
cggcaccagc agtggagctt ggtcatgaa agtgtggtgc cctctgaccg cggcaattac        660
acctgcgtgg ttgagaacaa gtttggcagc atccggcaga cgtacaccct ggatgtgctg       720
gagcgctccc cacaccggcc catcctgcag gctgggctgc cagccaacca gacagccgtt       780
ctgggcagtg acgtggagtt ccactgcaag gtgtacagcg acgcacagcc acacatccag       840
tggctgaagc acgtggaggt gaatgggagc aaggtgggcc ctgacggcac gccctacgtc       900
actgtactca gtcctggat cagtgagaat gtggaggcag acgcacgcct ccgcctggcc        960
aatgtgtcgg agcgggacgg gggcgagtac ctctgtcgag ccaccaattt catagcgtg       1020
gccgagaagg cctttttggct tcgtgttcac gggccccaag cagccgagga ggagctgatg      1080
gaagttgacg aggctggcag cgtgtacgcg ggtgtcctca gctacggggt gggcttcttc      1140
ctcttcatcc tggtggtggc ggcagtgacg ctctgccgtc tgcgcagtcc cccaaagaag      1200
ggcctgggct cgcccaccgt gcacaaggtc tctcgcttcc cgcttaagcg acaggtgtcc      1260
ttggagtcta attcctctat gaactccaac acacctctcg tccggattgc ccggctgtcc      1320
tcaggagaag gtcctgtcct ggccaatgtt tctgaacttg agctgcctgc tgaccccaag      1380
tgggagctat ccaggacccg gctgacactc ggtaagcctc ttggagaagg ctgcttggga      1440
caggttgtca tggcagaagc tattggcatc gacaaggacc gcactgccaa gcctgtcacc      1500
gtggccgtga agatgctgaa agatgatgcg actgacaagg acctgtcgga cctggtgtct     1560
gagatggaga tgatgaaaat gattggcaag cacaagaaca tcattaacct gttgggggcc     1620
tgcacccagg gtgggcccct gtatgtgctg gtggagtatg cagccaaggg caacctgcga     1680
gagttcctcc gggcacggcg gcctccaggc atggattact cctttgatgc ctgcaggctg     1740
ccagaggaac agctcacctg caaggatctg gtgtcctgtg cctaccaggt ggcacgggc      1800
atggagtact ggcttccca gaagtgtatt cacagagacc tggctgccag aaacgtgctg     1860
gtgactgagg acaatgtgat gaagattgca gactttggcc tggcccgaga tgtgcacaac     1920
ctggattact acaagaagac cacaaatggc cggctacctg tgaagtggat ggcaccagag     1980
gcccttttg accgagtcta cacccatcag agtgatgtct ggtcctttgg tgtcctcctc     2040
tgggagatct ttacactggg tgggtcacca tatcctggca tcccagtgga agagcttttc     2100
aagctgttga agagggcca ccgcatggac aagccagcca actgcacaca tgacctgtac     2160
atgatcatgc gggaatgttg gcatgcagtg ccttcacaga ggcccacctt caagcagttg     2220
gtagaggatt tagaccgcat cctcacggtg acatcaactg acgagtactt ggacctctcg     2280
gtgccatttg aacagtactc gccaggtggc caagatactc ctagctccag ctcgtccggg     2340
```

```
gacgactctg tgttcaccca tgacctgcta cccccaggcc cacccagcaa tggggggacct    2400 cggacgtga                                                             2409
```

<210> SEQ ID NO 16
<211> LENGTH: 802
<212> TYPE: PRT
<213> ORGANISM: Rattus norvegicus FGFR3IIIb

<400> SEQUENCE: 16

```
Met Val Pro Ala Cys Val Leu Val Phe Cys Val Ala Val Val Ala
 1               5                  10                  15

Gly Val Thr Ser Glu Pro Pro Gly Pro Glu Gln Arg Val Gly Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Leu Trp Ala Lys Asp Gly Val Gly Leu Val
65                  70                  75                  80

Ala Ser His Arg Ile Leu Val Gly Pro Gln Arg Leu Gln Val Leu Asn
                85                  90                  95

Ala Thr His Glu Asp Ala Gly Val Tyr Ser Cys Gln Gln Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Pro Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Val Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Val Gly Pro Asp Gly Thr Pro Tyr Val Thr Val Leu Lys
    290                 295                 300

Ser Trp Ile Ser Glu Asn Val Glu Ala Asp Ala Arg Leu Arg Leu Ala
305                 310                 315                 320

Asn Val Ser Glu Arg Asp Gly Gly Glu Tyr Leu Cys Arg Ala Thr Asn
                325                 330                 335

Phe Ile Gly Val Ala Glu Lys Ala Phe Trp Leu Arg Val His Gly Pro
            340                 345                 350
```

```
Gln Ala Ala Glu Glu Leu Met Glu Val Asp Glu Ala Gly Ser Val
        355                 360                 365

Tyr Ala Gly Val Leu Ser Tyr Gly Val Gly Phe Phe Leu Phe Ile Leu
    370                 375                 380

Val Val Ala Ala Val Thr Leu Cys Arg Leu Arg Ser Pro Pro Lys Lys
385                 390                 395                 400

Gly Leu Gly Ser Pro Thr Val His Lys Val Ser Arg Phe Pro Leu Lys
                405                 410                 415

Arg Gln Val Ser Leu Glu Ser Asn Ser Ser Met Asn Ser Asn Thr Pro
            420                 425                 430

Leu Val Arg Ile Ala Arg Leu Ser Gly Glu Gly Pro Val Leu Ala
        435                 440                 445

Asn Val Ser Glu Leu Glu Leu Pro Ala Asp Pro Lys Trp Glu Leu Ser
    450                 455                 460

Arg Thr Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Thr Ala
                485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
        515                 520                 525

Gly Lys His Lys Asn Ile Ile Asn Leu Leu Gly Ala Cys Thr Gln Gly
    530                 535                 540

Gly Pro Leu Tyr Val Leu Val Glu Tyr Ala Ala Lys Gly Asn Leu Arg
545                 550                 555                 560

Glu Phe Leu Arg Ala Arg Arg Pro Pro Gly Met Asp Tyr Ser Phe Asp
                565                 570                 575

Ala Cys Arg Leu Pro Glu Glu Gln Leu Thr Cys Lys Asp Leu Val Ser
            580                 585                 590

Cys Ala Tyr Gln Val Ala Arg Gly Met Glu Tyr Leu Ala Ser Gln Lys
        595                 600                 605

Cys Ile His Arg Asp Leu Ala Ala Arg Asn Val Leu Val Thr Glu Asp
    610                 615                 620

Asn Val Met Lys Ile Ala Asp Phe Gly Leu Ala Arg Asp Val His Asn
625                 630                 635                 640

Leu Asp Tyr Tyr Lys Lys Thr Thr Asn Gly Arg Leu Pro Val Lys Trp
                645                 650                 655

Met Ala Pro Glu Ala Leu Phe Asp Arg Val Tyr Thr His Gln Ser Asp
            660                 665                 670

Val Trp Ser Phe Gly Val Leu Leu Trp Glu Ile Phe Thr Leu Gly Gly
        675                 680                 685

Ser Pro Tyr Pro Gly Ile Pro Val Glu Glu Leu Phe Lys Leu Leu Lys
    690                 695                 700

Glu Gly His Arg Met Asp Lys Pro Ala Asn Cys Thr His Asp Leu Tyr
705                 710                 715                 720

Met Ile Met Arg Glu Cys Trp His Ala Val Pro Ser Gln Arg Pro Thr
                725                 730                 735

Phe Lys Gln Leu Val Glu Asp Leu Asp Arg Ile Leu Thr Val Thr Ser
            740                 745                 750

Thr Asp Glu Tyr Leu Asp Leu Ser Val Pro Phe Glu Gln Tyr Ser Pro
        755                 760                 765

Gly Gly Gln Asp Thr Pro Ser Ser Ser Ser Gly Asp Asp Ser Val
```

770              775              780
Phe Thr His Asp Leu Leu Pro Pro Gly Pro Pro Ser Asn Gly Gly Pro
785              790              795              800

Arg Thr

<210> SEQ ID NO 17
<211> LENGTH: 2403
<212> TYPE: DNA
<213> ORGANISM: Rattus norvegicus FGFR3IIIc

<400> SEQUENCE: 17

| | | | | | |
|---|---|---|---|---|---|
| atggtagtcc | cggcctgcgt | gctagtgttc | tgcgtggcgg | tcgtggctgg | agttacttcc | 60 |
| gagcctcccg | gtccagagca | gcgagttggt | cggagagcgg | cagaggttcc | agggcctgaa | 120 |
| cctagccagc | aggagcaggt | ggccttcggc | agtggggaca | ctgtggagct | gagctgccat | 180 |
| ccgcctggag | gtgcccccac | aggccccact | ctctgggcta | aggacggtgt | ggggctggtg | 240 |
| gcctcccacc | gtatcctggt | ggggcctcag | aggcttcaag | tgctaaacgc | cacccatgag | 300 |
| gatgctgggg | tctacagctg | ccagcagcgg | ctaaccccggc | gtgtgctgtg | ccactttagt | 360 |
| gtgcgtgtaa | cagatgctcc | gtcctcagga | gatgacgaag | atggggagga | cgtggctgaa | 420 |
| gacacagggg | ctccttactg | gactcgaccg | gagcgtatgg | ataagaaact | gctggctgtg | 480 |
| ccagctgcaa | acactgtacg | cttccgctgc | ccagctgctg | gcaaccccac | ccctccatc | 540 |
| ccctggctga | gaacggcaa | agaattccga | ggggagcacc | gcattggggg | cattaagctc | 600 |
| cggcaccagc | agtggagctt | ggtcatgaa | agtgtggtgc | cctctgaccg | cggcaattac | 660 |
| acctgcgtgg | ttgagaacaa | gtttggcagc | atccggcaga | cgtacaccct | ggatgtgctg | 720 |
| gagcgctccc | cacaccggcc | catcctgcag | gctgggctgc | cagccaacca | gacagccgtt | 780 |
| ctgggcagtg | acgtggagtt | ccactgcaag | gtgtacagcg | acgcacagcc | acacatccag | 840 |
| tggctgaagc | acgtggaggt | gaatgggagc | aaggtgggcc | ctgacggcac | gccctacgtc | 900 |
| actgtactca | agactgcagg | agctaacacc | accgacaggg | agctagaggt | tctgtccttg | 960 |
| cacaatgtca | cctttgagga | tgcgggggag | tacacctgcc | tggcgggcaa | ttctatcggg | 1020 |
| ttttcccatc | actctgcgtg | gctggtggtg | ctgccagccg | aggaggagct | gatggaagtt | 1080 |
| gacgaggctg | gcagcgtgta | cgcgggtgtc | ctcagctacg | ggtgtggctt | cttcctcttc | 1140 |
| atcctggtgg | tggcggcagt | gacgctctgc | cgtctgcgca | gtccccaaa | gaagggcctg | 1200 |
| ggctcgccca | ccgtgcacaa | ggtctctcgc | ttcccgctta | gcgacaggt | gtccttggag | 1260 |
| tctaattcct | ctatgaactc | caacacacct | ctcgtccgga | ttgcccggct | gtcctcagga | 1320 |
| gaaggtcctg | tcctggccaa | tgtttctgaa | cttgagctgc | ctgctgaccc | caagtgggag | 1380 |
| ctatccagga | cccggctgac | actcggtaag | cctcttggag | aaggctgctt | tggacaggtt | 1440 |
| gtcatggcag | aagctattgg | catcgacaag | accgcactg | ccaagcctgt | caccgtggcc | 1500 |
| gtgaagatgc | tgaaagatga | tgcgactgac | aaggacctgt | cggacctggt | gtctgagatg | 1560 |
| gagatgatga | aaatgattgg | caagcacaag | aacatcatta | acctgttggg | ggcctgcacc | 1620 |
| cagggtgggc | ccctgtatgt | gctggtggag | tatgcagcca | agggcaacct | gcgagagttc | 1680 |
| ctccggggcac | ggcggcctcc | aggcatggat | tactcctttg | atgcctgcag | gctgccagag | 1740 |
| gaacagctca | cctgcaagga | tctggtgtcc | tgtgcctacc | aggtggcacg | gggcatggag | 1800 |
| tacttggctt | cccagaagtg | tattcacaga | gacctggctg | ccagaaacgt | gctggtgact | 1860 |
| gaggacaatg | tgatgaagat | tgcagacttt | ggcctggccc | gagatgtgca | caacctggat | 1920 |

-continued

```
tactacaaga agaccacaaa tggccggcta cctgtgaagt ggatggcacc agaggccctt     1980
tttgaccgag tctacaccca tcagagtgat gtctggtcct tggtgtcct cctctgggag      2040 atctttacac tgggtgggtc accatatcct ggcatcccag tggaagagct tttcaagctg     2100
ttgaaagagg gccaccgcat ggacaagcca gccaactgca cacatgacct gtacatgatc     2160
atgcgggaat gttggcatgc agtgccttca cagaggccca ccttcaagca gttggtagag     2220
gatttagacc gcatcctcac ggtgacatca actgacgagt acttggacct ctcggtgcca     2280
tttgaacagt actcgccagg tggccaagat actcctagct ccagctcgtc cggggacgac     2340
tctgtgttca cccatgacct gctacccca ggcccaccca gcaatggggg acctcggacg      2400
tga                                                                   2403
```

<210> SEQ ID NO 18
<211> LENGTH: 800
<212> TYPE: PRT
<213> ORGANISM: Rattus norvegicus FGFR3IIIc

<400> SEQUENCE: 18

```
Met Val Val Pro Ala Cys Val Leu Val Phe Cys Val Ala Val Val Ala
1               5                   10                  15

Gly Val Thr Ser Glu Pro Pro Gly Pro Glu Gln Arg Val Gly Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Leu Trp Ala Lys Asp Gly Val Gly Leu Val
65                  70                  75                  80

Ala Ser His Arg Ile Leu Val Gly Pro Gln Arg Leu Gln Val Leu Asn
                85                  90                  95

Ala Thr His Glu Asp Ala Gly Val Tyr Ser Cys Gln Gln Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Pro Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Val Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285
```

-continued

```
Gly Ser Lys Val Gly Pro Asp Gly Thr Pro Tyr Val Thr Val Leu Lys
    290                 295                 300

Thr Ala Gly Ala Asn Thr Thr Asp Arg Glu Leu Glu Val Leu Ser Leu
305                 310                 315                 320

His Asn Val Thr Phe Glu Asp Ala Gly Glu Tyr Thr Cys Leu Ala Gly
                325                 330                 335

Asn Ser Ile Gly Phe Ser His His Ser Ala Trp Leu Val Val Leu Pro
                340                 345                 350

Ala Glu Glu Glu Leu Met Glu Val Asp Glu Ala Gly Ser Val Tyr Ala
                355                 360                 365

Gly Val Leu Ser Tyr Gly Val Gly Phe Phe Leu Phe Ile Leu Val Val
    370                 375                 380

Ala Ala Val Thr Leu Cys Arg Leu Arg Ser Pro Lys Lys Gly Leu
385                 390                 395                 400

Gly Ser Pro Thr Val His Lys Val Ser Arg Phe Pro Leu Lys Arg Gln
                405                 410                 415

Val Ser Leu Glu Ser Asn Ser Ser Met Asn Ser Asn Thr Pro Leu Val
                420                 425                 430

Arg Ile Ala Arg Leu Ser Ser Gly Glu Gly Pro Val Leu Ala Asn Val
                435                 440                 445

Ser Glu Leu Glu Leu Pro Ala Asp Pro Lys Trp Glu Leu Ser Arg Thr
    450                 455                 460

Arg Leu Thr Leu Gly Lys Pro Leu Gly Glu Gly Cys Phe Gly Gln Val
465                 470                 475                 480

Val Met Ala Glu Ala Ile Gly Ile Asp Lys Asp Arg Thr Ala Lys Pro
                485                 490                 495

Val Thr Val Ala Val Lys Met Leu Lys Asp Asp Ala Thr Asp Lys Asp
                500                 505                 510

Leu Ser Asp Leu Val Ser Glu Met Glu Met Met Lys Met Ile Gly Lys
                515                 520                 525

His Lys Asn Ile Ile Asn Leu Leu Gly Ala Cys Thr Gln Gly Gly Pro
    530                 535                 540

Leu Tyr Val Leu Val Glu Tyr Ala Ala Lys Gly Asn Leu Arg Glu Phe
545                 550                 555                 560

Leu Arg Ala Arg Arg Pro Pro Gly Met Asp Tyr Ser Phe Asp Ala Cys
                565                 570                 575

Arg Leu Pro Glu Glu Gln Leu Thr Cys Lys Asp Leu Val Ser Cys Ala
                580                 585                 590

Tyr Gln Val Ala Arg Gly Met Glu Tyr Leu Ala Ser Gln Lys Cys Ile
                595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Gln Ser Asp Val Trp
                660                 665                 670

Ser Phe Gly Val Leu Leu Trp Glu Ile Phe Thr Leu Gly Gly Ser Pro
                675                 680                 685

Tyr Pro Gly Ile Pro Val Glu Glu Leu Phe Lys Leu Leu Lys Glu Gly
    690                 695                 700
```

```
His Arg Met Asp Lys Pro Ala Asn Cys Thr His Asp Leu Tyr Met Ile
705                 710                 715                 720

Met Arg Glu Cys Trp His Ala Val Pro Ser Gln Arg Pro Thr Phe Lys
            725                 730                 735

Gln Leu Val Glu Asp Leu Asp Arg Ile Leu Thr Val Ser Thr Asp
        740                 745                 750

Glu Tyr Leu Asp Leu Ser Val Pro Phe Glu Gln Tyr Ser Pro Gly Gly
    755                 760                 765

Gln Asp Thr Pro Ser Ser Ser Ser Ser Gly Asp Ser Val Phe Thr
    770                 775                 780

His Asp Leu Leu Pro Pro Gly Pro Pro Ser Asn Gly Gly Pro Arg Thr
785                 790                 795                 800

<210> SEQ ID NO 19
<211> LENGTH: 2421
<212> TYPE: DNA
<213> ORGANISM: Gallus gallus FGFR3

<400> SEQUENCE: 19
atgcgggcgg cctggggctc cgtctggtgc ctgtgcctgg cggcggccgt cggagcgctg      60
ccggcggcgc gccggcgcgg agcggagcgg agcggcgggc aggcggcaga atacttgagg     120
agcgagaccg cctttctgga agagttggtg tttggaagtg agataccat tgaactttcc      180 tgtaacaccc agagctcttc tgtgtcagtt ttctggttta agatggtat tgggattgca      240 ccttccaaca gaactcatat tggacaaaaa ctgttgaaga taatcaatgt gtcatatgac      300
gattcggggc tgtacagttg caagccaagg cattccaacg aggtcctggg aaactttaca      360
gtcagagtga cagattcccc ttcgtcaggt gatgatgaag atgatgacga tgagtcagag      420
gatacaggtg tccccttctg gacccggcca gataagatgg aagaagct gctggcagtt       480 cctgccgcca acaccgttcg cttccgatgt ccagcaggtg aaacccaac tccaccatt       540 tactggctga agaatggcaa agaattcaag ggagagcaca ggatcggggg catcaagttg      600
cgacaccagc agtggagctt ggtgatggag agcgttgtgc cgtcagatcg aggaaactac      660
acctgtgttg tggagaacaa atatggcaat attaggcaca tatccagct tgatgtttta      720 gaacggtcac cccaccgacc aatcctgcaa gcaggactcc ctgccaatca gactgtggtg      780
gtcgggagca atgtggaatt tcactgcaag gtctacagcg atgcccagcc tcatatccag      840
tggctgaaaa cgtagaagt caacggcagc aagtatggac ctgatgggac accctatgtc      900
acagtgctga gacggcagg tgttaacaca acgataagg agctagagat tctgtacttg      960
cgaaatgtta cttttgagga tgctggggaa tatacttgtc tcgcagggaa ttctattggg     1020
ttctcacatc actctgcttg gctgacggtg ctaccagcag aggagctgat ggaaatggat     1080
gattcgggct cagtgtacgc tggcattctc agctatggca ctggcttagt cctcttcatc     1140
ctggtgctgg tcattgtgat tatctgcagg atgaaaatgc aaacaaaaa ggccatgaac     1200 accaccactg tacagaaagt ctccaaattt ccactcaaga gacagcaggt gtcgttggag     1260
tccaactctt ccatgaattc caacacaccc ctggtccgga tcactcgtct ctcctccagc     1320
gatgggccga tgctggccaa cgtctctgag ctggaacttc ctccagatcc caagtgggaa     1380
ttggcacgtt ctcgcctgac cctggggaag ccgcttggtg agggctgttt tggccaagtg     1440
gtgatggcgg aagcaattgg gattgataaa gacaagccaa acaaggccat caccgtggct     1500
gtcaagatgt taaagatga tgccacagac aaggaccttt cagacctggt ctctgagatg     1560
gaaatgatga aaatgattgg gaagcacaaa aacatcatta acctgctcgg tgcttgcacg     1620
```

-continued

```
caggacggac cgctctacgt gttggttgaa tatgcatcga aggggaactt gcgggaatac    1680
ctcagggcac gtcgcccacc tggcatggac tattccttcg acacctgcaa gctgcccgag    1740
gagcagttga catttaaaga cctggttttc tgcgcctacc aggtggcccg ggcatggag     1800 tacttggcgt cacagaaatg cattcatcgt gacttggcag ccaggaatgt gttagtcact    1860
gaggacaatg tgatgaaaat agctgatttt ggccttgcta gagacgttca acatcgac     1920 tattacaaga aaaccaccaa tggtcggctg cctgtgaaat ggatggctcc agaagcattg    1980
tttgaccggg tctatactca ccagagcgat gtctggtctt ttggagtgct actatgggag    2040
atcttcactt tgggagggtc tccgtacccg ggaattcctg ttgaagaact cttcaaactc    2100
ttgaaagaag gccatcggat ggataaaccc gccaactgta cccacgacct gtacatgatc    2160
atgcgggagt gctggcacgc tgtcccctcg cagcgaccca cattcaagca gctggtggaa    2220
gacctggaca gagtcctcac catgacatcc actgatgagt acctggacct ctcggtgccc    2280
tttgagcaat actcacccgc tggccaggac acccacagca cctgctcctc aggggacgac    2340
tcggtttttg cacatgacct gctgcctgat gagccctgcc tgcccaagca cgtgccctgt    2400
aatggcgtca tccgcacgtg a                                              2421
```

<210> SEQ ID NO 20
<211> LENGTH: 806
<212> TYPE: PRT
<213> ORGANISM: Gallus gallus FGFR3

<400> SEQUENCE: 20

```
Met Arg Ala Ala Trp Gly Ser Val Trp Cys Leu Cys Leu Ala Ala
 1               5                  10                  15

Val Gly Ala Leu Pro Ala Ala Arg Arg Gly Ala Glu Arg Ser Gly
                20                  25                  30

Gly Gln Ala Ala Glu Tyr Leu Arg Ser Glu Thr Ala Phe Leu Glu
                35                  40                  45

Leu Val Phe Gly Ser Gly Asp Thr Ile Glu Leu Ser Cys Asn Thr Gln
        50                  55                  60

Ser Ser Ser Val Ser Val Phe Trp Phe Lys Asp Gly Ile Gly Ile Ala
65                  70                  75                  80

Pro Ser Asn Arg Thr His Ile Gly Gln Lys Leu Leu Lys Ile Ile Asn
                85                  90                  95

Val Ser Tyr Asp Asp Ser Gly Leu Tyr Ser Cys Lys Pro Arg His Ser
                100                 105                 110

Asn Glu Val Leu Gly Asn Phe Thr Val Arg Val Thr Asp Ser Pro Ser
            115                 120                 125

Ser Gly Asp Asp Glu Asp Asp Asp Glu Ser Glu Asp Thr Gly Val
            130                 135                 140

Pro Phe Trp Thr Arg Pro Asp Lys Met Glu Lys Lys Leu Leu Ala Val
145                 150                 155                 160

Pro Ala Ala Asn Thr Val Arg Phe Arg Cys Pro Ala Gly Gly Asn Pro
                165                 170                 175

Thr Pro Thr Ile Tyr Trp Leu Lys Asn Gly Lys Glu Phe Lys Gly Glu
                180                 185                 190

His Arg Ile Gly Gly Ile Lys Leu Arg His Gln Gln Trp Ser Leu Val
            195                 200                 205

Met Glu Ser Val Val Pro Ser Asp Arg Gly Asn Tyr Thr Cys Val Val
    210                 215                 220
```

-continued

```
Glu Asn Lys Tyr Gly Asn Ile Arg His Thr Tyr Gln Leu Asp Val Leu
225                 230                 235                 240

Glu Arg Ser Pro His Arg Pro Ile Leu Gln Ala Gly Leu Pro Ala Asn
                245                 250                 255

Gln Thr Val Val Val Gly Ser Asn Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Tyr Gly Pro Asp Gly Thr Pro Tyr Val Thr Val Leu Lys
    290                 295                 300

Thr Ala Gly Val Asn Thr Thr Asp Lys Glu Leu Glu Ile Leu Tyr Leu
305                 310                 315                 320

Arg Asn Val Thr Phe Glu Asp Ala Gly Glu Tyr Thr Cys Leu Ala Gly
                325                 330                 335

Asn Ser Ile Gly Phe Ser His His Ser Ala Trp Leu Thr Val Leu Pro
                340                 345                 350

Ala Glu Glu Leu Met Glu Met Asp Asp Ser Gly Ser Val Tyr Ala Gly
            355                 360                 365

Ile Leu Ser Tyr Gly Thr Gly Leu Val Leu Phe Ile Leu Val Leu Val
    370                 375                 380

Ile Val Ile Ile Cys Arg Met Lys Met Pro Asn Lys Lys Ala Met Asn
385                 390                 395                 400

Thr Thr Thr Val Gln Lys Val Ser Lys Phe Pro Leu Lys Arg Gln Gln
                405                 410                 415

Val Ser Leu Glu Ser Asn Ser Ser Met Asn Ser Asn Thr Pro Leu Val
            420                 425                 430

Arg Ile Thr Arg Leu Ser Ser Ser Asp Gly Pro Met Leu Ala Asn Val
                435                 440                 445

Ser Glu Leu Glu Leu Pro Pro Asp Pro Lys Trp Glu Leu Ala Arg Ser
    450                 455                 460

Arg Leu Thr Leu Gly Lys Pro Leu Gly Glu Gly Cys Phe Gly Gln Val
465                 470                 475                 480

Val Met Ala Glu Ala Ile Gly Ile Asp Lys Asp Lys Pro Asn Lys Ala
                485                 490                 495

Ile Thr Val Ala Val Lys Met Leu Lys Asp Asp Ala Thr Asp Lys Asp
                500                 505                 510

Leu Ser Asp Leu Val Ser Glu Met Glu Met Met Lys Met Ile Gly Lys
    515                 520                 525

His Lys Asn Ile Ile Asn Leu Leu Gly Ala Cys Thr Gln Asp Gly Pro
    530                 535                 540

Leu Tyr Val Leu Val Glu Tyr Ala Ser Lys Gly Asn Leu Arg Glu Tyr
545                 550                 555                 560

Leu Arg Ala Arg Arg Pro Pro Gly Met Asp Tyr Ser Phe Asp Thr Cys
                565                 570                 575

Lys Leu Pro Glu Glu Gln Leu Thr Phe Lys Asp Leu Val Ser Cys Ala
            580                 585                 590

Tyr Gln Val Ala Arg Gly Met Glu Tyr Leu Ala Ser Gln Lys Cys Ile
        595                 600                 605

His Arg Asp Leu Ala Ala Arg Asn Val Leu Val Thr Glu Asp Asn Val
    610                 615                 620

Met Lys Ile Ala Asp Phe Gly Leu Ala Arg Asp Val His Asn Ile Asp
625                 630                 635                 640

Tyr Tyr Lys Lys Thr Thr Asn Gly Arg Leu Pro Val Lys Trp Met Ala
```

-continued

```
                   645                 650                 655
Pro Glu Ala Leu Phe Asp Arg Val Tyr Thr His Gln Ser Asp Val Trp
                660                 665                 670
Ser Phe Gly Val Leu Leu Trp Glu Ile Phe Thr Leu Gly Gly Ser Pro
            675                 680                 685
Tyr Pro Gly Ile Pro Val Glu Glu Leu Phe Lys Leu Leu Lys Glu Gly
        690                 695                 700
His Arg Met Asp Lys Pro Ala Asn Cys Thr His Asp Leu Tyr Met Ile
705                 710                 715                 720
Met Arg Glu Cys Trp His Ala Val Pro Ser Gln Arg Pro Thr Phe Lys
                725                 730                 735
Gln Leu Val Glu Asp Leu Asp Arg Val Leu Thr Met Thr Ser Thr Asp
            740                 745                 750
Glu Tyr Leu Asp Leu Ser Val Pro Phe Glu Gln Tyr Ser Pro Ala Gly
        755                 760                 765
Gln Asp Thr His Ser Thr Cys Ser Ser Gly Asp Asp Ser Val Phe Ala
    770                 775                 780
His Asp Leu Leu Pro Asp Glu Pro Cys Leu Pro Lys His Val Pro Cys
785                 790                 795                 800
Asn Gly Val Ile Arg Thr
                805
```

<210> SEQ ID NO 21
<211> LENGTH: 2484
<212> TYPE: DNA
<213> ORGANISM: Xenopus laevis FGFR3-1

<400> SEQUENCE: 21

```
atgtctaagg ctggaggggg ctgtggaatt gcccttttatc aagggatcca tatgggaatt      60
gtcaccctgt tctgcactct ctgcttttttt ctggtctctg tgaactgtgt cccggctgcc     120
cgactgccag ttacgctccc tggagaggac agagcaaaca gaaaagcatc agattatctc     180
acggtagaac agcccccatt cgatgagctc atgtttacaa ttggagaaac cattgagttg     240
tcctgctctg cggatgatgc atccacgacc accaagtggt tcaaggatgg tatcggcatt     300
gtgccgaaca cagaacaag tacgaggcag ggcctgctga agattatcaa catctcatac     360
gatgactctg ggatatacag ttgcagacta tggcattcta ctgaaattct gcgcaatttt     420
accatcagag taacagactt accatcgtcc ggtgatgatg aggatgacga tgatgaaacc     480
gaagacagag agcctcctcg ctggacccaa cctgagaaga tggagaagaa acttattgca     540
gtccctgccg ctaacacaat ccgattccgg tgcccagccg cggggaatcc caccctacc     600
atccattggc ttaagaacgg aaaggaattc aggggagagc atcgtattgg tggcatcaaa     660
ctccgacatc agcagtggag cctcgttatg gagagcgtag ttccatcgga taaaggcaac     720
tacacgtgtg tagtggagaa caaatatgga agcatccgtc aaacctatca acttgatgtc     780
ctggagaggt cctctcaccg gcccatcctt caggccgggt acccgccaa ccagacggtg     840
gtgtttggga gcgacgtgga attccactgc aaagtctaca gtgacgcaca gccacatatt     900
cagtggctta acacgtgga agtgaatggc agcaagtacg gcccagacgg agatccttac     960
gtcacagtgc tgcaatctttt caccaatggc actgaagtcg attctacctt aagtctaaaa    1020
aatgtgaccg agaccatga aggacagtat gtgtgtagag ccaacaattt cataggagta    1080
gccgaggcat cctttttggct ccacatttac aaaccagcac cagcagaacc agtggagaag    1140
ccagcaacca catcttccag ctccatcacc gttcttattg tggtcacctc gactattgtg    1200
```

```
ttcatactgt tggttatcat tgtcatcacc taccgcatga aggtcccttc taagaaggca    1260
atgagcaccc cgccggtgca taaagtctcc aagttcccgc tcaagcggca ggtgtctcta    1320
gagtccaact cttctatgaa ttccacaccc cgctggtga ggatcactca cctgtcctcc    1380
agcgacggaa ccatgttggc taatgtgtcg gagctcggcc tgcccctgga tcccaagtgg    1440
gagttattga gatcaaggct gactttagga aagcccttg gagaaggctg ctttggtcaa    1500
gtagtgatgg cagaagcaat tggcattgat aaggaaaggc caaataagcc tgttactgta    1560
gctgtaaaga tgcttaaaga tgatgctaca gataaagatc tctccgatct ggtctcggag    1620
atggagatga tgaaaatgat tgggaagcac aaaaatatca tcaatctgct aggagcatgc    1680
actcaggatg gaccactgta cgttcttgtg aatatgcat ccaaagggaa cctcagggag    1740
tatttaaagg cacggcgccc cccaggaatg gattattctt ttgacacctg caaaattcca    1800
gctgagcagc tgacgttcaa ggacctcgtt tcttgcgcct accaggtagc tcgtggcatg    1860
gagtacctgg cgtcgcaaaa atgtattcac agagatctgg cagccagaaa tgtgttagta    1920
acagatgaca ttgtaatgaa gattgcagat ttcggcttgg ccaggacat ccacaacata    1980 gattattaca agaaaacaac aaatggtcgg ctgccagtca aatggatggc tccggaagct    2040
ttgttcgacc gtatctacac tcatcagagc gatgtatggt cgtacggagt gctgctgtgg    2100
gagatattta cactgggggg ctcgccctac ccagggatcc cagtagagga actctttaag    2160
ctattgaaag aaggcacag aatggacaag ccagcaaact gcacacatga actgtatatg    2220
atcatgagag agtgctggca cgctgtccca tcgcaaagac caaccttcaa gcagctggtt    2280
gaagaccttg accgcgttct tactgtaaca tctactgatg agtacctgga cctgtcggta    2340
ccattcgagc agtattcccc ggcgggccaa gacagtaaca gcacctgctc ctcgggggac    2400
gactcagtct ttgctcatga catttttaccc gatgaaccgt gtcttcccaa caacagcag    2460 tacaacggcg ccatccgaac atga                                           2484
```

<210> SEQ ID NO 22
<211> LENGTH: 827
<212> TYPE: PRT
<213> ORGANISM: Xenopus laevis FGFR3-1

<400> SEQUENCE: 22

```
Met Ser Lys Ala Gly Gly Cys Gly Ile Ala Leu Tyr Gln Gly Ile
 1               5                  10                  15

His Met Gly Ile Val Thr Leu Phe Cys Thr Leu Cys Phe Phe Leu Val
            20                  25                  30

Ser Val Asn Cys Val Pro Ala Ala Arg Leu Pro Val Thr Leu Pro Gly
        35                  40                  45

Glu Asp Arg Ala Asn Arg Lys Ala Ser Asp Tyr Leu Thr Val Glu Gln
    50                  55                  60

Pro Pro Phe Asp Glu Leu Met Phe Thr Ile Gly Glu Thr Ile Glu Leu
65                  70                  75                  80

Ser Cys Ser Ala Asp Asp Ala Ser Thr Thr Lys Trp Phe Lys Asp
                85                  90                  95

Gly Ile Gly Ile Val Pro Asn Asn Arg Thr Ser Thr Arg Gln Gly Leu
            100                 105                 110

Leu Lys Ile Ile Asn Ile Ser Tyr Asp Asp Ser Gly Ile Tyr Ser Cys
        115                 120                 125

Arg Leu Trp His Ser Thr Glu Ile Leu Arg Asn Phe Thr Ile Arg Val
    130                 135                 140
```

-continued

```
Thr Asp Leu Pro Ser Ser Gly Asp Asp Glu Asp Asp Asp Glu Thr
145                 150                 155                 160

Glu Asp Arg Glu Pro Pro Arg Trp Thr Gln Pro Glu Lys Met Glu Lys
                165                 170                 175

Lys Leu Ile Ala Val Pro Ala Ala Asn Thr Ile Arg Phe Arg Cys Pro
                180                 185                 190

Ala Ala Gly Asn Pro Thr Pro Thr Ile His Trp Leu Lys Asn Gly Lys
                195                 200                 205

Glu Phe Arg Gly Glu His Arg Ile Gly Gly Ile Lys Leu Arg His Gln
                210                 215                 220

Gln Trp Ser Leu Val Met Glu Ser Val Val Pro Ser Asp Lys Gly Asn
225                 230                 235                 240

Tyr Thr Cys Val Val Glu Asn Lys Tyr Gly Ser Ile Arg Gln Thr Tyr
                245                 250                 255

Gln Leu Asp Val Leu Glu Arg Ser Ser His Arg Pro Ile Leu Gln Ala
                260                 265                 270

Gly Leu Pro Ala Asn Gln Thr Val Val Phe Gly Ser Asp Val Glu Phe
                275                 280                 285

His Cys Lys Val Tyr Ser Asp Ala Gln Pro His Ile Gln Trp Leu Lys
                290                 295                 300

His Val Glu Val Asn Gly Ser Lys Tyr Gly Pro Asp Gly Asp Pro Tyr
305                 310                 315                 320

Val Thr Val Leu Gln Ser Phe Thr Asn Gly Thr Glu Val Asp Ser Thr
                325                 330                 335

Leu Ser Leu Lys Asn Val Thr Glu Thr His Glu Gly Gln Tyr Val Cys
                340                 345                 350

Arg Ala Asn Asn Phe Ile Gly Val Ala Glu Ala Ser Phe Trp Leu His
                355                 360                 365

Ile Tyr Lys Pro Ala Pro Ala Glu Pro Val Glu Lys Pro Ala Thr Thr
                370                 375                 380

Ser Ser Ser Ser Ile Thr Val Leu Ile Val Val Thr Ser Thr Ile Val
385                 390                 395                 400

Phe Ile Leu Leu Val Ile Ile Val Ile Thr Tyr Arg Met Lys Val Pro
                405                 410                 415

Ser Lys Lys Ala Met Ser Thr Pro Pro Val His Lys Val Ser Lys Phe
                420                 425                 430

Pro Leu Lys Arg Gln Val Ser Leu Glu Ser Asn Ser Ser Met Asn Ser
                435                 440                 445

Asn Thr Pro Leu Val Arg Ile Thr His Leu Ser Ser Ser Asp Gly Thr
                450                 455                 460

Met Leu Ala Asn Val Ser Glu Leu Gly Leu Pro Leu Asp Pro Lys Trp
465                 470                 475                 480

Glu Leu Leu Arg Ser Arg Leu Thr Leu Gly Lys Pro Leu Gly Glu Gly
                485                 490                 495

Cys Phe Gly Gln Val Val Met Ala Glu Ala Ile Gly Ile Asp Lys Glu
                500                 505                 510

Arg Pro Asn Lys Pro Val Thr Val Ala Val Lys Met Leu Lys Asp Asp
                515                 520                 525

Ala Thr Asp Lys Asp Leu Ser Asp Leu Val Ser Glu Met Glu Met Met
                530                 535                 540

Lys Met Ile Gly Lys His Lys Asn Ile Ile Asn Leu Leu Gly Ala Cys
545                 550                 555                 560
```

```
Thr Gln Asp Gly Pro Leu Tyr Val Leu Val Glu Tyr Ala Ser Lys Gly
                565                 570                 575
Asn Leu Arg Glu Tyr Leu Lys Ala Arg Arg Pro Gly Met Asp Tyr
            580                 585                 590
Ser Phe Asp Thr Cys Lys Ile Pro Ala Glu Gln Leu Thr Phe Lys Asp
        595                 600                 605
Leu Val Ser Cys Ala Tyr Gln Val Ala Arg Gly Met Glu Tyr Leu Ala
    610                 615                 620
Ser Gln Lys Cys Ile His Arg Asp Leu Ala Ala Arg Asn Val Leu Val
625                 630                 635                 640
Thr Asp Asp Ile Val Met Lys Ile Ala Asp Phe Gly Leu Ala Arg Asp
                645                 650                 655
Ile His Asn Ile Asp Tyr Tyr Lys Lys Thr Thr Asn Gly Arg Leu Pro
            660                 665                 670
Val Lys Trp Met Ala Pro Glu Ala Leu Phe Asp Arg Ile Tyr Thr His
        675                 680                 685
Gln Ser Asp Val Trp Ser Tyr Gly Val Leu Leu Trp Glu Ile Phe Thr
    690                 695                 700
Leu Gly Gly Ser Pro Tyr Pro Gly Ile Pro Val Glu Glu Leu Phe Lys
705                 710                 715                 720
Leu Leu Lys Glu Gly His Arg Met Asp Lys Pro Ala Asn Cys Thr His
                725                 730                 735
Glu Leu Tyr Met Ile Met Arg Glu Cys Trp His Ala Val Pro Ser Gln
            740                 745                 750
Arg Pro Thr Phe Lys Gln Leu Val Glu Asp Leu Asp Arg Val Leu Thr
        755                 760                 765
Val Thr Ser Thr Asp Glu Tyr Leu Asp Leu Ser Val Pro Phe Glu Gln
    770                 775                 780
Tyr Ser Pro Ala Gly Gln Asp Ser Asn Ser Thr Cys Ser Ser Gly Asp
785                 790                 795                 800
Asp Ser Val Phe Ala His Asp Ile Leu Pro Asp Glu Pro Cys Leu Pro
                805                 810                 815
Lys Gln Gln Gln Tyr Asn Gly Ala Ile Arg Thr
            820                 825

<210> SEQ ID NO 23
<211> LENGTH: 2409
<212> TYPE: DNA
<213> ORGANISM: Xenopus laevis FGFR3-2

<400> SEQUENCE: 23
atggtctctg tgaatggtgt cccggctgcc cgactgccag ttacgctccc tggagaggac      60
agagcgagca gaaaagcacc agattatctc atggtagaac agcccccatt cgatgaactc     120
atgtatacaa ttggagaaac cattgagttg tcctgcgctg cagaagatgc ttccacaact     180
accaagtggt gtaaggatgg tattggcatt gtaccgaaca acagaacaag cacaaggcag     240
ggcctgctga agattatcaa cgtctcctcc gatgactccg ggatatacag ctgcagacta     300
tggcattcta ccgagattct cgcaattttt acaatcagag taacagactt gccatcatct     360
ggtgacgatg aggatgatga tgatgatgat gatgatgaaa ccgaagacag agaacctcct     420
cgctggaccc aacctgagag gatggaaaag aaacttattg cagtccctgc tgctaacaca     480
atccgcttcc ggtgcccagc cgcagggaat cccaccccta ccatccactg gctaaagaac     540
ggaaaggagt tcagggggga acatcgtatt ggtggcatca aactccgaca tcaacagtgg     600
```

-continued

```
agccttgtta tggagagtgt ggtcccatca gataaaggca actacacgtg tgtggtggag    660
aacaaatatg gaagcatccg tcaaacctat caacttgatg tccttgagag gtcctctcac    720
cggcccatcc ttcaggctgg gttacccggc aaccagacgg ttgtgcttgg gagcgacgtg    780
gaattccact gcaaagtcta cagtgacgca aacctcata ttcagtggct aaacacgtg     840
gaagtgaatg cagcaaaata cggcccagac ggagatcctt acgtctcagt gttgcaatct    900
ttcatcaatg gcactgaagt cgattctacc ctaagtctaa aaaatgtgac cgagaccaat    960
gaaggacagt atgtgtgtag agccaacaat ttcataggag tagccgaggc atccttttgg   1020
ctccacattt acaaaccagc accagcagaa ccagtggaga aggcattgac aacatcttcc   1080
agctctatca ccgtccttat tgtggtcacc tcgaccattg tgttcatact gttggttatc   1140
atcgtcatca cccacctcat gaaggtccct tccaagaagt caatgaccgc ccaccggtg    1200
cataaagtct ccaagttccc cctcaaacgg cagcaggtgt ctctagagtc caactcttct   1260
atgaattcca cacccgtt ggtgaggatc actcatctgt cctccagcga tggaaccatg     1320
ctggctaatg tgtcggaact tggcctgcca cttgacccca gtgggagtt attgagatca   1380
aggctgactt taggaaagcc cctcggggaa ggctgcttcg gtcaggtggt gatggcagaa   1440
gctattggca ttgataagga aaggccaaat aagcctgcta ctgtagctgt aaagatgctt   1500
aaagacgatg ccacagataa agatctctca gatctggtct ctgagatgga gatgatgaaa   1560
atgattggga agcataaaaa tatcatcaat ctgctgggag catgcactca ggatgggccg   1620
ctgtacgttc tggtggaata cgcatcgaaa gggagcctca gggagtattt aaaggcacgg   1680
cgccccccag gaatggatta ttcttttgat gcctgcaaaa ttccagctga gcagctgacg   1740
ttcaaggacc tagtttcttg tgcctaccag gtagctcgtg gcatggagta cctggcatca   1800
caaaaatgca ttcacagaga tctggcagcc agaaatgtgt tagtaacaga tgacaacgta   1860
atgaagattg cagatttcgg cttggccagg gacatccaca acatagatta ttacaagaaa   1920
acaacaaatg gtcggctgcc tgtgaaatgg atggctccgg aagctttgtt tgaccgtatc   1980
tacactcatc acagcgatgt atggtcgtac ggagtgctgc tgtgggagat atttacactg   2040
ggggctcac cctacccagg gatcccggta gaggaacttt ttaagctatt gaagaaggc     2100
cacagaatgg acaagccagc aaactgcaca catgaactgt atatgatcat gagagagtgc   2160
tggcacgctg tccctcaca aagacccgcc ttcaagcagc tggttgaaga ccttgaccgc    2220
gttcttactg taacatctac taatgagtac ctagacctct cggtagcatt cgagcagtat   2280
tctccaccca gccaagacag tcacagcacc tgctcctcag gggacgactc agtctttgct   2340
cacgacattt acccgatga accgtgtctt cccaaacacc agcagcacaa cggcgccatc    2400
cccacatga                                                          2409
```

<210> SEQ ID NO 24
<211> LENGTH: 802
<212> TYPE: PRT
<213> ORGANISM: Xenopus laevis FGFR3-2

<400> SEQUENCE: 24

Met Val Ser Val Asn Gly Val Pro Ala Ala Arg Leu Pro Val Thr Leu
1               5                   10                  15

Pro Gly Glu Asp Arg Ala Ser Arg Lys Ala Pro Asp Tyr Leu Met Val
            20                  25                  30

Glu Gln Pro Pro Phe Asp Glu Leu Met Tyr Thr Ile Gly Glu Thr Ile
        35                  40                  45

-continued

```
Glu Leu Ser Cys Ala Ala Glu Asp Ala Ser Thr Thr Thr Lys Trp Cys
 50                  55                  60

Lys Asp Gly Ile Gly Ile Val Pro Asn Asn Arg Thr Ser Thr Arg Gln
 65                  70                  75                  80

Gly Leu Leu Lys Ile Ile Asn Val Ser Ser Asp Ser Gly Ile Tyr
                 85                  90                  95

Ser Cys Arg Leu Trp His Ser Thr Glu Ile Leu Arg Asn Phe Thr Ile
            100                 105                 110

Arg Val Thr Asp Leu Pro Ser Ser Gly Asp Asp Glu Asp Asp Asp Asp
            115                 120                 125

Asp Asp Asp Glu Thr Glu Asp Arg Glu Pro Pro Arg Trp Thr Gln
130                 135                 140

Pro Glu Arg Met Glu Lys Lys Leu Ile Ala Val Pro Ala Ala Asn Thr
145                 150                 155                 160

Ile Arg Phe Arg Cys Pro Ala Ala Gly Asn Pro Thr Pro Thr Ile His
                    165                 170                 175

Trp Leu Lys Asn Gly Lys Glu Phe Arg Gly Glu His Arg Ile Gly Gly
                180                 185                 190

Ile Lys Leu Arg His Gln Gln Trp Ser Leu Val Met Glu Ser Val Val
            195                 200                 205

Pro Ser Asp Lys Gly Asn Tyr Thr Cys Val Val Glu Asn Lys Tyr Gly
210                 215                 220

Ser Ile Arg Gln Thr Tyr Gln Leu Asp Val Leu Glu Arg Ser Ser His
225                 230                 235                 240

Arg Pro Ile Leu Gln Ala Gly Leu Pro Gly Asn Gln Thr Val Val Leu
                    245                 250                 255

Gly Ser Asp Val Glu Phe His Cys Lys Val Tyr Ser Asp Ala Gln Pro
                260                 265                 270

His Ile Gln Trp Leu Lys His Val Glu Val Asn Gly Ser Lys Tyr Gly
            275                 280                 285

Pro Asp Gly Asp Pro Tyr Val Ser Val Leu Gln Ser Phe Ile Asn Gly
290                 295                 300

Thr Glu Val Asp Ser Thr Leu Ser Leu Lys Asn Val Thr Glu Thr Asn
305                 310                 315                 320

Glu Gly Gln Tyr Val Cys Arg Ala Asn Asn Phe Ile Gly Val Ala Glu
                    325                 330                 335

Ala Ser Phe Trp Leu His Ile Tyr Lys Pro Ala Pro Ala Glu Pro Val
                340                 345                 350

Glu Lys Ala Leu Thr Thr Ser Ser Ser Ile Thr Val Leu Ile Val
            355                 360                 365

Val Thr Ser Thr Ile Val Phe Ile Leu Leu Val Ile Ile Val Ile Thr
            370                 375                 380

His Leu Met Lys Val Pro Ser Lys Lys Ser Met Thr Ala Pro Pro Val
385                 390                 395                 400

His Lys Val Ser Lys Phe Pro Leu Lys Arg Gln Val Ser Leu Glu
                    405                 410                 415

Ser Asn Ser Ser Met Asn Ser Asn Thr Pro Leu Val Arg Ile Thr His
                420                 425                 430

Leu Ser Ser Ser Asp Gly Thr Met Leu Ala Asn Val Ser Glu Leu Gly
            435                 440                 445

Leu Pro Leu Asp Pro Lys Trp Glu Leu Leu Arg Ser Arg Leu Thr Leu
450                 455                 460

Gly Lys Pro Leu Gly Glu Gly Cys Phe Gly Gln Val Val Met Ala Glu
```

```
                465                 470                 475                 480
Ala Ile Gly Ile Asp Lys Glu Arg Pro Asn Lys Pro Ala Thr Val Ala
                    485                 490                 495
Val Lys Met Leu Lys Asp Asp Ala Thr Asp Lys Asp Leu Ser Asp Leu
                500                 505                 510
Val Ser Glu Met Glu Met Met Lys Met Ile Gly Lys His Lys Asn Ile
                515                 520                 525
Ile Asn Leu Leu Gly Ala Cys Thr Gln Asp Gly Pro Leu Tyr Val Leu
                530                 535                 540
Val Glu Tyr Ala Ser Lys Gly Ser Leu Arg Glu Tyr Leu Lys Ala Arg
545                 550                 555                 560
Arg Pro Pro Gly Met Asp Tyr Ser Phe Asp Ala Cys Lys Ile Pro Ala
                    565                 570                 575
Glu Gln Leu Thr Phe Lys Asp Leu Val Ser Cys Ala Tyr Gln Val Ala
                580                 585                 590
Arg Gly Met Glu Tyr Leu Ala Ser Gln Lys Cys Ile His Arg Asp Leu
                595                 600                 605
Ala Ala Arg Asn Val Leu Val Thr Asp Asp Asn Val Met Lys Ile Ala
                610                 615                 620
Asp Phe Gly Leu Ala Arg Asp Ile His Asn Ile Asp Tyr Tyr Lys Lys
625                 630                 635                 640
Thr Thr Asn Gly Arg Leu Pro Val Lys Trp Met Ala Pro Glu Ala Leu
                    645                 650                 655
Phe Asp Arg Ile Tyr Thr His His Ser Asp Val Trp Ser Tyr Gly Val
                660                 665                 670
Leu Leu Trp Glu Ile Phe Thr Leu Gly Gly Ser Pro Tyr Pro Gly Ile
                675                 680                 685
Pro Val Glu Glu Leu Phe Lys Leu Leu Lys Glu Gly His Arg Met Asp
                690                 695                 700
Lys Pro Ala Asn Cys Thr His Glu Leu Tyr Met Ile Met Arg Glu Cys
705                 710                 715                 720
Trp His Ala Val Pro Ser Gln Arg Pro Ala Phe Lys Gln Leu Val Glu
                    725                 730                 735
Asp Leu Asp Arg Val Leu Thr Val Thr Ser Thr Asn Glu Tyr Leu Asp
                740                 745                 750
Leu Ser Val Ala Phe Glu Gln Tyr Ser Pro Pro Ser Gln Asp Ser His
                755                 760                 765
Ser Thr Cys Ser Ser Gly Asp Asp Ser Val Phe Ala His Asp Ile Leu
                770                 775                 780
Pro Asp Glu Pro Cys Leu Pro Lys His Gln Gln His Asn Gly Ala Ile
785                 790                 795                 800
Pro Thr

<210> SEQ ID NO 25
<211> LENGTH: 2391
<212> TYPE: DNA
<213> ORGANISM: Pleurodeles waltlii FGFR3

<400> SEQUENCE: 25
atgctcgtct ggctctgcgg cttgtgtctg gtgactctgg cgggcggacg ttcggcggcc      60
aggctgcccc tcaccgaggg ccgacccaca gcagacttcc tgcccggcga cgcctccctg     120
gtggaagagc tcctgttcgg cacgggggac accatcgagc tcctcctgca caccccgggc     180
tcctctgtgt ccgtggtgtg gttcaaagac gggatctcgg tggacccacc aacctggtcc     240
```

-continued

| | |
|---|---|
| cacaccggcc agaagctgct gaagatcatc aacgtgtcct acgacgactc gggagtgtac | 300 |
| agctgcaagg cccggcagtc cagcgaggtg ctccggaacg tgaccgtcag ggtgaccgat | 360 |
| tctccgtcat ccggtgatga cgaagatgat gatgaggaat ctgaaagtgc aaatgcacca | 420 |
| aaattcacgc gaccggaatg gatggagaag aaactgcttg cagtgcccgc agccaacacg | 480 |
| gtgcgcttcc gatgcccagc tgcaggaaag ccaacgccat ccatcacttg gctgaaaaac | 540 |
| ggcaaggagt tcaaaggcga gcatcggatt gggggcataa agctaagaca ccagcagtgg | 600 |
| agtttggtga tggagagtgt agtcccatcc gatcggggaa attacacatg tgtggtggca | 660 |
| aacaagtacg gcaccatccg agagacctac acattggatg tccttgaacg aactcctcac | 720 |
| cggcccatcc tccaggcggg attccgttcc aacaagactg tggtggtagg aagcgatgtg | 780 |
| gagttccatt gcaaggtata cagtgatgct cagccgcaca tccagtggct gaaacacgtg | 840 |
| gaggttaatg gcagcaagtt tggacctgat gggaacccgt atgtcacagt gcttaagacg | 900 |
| gcaggtgtta atacctcgga taaggagcta gaaattcagt tcttgcgaaa tgtaactttt | 960 |
| gaggatgctg gggagtatac ttgtctcgct gggaactcta ttggctattc ccatcattct | 1020 |
| gcttggctca cggtgctgcc accagcagag ccggtcccag acgtcgacac ctctgtcagc | 1080 |
| attcttgccg ctgcaggatg tgtcgcagtt gttatactgg tggtgatcat aatctttact | 1140 |
| tacaagatga agatgccctc caagaagacc atgaacaccg ccactgtgca caaagtctca | 1200 |
| aagttccctc tcaagagaca ggtgtcactg gagtccaact cttcaatgaa ttccaacacc | 1260 |
| cctctggtgc gaatcacccg cctgtcgtcc agcgatggtc cgatgctggc caacgtgtcc | 1320 |
| gagctggagc tacccgctga tccgaagtgg gaattgtctc gttcacgctt gactttgggc | 1380 |
| aaacctcttg gggaaggatg ctttggccag gtggtgatgg cggatgcagt tggcattgaa | 1440 |
| aaggataagc caaacaaggc cacctcggtt gccgttaaga tgttgaaaga tgatgccact | 1500 |
| gataaagacc tgtcggatct agtctctgaa atggaaatga tgaaaatgat tgggaagcac | 1560 |
| aaaaacatca ttaatctcct gggagcctgc acgcaggatg gcccactcta cgtgctggtg | 1620 |
| gaatatgcat ccaaaggaaa cttgcgggag tacctgaggg cccggcgccc tcctggcatg | 1680 |
| gattactcct tcgacacctg caaacttccc gaagagcagt tgaccttcaa ggacttggta | 1740 |
| tcctgtgcct accaggtggc ccgcggcatg gagtacctgg cctctcagaa gtgcatacac | 1800 |
| cgagatctgg cagcccggaa cgtgctggtg acggatgaca acgttatgaa gattgctgat | 1860 |
| tttggcctgg cgagagatgt gcacaacatc gactactaca gaaaaactac aaatggccga | 1920 |
| ctgcccgtga agtggatggc tccggaggct tgttcgaccc gggtctacac tcaccaaagc | 1980 |
| gacgtctggt cgtttggagt gcttctgtgg gagatcttca cgctgggggg ctcgccgtac | 2040 |
| cctggaatcc cagtggaaga actcttcaag ctgttaaagg aaggccatcg aatggacaaa | 2100 |
| ccagcgaact gcacgcatga gctgtacatg atcatgcggg agtgctggca tgcagtgcca | 2160 |
| tcccagcggc caaccttcaa gcaactcgta gaagacttgg accgggtcct tacggtgacc | 2220 |
| tccactgatg agtacctcga tctctctgtg cccttcgagc agtattcgcc tgcctgccca | 2280 |
| gacagccaca gcagctgctc ttctggagac gattcggtct tgcccacga cctgcccgag | 2340 |
| gagccctgcc ttccgaagca ccagcagtac aatggagtaa tccgaacatg a | 2391 |

<210> SEQ ID NO 26
<211> LENGTH: 796
<212> TYPE: PRT
<213> ORGANISM: Pleurodeles waltlii FGFR3

<400> SEQUENCE: 26

| | | | | | | | | | | | | | | |
|---|---|---|---|---|---|---|---|---|---|---|---|---|---|---|
|Met|Leu|Val|Trp|Leu|Cys|Gly|Leu|Cys|Leu|Val|Thr|Leu|Ala|Gly|Gly|
|1| | | |5| | | | |10| | | | |15| |

Arg Ser Ala Ala Arg Leu Pro Leu Thr Glu Gly Arg Pro Thr Ala Asp
            20                  25                  30

Phe Leu Pro Gly Asp Ala Ser Leu Val Glu Glu Leu Leu Phe Gly Thr
        35                  40                  45

Gly Asp Thr Ile Glu Leu Ser Cys Thr Thr Pro Gly Ser Ser Val Ser
        50                  55                  60

Val Val Trp Phe Lys Asp Gly Ile Ser Val Asp Pro Pro Thr Trp Ser
65                  70                  75                  80

His Thr Gly Gln Lys Leu Leu Lys Ile Ile Asn Val Ser Tyr Asp Asp
                85                  90                  95

Ser Gly Val Tyr Ser Cys Lys Ala Arg Gln Ser Ser Glu Val Leu Arg
            100                 105                 110

Asn Val Thr Val Arg Val Thr Asp Ser Pro Ser Ser Gly Asp Asp Glu
            115                 120                 125

Asp Asp Asp Glu Glu Ser Glu Ser Ala Asn Ala Pro Lys Phe Thr Arg
        130                 135                 140

Pro Glu Trp Met Glu Lys Lys Leu Leu Ala Val Pro Ala Ala Asn Thr
145                 150                 155                 160

Val Arg Phe Arg Cys Pro Ala Ala Gly Lys Pro Thr Pro Ser Ile Thr
                165                 170                 175

Trp Leu Lys Asn Gly Lys Glu Phe Lys Gly Glu His Arg Ile Gly Gly
            180                 185                 190

Ile Lys Leu Arg His Gln Gln Trp Ser Leu Val Met Glu Ser Val Val
            195                 200                 205

Pro Ser Asp Arg Gly Asn Tyr Thr Cys Val Val Ala Asn Lys Tyr Gly
        210                 215                 220

Thr Ile Arg Glu Thr Tyr Thr Leu Asp Val Leu Glu Arg Thr Pro His
225                 230                 235                 240

Arg Pro Ile Leu Gln Ala Gly Phe Arg Ser Asn Lys Thr Val Val Val
                245                 250                 255

Gly Ser Asp Val Glu Phe His Cys Lys Val Tyr Ser Asp Ala Gln Pro
            260                 265                 270

His Ile Gln Trp Leu Lys His Val Glu Val Asn Gly Ser Lys Phe Gly
        275                 280                 285

Pro Asp Gly Asn Pro Tyr Val Thr Val Leu Lys Thr Ala Gly Val Asn
        290                 295                 300

Thr Ser Asp Lys Glu Leu Glu Ile Gln Phe Leu Arg Asn Val Thr Phe
305                 310                 315                 320

Glu Asp Ala Gly Glu Tyr Thr Cys Leu Ala Gly Asn Ser Ile Gly Tyr
                325                 330                 335

Ser His His Ser Ala Trp Leu Thr Val Leu Pro Ala Glu Pro Val
        340                 345                 350

Pro Asp Val Asp Thr Ser Val Ser Ile Leu Ala Ala Gly Cys Val
        355                 360                 365

Ala Val Val Ile Leu Val Val Ile Ile Ile Phe Thr Tyr Lys Met Lys
        370                 375                 380

Met Pro Ser Lys Lys Thr Met Asn Thr Ala Thr Val His Lys Val Ser
385                 390                 395                 400

Lys Phe Pro Leu Lys Arg Gln Val Ser Leu Glu Ser Asn Ser Ser Met
                405                 410                 415

Asn Ser Asn Thr Pro Leu Val Arg Ile Thr Arg Leu Ser Ser Ser Asp
            420                 425                 430

Gly Pro Met Leu Ala Asn Val Ser Glu Leu Glu Leu Pro Ala Asp Pro
            435                 440             445

Lys Trp Glu Leu Ser Arg Ser Arg Leu Thr Leu Gly Lys Pro Leu Gly
        450                 455                 460

Glu Gly Cys Phe Gly Gln Val Val Met Ala Asp Ala Val Gly Ile Glu
465                 470                 475                 480

Lys Asp Lys Pro Asn Lys Ala Thr Ser Val Ala Val Lys Met Leu Lys
                485                 490                 495

Asp Asp Ala Thr Asp Lys Asp Leu Ser Asp Leu Val Ser Glu Met Glu
            500                 505                 510

Met Met Lys Met Ile Gly Lys His Lys Asn Ile Ile Asn Leu Leu Gly
            515                 520                 525

Ala Cys Thr Gln Asp Gly Pro Leu Tyr Val Leu Val Glu Tyr Ala Ser
        530                 535                 540

Lys Gly Asn Leu Arg Glu Tyr Leu Arg Ala Arg Arg Pro Pro Gly Met
545                 550                 555                 560

Asp Tyr Ser Phe Asp Thr Cys Lys Leu Pro Glu Gln Leu Thr Phe
                565                 570                 575

Lys Asp Leu Val Ser Cys Ala Tyr Gln Val Ala Arg Gly Met Glu Tyr
            580                 585                 590

Leu Ala Ser Gln Lys Cys Ile His Arg Asp Leu Ala Ala Arg Asn Val
        595                 600                 605

Leu Val Thr Asp Asp Asn Val Met Lys Ile Ala Asp Phe Gly Leu Ala
610                 615                 620

Arg Asp Val His Asn Ile Asp Tyr Tyr Lys Lys Thr Thr Asn Gly Arg
625                 630                 635                 640

Leu Pro Val Lys Trp Met Ala Pro Glu Ala Leu Phe Asp Arg Val Tyr
                645                 650                 655

Thr His Gln Ser Asp Val Trp Ser Phe Gly Val Leu Leu Trp Glu Ile
            660                 665                 670

Phe Thr Leu Gly Gly Ser Pro Tyr Pro Gly Ile Pro Val Glu Glu Leu
        675                 680                 685

Phe Lys Leu Leu Lys Glu Gly His Arg Met Asp Lys Pro Ala Asn Cys
            690                 695                 700

Thr His Glu Leu Tyr Met Ile Met Arg Glu Cys Trp His Ala Val Pro
705                 710                 715                 720

Ser Gln Arg Pro Thr Phe Lys Gln Leu Val Glu Asp Leu Asp Arg Val
                725                 730                 735

Leu Thr Val Thr Ser Thr Asp Glu Tyr Leu Asp Leu Ser Val Pro Phe
            740                 745                 750

Glu Gln Tyr Ser Pro Ala Cys Pro Asp Ser His Ser Ser Cys Ser Ser
        755                 760                 765

Gly Asp Asp Ser Val Phe Ala His Asp Leu Pro Glu Glu Pro Cys Leu
770                 775                 780

Pro Lys His Gln Gln Tyr Asn Gly Val Ile Arg Thr
785                 790                 795

<210> SEQ ID NO 27
<211> LENGTH: 2403
<212> TYPE: DNA
<213> ORGANISM: Danio rerio FGFR3

<400> SEQUENCE: 27

```
atggtcccac tctgtctcct cctgtacctc gcaaccctcg tcttcccacc agtgtacagt      60
gcacacctgc tgtccccaga gcccacagac tgggtatcga gtgaggtgga agtgtttctg     120
gaggactatg tggcgggagt cggggataca gtagttctgt cctgcacgcc gcaagacttt     180
ctccttccca tcgtatggca aaaagacgga gacgccgttt cttcaagcaa ccgtacacga     240
gtgggccaga aagccctccg catcatcaat gtctcctatg aagactcggg tgtttactcc     300
tgcagacatg cccacaagag catgcttctg agcaactaca ccgtcaaagt catcgattcg     360
ctgtcctctg tgatgatga ggactatgat gaagatgagg acgaggcagg taatggaaat     420
gcagaagctc catactggac ccgttcggac cggatggaga agaaactatt ggctgttcct     480
gctgccaata cagtcaagtt ccgctgtcct gctgctggca acccaacgcc cagtatccat     540
tggctgaaaa atggcaagga gttcaaggga gagcagagaa tgggcggcat taagctgagg     600
catcagcagt ggagcttggt catggagagt gccgttccat ccgaccgggg aaattacaca     660
tgtgtggtgc agaacaaata cgggtcaatc aagcacactt atcaactcga tgtgctggag     720
cgctcccctc accggcccat cttacaggca ggactgccag ccaatcagac ggtagtggtg     780
ggcagtgatg tggagttcca ctgtaaggtg tacagtgatg ctcagccaca catccagtgg     840
ctgaaacaca ttgaagtcaa tggaagccaa tatgggccca atggcgcccc ctacgtcaat     900
gttcttaaga ctgctgggat aaatactacg gataaagagc tggagattct ctacctgacc     960
aatgtgtctt cgaggatgc ggggcaatac acttgtctgg cagggaactc gattggctat    1020
aaccatcact ctgcttggct tacagtctta ccagcggtgg agatggagag agaggatgat    1080
tatgcagaca tcctcatcta tgtgacaagc tgcgtgctct tcattctcac catggtcatc    1140
attattctct gccgaatgtg gataaacacg cagaagactc tcccggcacc acctgttcaa    1200
aaactgtcca aattccccct caagagacag gtgtccttgg aatccaactc ttccatgaat    1260
tcaaacaccc cgctggtcag gatcgcccgc ctgtcatcca gcgatgggcc gatgttgcct    1320
aacgtgtctg aacttgaact gcccctctgac cccaagtggg agtttactcg aacaaagtta    1380
acgttgggga accgttggg agagggctgc tttgggcagg tggtgatggc tgaagccatt    1440
gggattgaca agaaaaaacc caacaaacct ctaactgttg ctgtcaagat gctcaaagat    1500
gacggcacag ataaagacct gtcagacctt gtgtctgaaa tggagatgat gaagatgatt    1560
gggaaacata gaacatcat taacttgctg ggagcatgta ctcaagacgg tcctctgtac    1620
gtgctggtag aatacgcctc taagggaat cttagggaat acttacgagc cagaaggcca    1680
cctgggatgg actactcatt cgacaccgtg aagatcccga acgaaacgct aacatttaaa    1740
gacctggtgt cctgcgccta tcaggtcgcc aggggtatgg agtacctggc ctcaaagaag    1800
tgtatccata gggaccccgc agcccggaat gttctggtta ccgaggacaa cgtgatgaag    1860
attgcagact tcgccttgc cagagatgtg cacaacattg actactacaa gaagaccacc    1920
aacggtcgtc tgcccgtcaa atggatggca ccagaagcac tgttcgatcg cgtctacacg    1980
caccagagcg atgtgtggtc ttatggtgtg ttgttgtggg agattttcac tcttggtgga    2040
tccccgtatc caggtatccc agtggaggag ctctttaaac tgctgaagga aggccatcgg    2100
atggacaaac cggccaactg cactcatgaa ctgtacatga tcatgcgaga atgttggcat    2160
gctgttcctt cacaaagacc cacgttcaga cagctggtgg aggaccacga cagggttctt    2220
tccatgacct ccactgacga gtacctggac ctctctgtac cgttcgagca gtattcaccg    2280
acctgtccgg actccaacag cacctgttcc tctggcgatg actctgtgtt tgcccacgac    2340
```

```
cccttacctg aggagccatg cctccctaaa caccaccaca gcaacggggt catacgaaca      2400
taa                                                                    2403

<210> SEQ ID NO 28
<211> LENGTH: 800
<212> TYPE: PRT
<213> ORGANISM: Danio rerio FGFR3

<400> SEQUENCE: 28

Met Val Pro Leu Cys Leu Leu Leu Tyr Leu Ala Thr Leu Val Phe Pro
 1               5                  10                  15

Pro Val Tyr Ser Ala His Leu Leu Ser Pro Glu Pro Thr Asp Trp Val
            20                  25                  30

Ser Ser Glu Val Glu Val Phe Leu Glu Asp Tyr Val Ala Gly Val Gly
        35                  40                  45

Asp Thr Val Val Leu Ser Cys Thr Pro Gln Asp Phe Leu Leu Pro Ile
    50                  55                  60

Val Trp Gln Lys Asp Gly Asp Ala Val Ser Ser Asn Arg Thr Arg
65                  70                  75                  80

Val Gly Gln Lys Ala Leu Arg Ile Ile Asn Val Ser Tyr Glu Asp Ser
                85                  90                  95

Gly Val Tyr Ser Cys Arg His Ala His Lys Ser Met Leu Leu Ser Asn
           100                 105                 110

Tyr Thr Val Lys Val Ile Asp Ser Leu Ser Ser Gly Asp Asp Glu Asp
       115                  120                 125

Tyr Asp Glu Asp Glu Asp Ala Gly Asn Gly Asn Ala Glu Ala Pro
   130                 135                 140

Tyr Trp Thr Arg Ser Asp Arg Met Glu Lys Lys Leu Leu Ala Val Pro
145                 150                 155                 160

Ala Ala Asn Thr Val Lys Phe Arg Cys Pro Ala Ala Gly Asn Pro Thr
                165                 170                 175

Pro Ser Ile His Trp Leu Lys Asn Gly Lys Glu Phe Lys Gly Glu Gln
            180                 185                 190

Arg Met Gly Gly Ile Lys Leu Arg His Gln Gln Trp Ser Leu Val Met
        195                 200                 205

Glu Ser Ala Val Pro Ser Asp Arg Gly Asn Tyr Thr Cys Val Val Gln
    210                 215                 220

Asn Lys Tyr Gly Ser Ile Lys His Thr Tyr Gln Leu Asp Val Leu Glu
225                 230                 235                 240

Arg Ser Pro His Arg Pro Ile Leu Gln Ala Gly Leu Pro Ala Asn Gln
                245                 250                 255

Thr Val Val Val Gly Ser Asp Val Glu Phe His Cys Lys Val Tyr Ser
            260                 265                 270

Asp Ala Gln Pro His Ile Gln Trp Leu Lys His Ile Glu Val Asn Gly
        275                 280                 285

Ser Gln Tyr Gly Pro Asn Gly Ala Pro Tyr Val Asn Val Leu Lys Thr
    290                 295                 300

Ala Gly Ile Asn Thr Thr Asp Lys Glu Leu Glu Ile Leu Tyr Leu Thr
305                 310                 315                 320

Asn Val Ser Phe Glu Asp Ala Gly Gln Tyr Thr Cys Leu Ala Gly Asn
                325                 330                 335

Ser Ile Gly Tyr Asn His His Ser Ala Trp Leu Thr Val Leu Pro Ala
            340                 345                 350
```

```
Val Glu Met Glu Arg Glu Asp Asp Tyr Ala Asp Ile Leu Ile Tyr Val
        355                 360                 365

Thr Ser Cys Val Leu Phe Ile Leu Thr Met Val Ile Ile Ile Leu Cys
    370                 375                 380

Arg Met Trp Ile Asn Thr Gln Lys Thr Leu Pro Ala Pro Pro Val Gln
385                 390                 395                 400

Lys Leu Ser Lys Phe Pro Leu Lys Arg Gln Val Ser Leu Glu Ser Asn
                405                 410                 415

Ser Ser Met Asn Ser Asn Thr Pro Leu Val Arg Ile Ala Arg Leu Ser
            420                 425                 430

Ser Ser Asp Gly Pro Met Leu Pro Asn Val Ser Glu Leu Glu Leu Pro
        435                 440                 445

Ser Asp Pro Lys Trp Glu Phe Thr Arg Thr Lys Leu Thr Leu Gly Lys
450                 455                 460

Pro Leu Gly Glu Gly Cys Phe Gly Gln Val Val Met Ala Glu Ala Ile
465                 470                 475                 480

Gly Ile Asp Lys Glu Lys Pro Asn Lys Pro Leu Thr Val Ala Val Lys
                485                 490                 495

Met Leu Lys Asp Asp Gly Thr Asp Lys Asp Leu Ser Asp Leu Val Ser
            500                 505                 510

Glu Met Glu Met Met Lys Met Ile Gly Lys His Lys Asn Ile Ile Asn
        515                 520                 525

Leu Leu Gly Ala Cys Thr Gln Asp Gly Pro Leu Tyr Val Leu Val Glu
    530                 535                 540

Tyr Ala Ser Lys Gly Asn Leu Arg Glu Tyr Leu Arg Ala Arg Arg Pro
545                 550                 555                 560

Pro Gly Met Asp Tyr Ser Phe Asp Thr Cys Lys Ile Pro Asn Glu Thr
                565                 570                 575

Leu Thr Phe Lys Asp Leu Val Ser Cys Ala Tyr Gln Val Ala Arg Gly
            580                 585                 590

Met Glu Tyr Leu Ala Ser Lys Lys Cys Ile His Arg Asp Pro Ala Ala
        595                 600                 605

Arg Asn Val Leu Val Thr Glu Asp Asn Val Met Lys Ile Ala Asp Phe
    610                 615                 620

Gly Leu Ala Arg Asp Val His Asn Ile Asp Tyr Tyr Lys Lys Thr Thr
625                 630                 635                 640

Asn Gly Arg Leu Pro Val Lys Trp Met Ala Pro Glu Ala Leu Phe Asp
                645                 650                 655

Arg Val Tyr Thr His Gln Ser Asp Val Trp Ser Tyr Gly Val Leu Leu
            660                 665                 670

Trp Glu Ile Phe Thr Leu Gly Gly Ser Pro Tyr Pro Gly Ile Pro Val
        675                 680                 685

Glu Glu Leu Phe Lys Leu Leu Lys Glu Gly His Arg Met Asp Lys Pro
    690                 695                 700

Ala Asn Cys Thr His Glu Leu Tyr Met Ile Met Arg Glu Cys Trp His
705                 710                 715                 720

Ala Val Pro Ser Gln Arg Pro Thr Phe Arg Gln Leu Val Glu Asp His
                725                 730                 735

Asp Arg Val Leu Ser Met Thr Ser Thr Asp Glu Tyr Leu Asp Leu Ser
            740                 745                 750

Val Pro Phe Glu Gln Tyr Ser Pro Thr Cys Pro Asp Ser Asn Ser Thr
        755                 760                 765

Cys Ser Ser Gly Asp Asp Ser Val Phe Ala His Asp Pro Leu Pro Glu
```

```
                  770                 775                 780
Glu Pro Cys Leu Pro Lys His His His Ser Asn Gly Val Ile Arg Thr
    785                 790                 795                 800

<210> SEQ ID NO 29
<211> LENGTH: 20
<212> TYPE: DNA
<213> ORGANISM: Artificial Sequence
<220> FEATURE:
<223> OTHER INFORMATION: PCR Primer 1

<400> SEQUENCE: 29
agccctcact ccttctctag                                              20

<210> SEQ ID NO 30
<211> LENGTH: 26
<212> TYPE: DNA
<213> ORGANISM: Artificial Sequence
<220> FEATURE:
<223> OTHER INFORMATION: PCR Primer 2

<400> SEQUENCE: 30
acctacaggt ggggtctttc attccc                                       26

<210> SEQ ID NO 31
<211> LENGTH: 25
<212> TYPE: DNA
<213> ORGANISM: Artificial Sequence
<220> FEATURE:
<223> OTHER INFORMATION: PCR Primer 3

<400> SEQUENCE: 31
ccctgggtca agccctttgt acacc                                        25

<210> SEQ ID NO 32
<211> LENGTH: 25
<212> TYPE: DNA
<213> ORGANISM: Artificial Sequence
<220> FEATURE:
<223> OTHER INFORMATION: PCR Primer 4

<400> SEQUENCE: 32
tgccaaacct acaggtgggg tcttt                                        25

<210> SEQ ID NO 33
<211> LENGTH: 604
<212> TYPE: PRT
<213> ORGANISM: Homo sapiens

<400> SEQUENCE: 33

Ala Gln Arg Arg Lys Glu Arg Glu Glu Leu Ala Gln Gln Tyr Glu Ala
  1               5                  10                  15

Ile Leu Arg Glu Cys Gly His Gly Arg Phe Gln Trp Thr Leu Tyr Phe
                 20                  25                  30

Val Leu Gly Leu Ala Leu Met Ala Asp Gly Val Glu Val Phe Val Val
             35                  40                  45

Gly Phe Val Leu Pro Ser Ala Glu Lys Asp Met Cys Leu Ser Asp Ser
         50                  55                  60

Asn Lys Gly Met Leu Gly Leu Ile Val Tyr Leu Gly Met Met Val Gly
 65                  70                  75                  80

Ala Phe Leu Trp Gly Gly Leu Ala Asp Arg Leu Gly Arg Arg Gln Cys
                 85                  90                  95
```

```
Leu Leu Ile Ser Leu Ser Val Asn Ser Val Phe Ala Phe Phe Ser Ser
            100                 105                 110
Phe Val Gln Gly Tyr Gly Thr Phe Leu Phe Cys Arg Leu Leu Ser Gly
        115                 120                 125
Val Gly Ile Gly Gly Ser Ile Pro Ile Val Phe Ser Tyr Phe Ser Glu
    130                 135                 140
Phe Leu Ala Gln Glu Lys Arg Gly Glu His Leu Ser Trp Leu Cys Met
145                 150                 155                 160
Phe Trp Met Ile Gly Val Tyr Ala Ala Met Ala Trp Ala Ile
                165                 170                 175
Ile Pro His Tyr Gly Trp Ser Phe Gln Met Gly Ser Ala Tyr Gln Phe
            180                 185                 190
His Ser Trp Arg Val Phe Val Leu Val Cys Ala Phe Pro Ser Val Phe
        195                 200                 205
Ala Ile Gly Ala Leu Thr Thr Gln Pro Glu Ser Pro Arg Phe Phe Leu
    210                 215                 220
Glu Asn Gly Lys His Asp Glu Ala Trp Met Val Leu Lys Gln Val His
225                 230                 235                 240
Asp Thr Asn Met Arg Ala Lys Gly His Pro Glu Arg Val Phe Ser Val
                245                 250                 255
Thr His Ile Lys Thr Ile His Gln Glu Asp Glu Leu Ile Glu Ile Gln
            260                 265                 270
Ser Asp Thr Gly Thr Trp Tyr Gln Arg Trp Gly Val Arg Ala Leu Ser
        275                 280                 285
Leu Gly Gly Gln Val Trp Gly Asn Phe Leu Ser Cys Phe Gly Pro Glu
    290                 295                 300
Tyr Arg Arg Ile Thr Leu Met Met Met Gly Val Trp Phe Thr Met Ser
305                 310                 315                 320
Phe Ser Tyr Tyr Gly Leu Thr Val Trp Phe Pro Asp Met Ile Arg His
                325                 330                 335
Leu Gln Ala Val Asp Tyr Ala Ser Arg Thr Lys Val Phe Pro Gly Glu
            340                 345                 350
Arg Val Glu His Val Thr Phe Asn Phe Thr Leu Glu Asn Gln Ile His
        355                 360                 365
Arg Gly Gly Gln Tyr Phe Asn Asp Lys Phe Ile Gly Leu Arg Leu Lys
    370                 375                 380
Ser Val Ser Phe Glu Asp Ser Leu Phe Glu Glu Cys Tyr Phe Glu Asp
385                 390                 395                 400
Val Thr Ser Ser Asn Thr Phe Phe Arg Asn Cys Thr Phe Ile Asn Thr
                405                 410                 415
Val Phe Tyr Asn Thr Asp Leu Phe Glu Tyr Lys Phe Val Asn Ser Arg
            420                 425                 430
Leu Ile Asn Ser Thr Phe Leu His Asn Lys Glu Gly Cys Pro Leu Asp
        435                 440                 445
Val Thr Gly Thr Gly Glu Gly Ala Tyr Met Val Tyr Phe Val Ser Phe
    450                 455                 460
Leu Gly Thr Leu Ala Val Leu Pro Gly Asn Ile Val Ser Ala Leu Leu
465                 470                 475                 480
Met Asp Lys Ile Gly Arg Leu Arg Met Leu Ala Gly Ser Ser Val Met
                485                 490                 495
Ser Cys Val Ser Cys Phe Phe Leu Ser Phe Gly Asn Ser Glu Ser Ala
            500                 505                 510
Met Ile Ala Leu Leu Cys Leu Phe Gly Gly Val Ser Ile Ala Ser Trp
```

```
                515                 520                 525
Asn Ala Leu Asp Val Leu Thr Val Glu Leu Tyr Pro Ser Asp Lys Arg
            530                 535                 540

Thr Thr Ala Phe Gly Phe Leu Asn Ala Leu Cys Lys Leu Ala Ala Val
545                 550                 555                 560

Leu Gly Ile Ser Ile Phe Thr Ser Phe Val Gly Ile Thr Lys Ala Ala
                565                 570                 575

Pro Ile Leu Phe Ala Ser Ala Leu Ala Leu Gly Ser Ser Leu Ala
                580                 585                 590

Leu Lys Leu Pro Glu Thr Arg Gly Gln Val Leu Gln
        595                 600

<210> SEQ ID NO 34
<211> LENGTH: 683
<212> TYPE: PRT
<213> ORGANISM: Homo sapiens

<400> SEQUENCE: 34

Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65                  70                  75                  80

Met Ala Glu Arg Leu Glu Asp Glu Gln Leu Ala His Gln Tyr Glu
                85                  90                  95

Thr Ile Met Asp Glu Cys Gly His Gly Arg Phe Gln Trp Ile Leu Phe
                100                 105                 110

Phe Val Leu Gly Leu Ala Leu Met Ala Asp Gly Val Glu Val Phe Val
            115                 120                 125

Val Ser Phe Ala Leu Pro Ser Ala Glu Lys Asp Met Cys Leu Ser Ser
130                 135                 140

Ser Lys Lys Gly Met Leu Gly Met Ile Val Tyr Leu Gly Met Met Ala
145                 150                 155                 160

Gly Ala Phe Ile Leu Gly Gly Leu Ala Asp Lys Leu Gly Arg Lys Arg
                165                 170                 175

Val Leu Ser Met Ser Leu Ala Val Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ala Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Cys Thr
        275                 280                 285
```

```
Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser Asn Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Lys
        355                 360                 365

Thr Ile Phe Lys Gln Val Trp Asp Asn Ala Leu Tyr Cys Val Met Gly
    370                 375                 380

Pro Tyr Arg Met Asn Thr Leu Ile Leu Ala Val Val Trp Phe Ala Met
385                 390                 395                 400

Ala Phe Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430

Glu His Val Tyr Gly Ala Thr Ile Asn Phe Thr Met Glu Asn Gln Ile
        435                 440                 445

His Gln His Gly Lys Leu Val Asn Asp Lys Phe Thr Arg Met Tyr Phe
    450                 455                 460

Lys His Val Leu Phe Glu Asp Thr Phe Phe Asp Glu Cys Tyr Phe Glu
465                 470                 475                 480

Asp Val Thr Ser Thr Asp Thr Tyr Phe Lys Asn Cys Thr Ile Glu Ser
                485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
        515                 520                 525

Asp Leu Glu Gln Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ser Leu Val Gly Gly Leu Ile Ala Leu
            660                 665                 670

Arg Leu Pro Glu Thr Arg Glu Gln Val Leu Ile
        675                 680

<210> SEQ ID NO 35
<211> LENGTH: 727
<212> TYPE: PRT
```

<213> ORGANISM: Homo sapiens

<400> SEQUENCE: 35

```
Met Glu Asp Ser Tyr Lys Asp Arg Thr Ser Leu Met Lys Gly Ala Lys
 1               5                  10                  15
Asp Ile Ala Arg Glu Val Lys Lys Gln Thr Val Lys Lys Val Asn Gln
            20                  25                  30
Ala Val Asp Arg Ala Gln Asp Glu Tyr Thr Gln Arg Ser Tyr Ser Arg
        35                  40                  45
Phe Gln Asp Glu Glu Asp Asp Asp Tyr Tyr Pro Ala Gly Glu Thr
 50                  55                  60
Tyr Asn Gly Glu Ala Asn Asp Asp Glu Gly Ser Ser Glu Ala Thr Glu
 65                  70                  75                  80
Gly His Asp Glu Asp Glu Ile Tyr Glu Gly Glu Tyr Gln Gly Ile
                85                  90                  95
Pro Ser Met Asn Gln Ala Lys Asp Ser Ile Val Ser Val Gly Gln Pro
            100                 105                 110
Lys Gly Asp Glu Tyr Lys Asp Arg Arg Glu Leu Glu Ser Glu Arg Arg
        115                 120                 125
Ala Asp Glu Glu Glu Leu Ala Gln Gln Tyr Glu Leu Ile Ile Gln Glu
130                 135                 140
Cys Gly His Gly Arg Phe Gln Trp Ala Leu Phe Val Leu Gly Met
145                 150                 155                 160
Ala Leu Met Ala Asp Gly Val Glu Val Phe Val Val Gly Phe Val Leu
                165                 170                 175
Pro Ser Ala Glu Thr Asp Leu Cys Ile Pro Asn Ser Gly Ser Gly Trp
            180                 185                 190
Leu Gly Ser Ile Val Tyr Leu Gly Met Met Val Gly Ala Phe Phe Trp
        195                 200                 205
Gly Gly Leu Ala Asp Lys Val Gly Arg Lys Gln Ser Leu Leu Ile Cys
210                 215                 220
Met Ser Val Asn Gly Phe Phe Ala Phe Leu Ser Ser Phe Val Gln Gly
225                 230                 235                 240
Tyr Gly Phe Phe Leu Phe Cys Arg Leu Leu Ser Gly Phe Gly Ile Gly
                245                 250                 255
Gly Ala Ile Pro Thr Val Phe Ser Tyr Phe Ala Glu Val Leu Ala Arg
            260                 265                 270
Glu Lys Arg Gly Glu His Leu Ser Trp Leu Cys Met Phe Trp Met Ile
        275                 280                 285
Gly Gly Ile Tyr Ala Ser Ala Met Ala Trp Ala Ile Ile Pro His Tyr
290                 295                 300
Gly Trp Ser Phe Ser Met Gly Ser Ala Tyr Gln Phe His Ser Trp Arg
305                 310                 315                 320
Val Phe Val Ile Val Cys Ala Leu Pro Cys Val Ser Ser Val Val Ala
                325                 330                 335
Leu Thr Phe Met Pro Glu Ser Pro Arg Phe Leu Leu Glu Val Gly Lys
            340                 345                 350
His Asp Glu Ala Trp Met Ile Leu Lys Leu Ile His Asp Thr Asn Met
        355                 360                 365
Arg Ala Arg Gly Gln Pro Glu Lys Val Phe Thr Val Asn Lys Ile Lys
370                 375                 380
Thr Pro Lys Gln Ile Asp Glu Leu Ile Glu Ile Glu Ser Asp Thr Gly
385                 390                 395                 400
```

```
Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
            420                 425                 430

Thr Ile Lys Leu Thr Ile Val Trp Phe Thr Leu Ser Phe Gly Tyr Tyr
        435                 440                 445

Gly Leu Ser Val Trp Phe Pro Asp Val Ile Lys Pro Leu Gln Ser Asp
    450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
                485                 490                 495

Tyr Asp Asn Gly Arg Phe Ile Gly Val Lys Phe Lys Ser Val Thr Phe
            500                 505                 510

Lys Asp Ser Val Phe Lys Ser Cys Thr Phe Glu Asp Val Thr Ser Val
        515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ser Ile Pro Ile Leu Leu Ala
    690                 695                 700

Ser Thr Val Leu Val Cys Gly Gly Leu Val Gly Leu Cys Leu Pro Asp
705                 710                 715                 720

Thr Arg Thr Gln Val Leu Met
                725

<210> SEQ ID NO 36
<211> LENGTH: 742
<212> TYPE: PRT
<213> ORGANISM: Homo sapiens

<400> SEQUENCE: 36

Met Glu Glu Gly Phe Arg Asp Arg Ala Ala Phe Ile Arg Gly Ala Lys
1               5                   10                  15

Asp Ile Ala Lys Glu Val Lys Lys His Ala Ala Lys Lys Val Val Lys
            20                  25                  30

Gly Leu Asp Arg Val Gln Asp Glu Tyr Ser Arg Arg Ser Tyr Ser Arg
        35                  40                  45
```

-continued

```
Phe Glu Glu Asp Asp Asp Asp Phe Pro Ala Pro Ser Asp Gly
    50              55              60

Tyr Tyr Arg Gly Glu Gly Thr Gln Asp Glu Glu Gly Gly Ala Ser
65              70              75              80

Ser Asp Ala Thr Glu Gly His Asp Glu Asp Glu Ile Tyr Glu Gly
            85              90              95

Glu Tyr Gln Asp Ile Pro Arg Ala Glu Ser Gly Gly Lys Gly Glu Arg
            100             105             110

Met Ala Asp Gly Ala Pro Leu Ala Gly Val Arg Gly Gly Leu Ser Asp
        115             120             125

Gly Glu Gly Pro Pro Gly Gly Arg Gly Glu Ala Gln Arg Arg Lys Glu
    130             135             140

Arg Glu Glu Leu Ala Gln Gln Tyr Glu Ala Ile Leu Arg Glu Cys Gly
145             150             155             160

His Gly Arg Phe Gln Trp Thr Leu Tyr Phe Val Leu Gly Leu Ala Leu
            165             170             175

Met Ala Asp Gly Val Glu Val Phe Val Val Gly Phe Val Leu Pro Ser
        180             185             190

Ala Glu Lys Asp Met Cys Leu Ser Asp Ser Asn Lys Gly Met Leu Gly
    195             200             205

Leu Ile Val Tyr Leu Gly Met Met Val Gly Ala Phe Leu Trp Gly Gly
    210             215             220

Leu Ala Asp Arg Leu Gly Arg Arg Gln Cys Leu Leu Ile Ser Leu Ser
225             230             235             240

Val Asn Ser Val Phe Ala Phe Phe Ser Ser Phe Val Gln Gly Tyr Gly
            245             250             255

Thr Phe Leu Phe Cys Arg Leu Leu Ser Gly Val Gly Ile Gly Gly Ser
        260             265             270

Ile Pro Ile Val Phe Ser Tyr Phe Ser Glu Phe Leu Ala Gln Glu Lys
    275             280             285

Arg Gly Glu His Leu Ser Trp Leu Cys Met Phe Trp Met Ile Gly Gly
    290             295             300

Val Tyr Ala Ala Ala Met Ala Trp Ala Ile Ile Pro His Tyr Gly Trp
305             310             315             320

Ser Phe Gln Met Gly Ser Ala Tyr Gln Phe His Ser Trp Arg Val Phe
            325             330             335

Val Leu Val Cys Ala Phe Pro Ser Val Phe Ala Ile Gly Ala Leu Thr
        340             345             350

Thr Gln Pro Glu Ser Pro Arg Phe Phe Leu Glu Asn Gly Lys His Asp
    355             360             365

Glu Ala Trp Met Val Leu Lys Gln Val His Asp Thr Asn Met Arg Ala
    370             375             380

Lys Gly His Pro Glu Arg Val Phe Ser Val Thr His Ile Lys Thr Ile
385             390             395             400

His Gln Glu Asp Glu Leu Ile Glu Ile Gln Ser Asp Thr Gly Thr Trp
            405             410             415

Tyr Gln Arg Trp Gly Val Arg Ala Leu Ser Leu Gly Gly Gln Val Trp
        420             425             430

Gly Asn Phe Leu Ser Cys Phe Gly Pro Glu Tyr Arg Arg Ile Thr Leu
    435             440             445

Met Met Met Gly Val Trp Phe Thr Met Ser Phe Ser Tyr Tyr Gly Leu
    450             455             460
```

-continued

```
Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Gly His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740
```

BOTULINUM TOXIN SCREENING ASSAYS

This is a continuation in part that claims priority under 35 U.S.C. §120 to U.S. patent application Ser. No. 10/598,073, filed Aug. 17, 2006, a national stage application under 35 U.S.C. §371 of International Application PCT/US2005/006421, filed on Feb. 23, 2005, which claims the benefit of U.S. Provisional Application Ser. No. 60/547,591, filed Feb. 24, 2004, each of which is hereby incorporated by reference in its entirety.

All of the publications cited in this application are hereby incorporated by reference herein in their entirety.

The myorelaxant properties of *Botulinum* toxins (BoNTs) are being exploited in a wide variety of therapeutic and cosmetic applications, see e.g., William J. Lipham, COSMETIC AND CLINICAL APPLICATIONS OF BOTULINUM TOXIN (Slack, Inc., 2004). For example, CoNTs therapies are proposed for treating dystonia, see e.g., Kei Roger Aoki, et al., *Method for treating Dystonia with botulinum toxin C to G*, U.S. Pat. No. 6,319,505 (Nov. 20, 2001); pain, see e.g., Kei Roger Aoki, et al., *Method for Treating Pain by Peripheral Administration of a Neurotoxin*, U.S. Pat. No. 6,464,986 (Oct. 15, 2002); muscle injuries, see e.g., Gregory F. Brooks, *Methods for Treating Muscle Injuries*, U.S. Pat. No. 6,423,319 (Jul. 23, 2002); cardiovascular diseases, see e.g., Gregory F. Brooks, *Methods for Treating Cardiovascular Diseases with Botulinum Toxins*, U.S. Patent Publication No. 2003/0185860 (Oct. 2, 2003); neuropsychiatric disorders, see e.g., Steven Donovan, *Therapeutic Treatments for Neuropsychiatric Disorders*, U.S. Patent Publication No. 2003/0211121 (Nov. 13, 2003); lower back pain, see e.g., Kei Roger Aoki, et al., *Botulinum Toxin Therapy for Lower Back Pain*, U.S. Patent Publication No. 2004/0037852 (Feb. 26, 2004); as well as other neuromuscular disorders, see e.g., Kei Roger Aoki, et al., *Multiple Botulinum Toxins for Treating Neuromuscular Disorders and Conditions*, U.S. Patent Publication No. 2001/0021695 (Sep. 13, 2001); Kei Roger Aoki, et al., *Treatment of Neuromuscular Disorders and Conditions with Different Botulinum*, U.S. Patent Publication No. 2002/0010138 (Jan. 24, 2002); Kei Roger Aoki, et al., *Use of Botulinum toxins for Treating Various Disorders and Conditions and Associated Pain*, U.S. Patent Publication No. 2004/0013692 (Jan. 22, 2004). Additional proposed uses of BoNTs as biopharmaceutical neuromodulators has expanded to cover a wide variety of treatments targeting certain disorders that lack a neuromuscular basis. For example, the effects on the autonomic nervous system has allowed the development of a *botulinum* toxin serotype A (BoNT/A) therapy for treating axillary hyperhydrosis or sweating, and reports indicate BoNT/A may be an effective treatment for myofascial pain and tension, stroke, traumatic brain injury, cerebral palsy, gastrointestinal motility disorders, urinary incontinence cancer and migraine headaches. Lastly, cosmetic and other therapeutic applications are widely known. In fact, the expected use of BoNTs in both therapeutic and cosmetic treatments of humans is anticipated to expand to an ever widening range of diseases and aliments that can benefit from the myorelaxant properties of these toxins.

The growing clinical and therapeutic use of *botulinum* toxins necessitates the pharmaceutical industry to use accurate assays for BoNT activity in order to, for example, ensure accurate pharmaceutical formulations and monitor established quality control standards. In addition, given the potential danger associated with small quantities of BoNT in foodstuffs, the food industry requires BoNT activity assays, for example, to validate new food packaging methods and to ensure food safety. Additionally, BoNT activity assays are useful in identifying modulators of BoNT activity, for example, modulators that reduce BoNT activity which can be useful as a toxin antidote and modulators that increase BoNT activity which can be useful in creating more potent or longer lasting pharmaceutical formulations. The present invention provides novel BoNT assays for detecting the presence or activity of a BoNT useful for various industries, such as, e.g. the pharmaceutical and food industries, and provides related advantages as well.

BRIEF DESCRIPTION OF THE DRAWINGS

FIG. 3 shows the results of electroporation of PURE-A into HIT-T15 cells.

FIG. 4 shows the affects of electroporation of HIT-T15 cells over time.

FIG. 7 shows the analysis of two isolated HIT-T15 cell isolates C6 and C7.

FIG. 8 shows Western blot analysis identifying cells with high affinity uptake for a Clostridial toxin.

FIG. 9 shows Western blot analysis evaluating the effects of ganglioside treatments used to increase uptake of a *botulinum* toxin.

FIG. 10 shows the results of a crosslinking experiment in Neuro-2A cells using a BoNT/A-SBED toxin. FIG. 10a shows the isolation of a complex of approximately 250 kDa from Neuro-2A cells containing the 150 kDa neurotoxin cross-linked to the putative BONT/A receptor. Bands were visualized with silver staining. FIG. 10b shows a Western blot analysis used to identify a BoNT/A receptor. The blots shows the presence of a single band corresponding to the 97 kDa FGFR3 (first panel) and two bands corresponding to the 150 kDa BoNT/A holotoxin and the 100 kDa BoNT/A heavy chain (second panel), with equal amounts of protein loaded per lane and probed with an antibody that detects either FGFR3 or BoNT/A.

FIG. 13 shows the results FGFR3 phosphorylation studies in Neuro-2A cells.

DETAILED DESCRIPTION OF THE INVENTION

Figure 1:
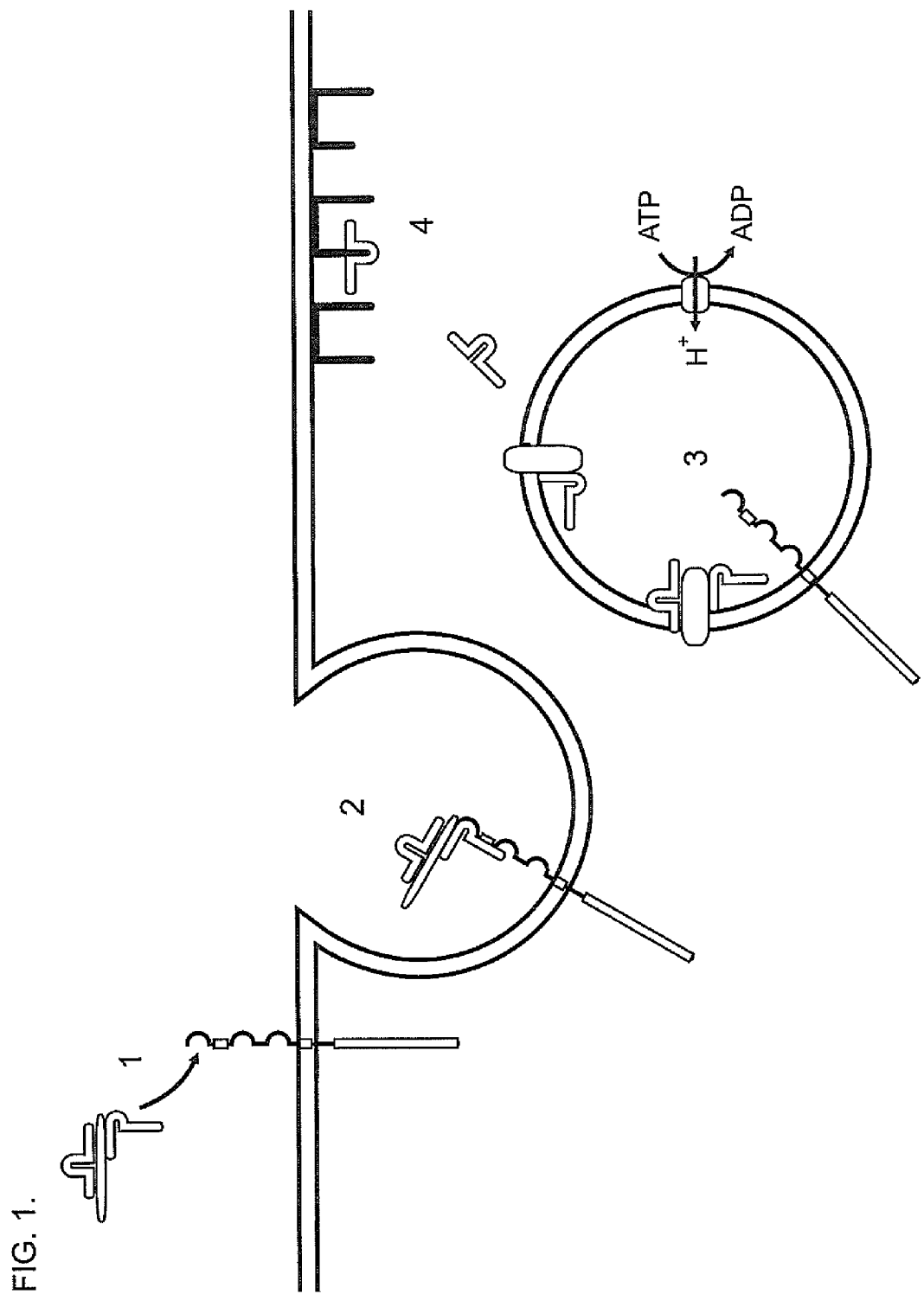
FIG. 1 shows a schematic of the current paradigm of the BoNT/A intoxication mechanism. This intoxication process can be described as comprising four steps: 1) receptor binding, where BoNT/A binds to a BoNT/A receptor system initiates the intoxication process; 2) complex internalization, where after BoNT/A binding, a vesicle containing a toxin/receptor system complex is endocytosised into the cell; 3) light chain translocation, where multiple events are thought to occur, including changes in the internal pH of the vesicle, formation of a channel pore comprising the $H_N$ domain of BoNT/A heavy chain, separation of the BoNT/A light chain from the heavy chain, enzymatic activation of the light chain; and release of the activated light chain and 4) enzymatic target modification, where the activated light chain of BoNT/A proteolytically cleaves its target SNARE substrates, such as, e.g., SNAP-25.

The present invention is based on the identification of a cell surface receptor to which BoNT/A selectively binds as the first step to the selective intoxication of a neuron. The present specification, in part, discloses that the Fibroblast Growth Factor Receptor 3 (FGFR3) is useful as a BoNT receptor, such as, e.g., a BoNT/A receptor. In addition, the present disclosure identifies SV2 as a co-receptor with FGFR3 which enhances binding of a BoNT to a BoNT receptor, such as, e.g., a FGFR3. Further, the present disclosure identifies specific gangliosides which facilitate binding of a BoNT to a BoNT receptor and the internalization of these toxins within a neural cell, such as, e.g., an increased binding of BoNT/A for a BoNT/A receptor using a ganglioside like GT1b; and an increased binding of BoNT/E for a BoNT/E receptor using a ganglioside like GQ1b, GD1a, GD1b or GD3.

The present invention provides novel assays for detecting the presence or absence of an active BoNT/A. The novel methods disclosed in the present specification reduce the need for animal-based toxicity studies, yet serve to analyze multiple toxin functions, namely, binding and cellular uptake of toxin, translocation into the cell cytosol, and protease activity. As discussed further below, the novel methods of the present disclosure can be used to analyze crude and bulk samples as well as highly purified dichain toxins and formulated toxin products and further are amenable to automated high throughput assay formats.

Aspects of the present invention provide methods of detecting BoNT/A activity by contacting a sample to a cell that contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspects of the present invention provide methods of detecting BoNT/A activity by contacting a sample to a cell that transiently contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspects of the present invention provide methods of detecting BoNT/A activity by contacting a sample to a cell that stably contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspect of the present invention provide methods of reducing BoNT/A activity in a human comprising administering to said human a pharmaceutical composition comprising a molecule that selectively binds a FGFR3, a SV2, or both a FGFR3 and a SV2 wherein said selective binding reduces the ability of BoNT/A to bind to said FGFR3. Other aspect of the present invention provide methods of reducing BoNT/A activity in a human comprising administering to said human a pharmaceutical composition comprising a molecule that selectively binds a FGFR3, a SV2, or both a FGFR3 and a SV2 wherein said selective binding reduces the ability of BoNT/A to bind to said SV2, either by preventing BoNT/A binding to a BoNT/A receptor, or by preventing said SV2 association with a FGFR3.

Other aspect of the present invention provide methods of screening for a molecule able to compete with BoNT/A for selective binding to cells susceptible to BoNT/A intoxication by contacting said sample with a composition comprising a FGFR3, a SV2, or both a FGFR3 and a SV2 and detecting whether said molecule selectively binds said FGFR3, said SV2, or both said FGFR3 and said SV2, wherein selective binding of said molecule to said FGFR3, said SV2, or both said FGFR3 and said SV2 indicates that said molecule is able to compete with BoNT/A for selective binding to cells susceptible to BoNT/A intoxication, and wherein if said molecule is BoNT/A, said method does not comprise an $LD_{50}$ assay.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin with a composition comprising a FGFR3 and detecting whether said neurotoxin selectively binds said FGFR3, wherein selective binding of said neurotoxin to said FGFR3 indicates that said neurotoxin is able to selective binding to cells susceptible to BoNT/A intoxication and wherein if said molecule is BoNT/A, said method does not comprise an $LD_{50}$ assay; packaging said neurotoxin for sale in a manner consistent with the requirements of said regulatory authority, and selling said neurotoxin.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity; packaging said neurotoxin for sale in a manner consistent with the requirements of said regulatory authority, and selling said neurotoxin.

BoNTs are each translated as a single chain polypeptide of approximately 150 kDa that is subsequently cleaved by proteolytic scission within a disulphide loop by bacterial or tissue proteases. This posttranslational processing yields a di-chain molecule comprising an approximately 50 kDa light chain (LC) and an approximately 100 kDa heavy chain (HC) held together by a single disulphide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the toxin from intracellular vesicles into the cytoplasm of the target cell; and 3) a binding domain found within the carboxy-terminal half of the HC ($H_C$) that determines the binding activity and binding specificity of the toxin to the receptor complex located at the surface of the target cell.

The binding, translocation and enzymatic activity of these three functional domains are all necessary for toxicity. While all details of this process are not yet precisely known, the overall cellular intoxication mechanism whereby BoNTs enter a neuron and inhibit neurotransmitter release is similar, regardless of type. Although the applicants have no wish to be limited by the following description, the intoxication mechanism can be described as comprising four steps: 1) receptor binding, 2) complex internalization, 3) light chain translocation, and 4) enzymatic target modification (see FIG. 1). The process is initiated when the $H_C$ domain of a BoNT binds to BoNT-specific receptor complex located on the plasma membrane surface of a target cell. The binding specificity of a receptor complex is thought to be achieved, in part, by specific combinations of gangliosides and protein receptors that appear to distinctly comprise each BoNT/A receptor complex. Once bound, the BoNT/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. Once activated, light chain endopeptidase of the toxin is released from the intracellular vesicle into the cytosol where it specifically targets one of three known core components of the neurotransmitter release apparatus. Three of these core proteins, vesicle-associated membrane protein (VAMP)/synaptobrevin, synaptosomal-associated protein of 25 kDa (SNAP-25)

and Syntaxin, are necessary for synaptic vesicle docking and fusion at the nerve terminal and constitute members of the soluble N-ethylmaleimide-sensitive factor-attachment protein-receptor (SNARE) family. The selective proteolysis of synaptic SNAREs accounts for the total block of neurotransmitter release caused by clostridial toxins in vivo. The SNARE protein targets of clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); M. Zouhair Atassi, *Basic and Therapeutic Aspects of Botulinum and Tetanus Toxins*, (Dirk W. Dressler & Joseph J. Jankovic eds., 2003); Giovanna Lalli et al., *The Journey of Tetanus and Botulinum Neurotoxins in Neurons*, 11 (9) Trends Microbiol. 431-437, (2003).

The three-dimensional crystal structures of BoNT/A indicate that the three functional domains of the toxin are structurally distinct, see e.g., Humeau et al., supra, (2000), Turton et al, supra, (2002); and Lalli et al., supra, (2003). The HEXXH consensus motif of the light chain forms the tetrahedral zinc binding pocket of the catalytic site located in a deep cleft on the protein surface that is accessible by a channel. This conserved zinc binding motif binds at least one zinc atom necessary for its catalytic function. The structure of the $H_N$ and $H_C$ domains consists primarily of β-sheet topologies that are linked by a single α-helix. The $H_N$ domain comprises a β-barrel, jelly-roll fold that resembles the carbohydrate binding moiety found in lectins suggesting that this domain may recognize oligosaccharide-containing molecules and play a role in the intracellular sorting. In addition to its overall structural similarity with lectins, the $H_N$ domain also contains two distinct structural features suggesting functions. First, the $H_N$ domain contains a pair of long amphipathic helices that resemble the coiled-coil motif found in some viral proteins. In viruses, these helices assist in fusing the viral membrane to the cellular membrane of the host, suggesting that the coiled-coil region may assist in inserting the $H_N$ domain into the membrane of an intracellular vesicle. Second, a long loop called the 'translocation belt,' wraps around a large negatively charged cleft of the light chain that blocks zinc access of the zinc atom to the catalytic-binding pocket of active site. The $H_C$ domain contains a ganglioside-binding site and a five residue ganglioside-binding motif. These regions adopt a modified β-trefoil fold structure which forms four distinct carbohydrate binding regions believed to mediate the binding to specific carbohydrate containing acceptor molecules on the cell surface. Consistent with this function, the $H_C$ domain exhibits the highest sequence divergence between clostridial toxins which may account for the distinct binding properties and sorting schemes of TeNT and BoNTs. The $H_C$ domain tilts away from the $H_N$ domain exposing the surface loops and making them accessible for binding. No contact seems to occur between the light chain and the $H_C$ domain. The N-terminus of the $H_C$ region presents a jelly-roll architecture related to that of the S-lectins, a carbohydrate-binding family of proteins. By contrast, the C-terminus of $H_C$ is in a pseudo threefold trefoil conformation that presents structural similarity to the sequentially unrelated interleukins-1α and 1β, Kunitz-type trypsin inhibitors, as well as fibroblast growth factors (FGF). These proteins, mostly β-proteins, are involved in protein-protein interactions.

Cell surface gangliosides appear to be part of the receptor system for BoNT/A and appear to participate in binding of the toxin to its BoNT/A receptor. Although toxin binding is not strictly dependent on the presence of gangliosides, the presence of specific gangliosides appears to be required for high affinity binding. In particular, BoNTs have been observed to interact in vitro and in vivo with polysialogangliosides, especially those of the G1b series (GD1a, GD1b, GD3, GQ1b, or GT1b), see, e.g., Jane L. Halpern & Elaine A. Neale, Neurospecific binding, internalization, and retrograde axonal transport, 195 Curr. Top. Microbiol. Immunol. 221-241 (1995). Preincubation of the toxin with these gangliosides protects the neuromuscular junction (NMJ) of mice from BoNT toxicity. High-affinity, trypsin-sensitive, BoNT-binding sites were found in isolated synaptosomes, see, e.g., R. S. Williams et al, Radioiodination of *botulinum* neurotoxin type A with retention of biological activity and its binding to brain synaptosomes. 131(2) Eur. J. Biochem. 1437-1445 (1983). Since lectins with high affinity for sialic acid antagonize the binding of BoNTs, their protein receptors may be glycoproteins. Receptors for BoNTs would direct them to acidic vesicles allowing the translocation of the LC into the cytosol of the neuron. The amino acid sequence at the C-terminus of $H_C$ is poorly conserved among different clostridial neurotoxins, and competition experiments have shown that different BoNT serotypes bind to different protein receptors on the surface of neuronal cells. This analysis is therefore consistent with the hypothesis that BoNTs neurotoxins bind to receptor systems comprising at least two components; a protein component and a carbohydrate component.

Based on these findings, and as the present disclosure provided herein, the Applicants have discovered that cells expressing the fibroblast growth factor receptor 3 (FGFR3) can bind BoNT/A. Internalization of the toxin can be followed when these cell lines are exposed to the toxin. Moreover, BoNT/A internalization is inhibited in a dose-dependent manner when FGF, such as, e.g., FGF1, FGF2, FGF4, FGF8 and FGF9, is added at increasing concentrations. Cells tested by the Applicants that did not display the FGFR3 receptor were unable to internalize the toxin, although when subjected to electroporation in the presence of BoNT/A, the intracellular cleavage of SNAP-25 could be detected, indicating that the endopeptidase activity of the toxin remained intact, and that the cells remained susceptible to the endopeptidase. In addition, the Applicants have found that pre-treatment with the polysialoganglioside GT1b increases BoNT/A cellular uptake.

Fibroblast growth factors (FGF) participate in many developmental, differentiation and growth and repair processes of cells through complex combinatorial signaling pathways. Presently, at least 23 ligands (FGF1-23) are known to signal through a family of five transmembrane tyrosine kinase FGF receptors (FGFR1-5). The amino acid sequence identity is highly conserved between FGFR family members and each share a characteristic structural organization. The extracellular portion of FGFRs comprise an amino-terminal hydrophocic signal peptide, three Ig-like domains (IgI, IgII and IgIII) and an acid box domain of approximately eight acidic residues, followed by a single hydrophobic transmembrane domain, which in turn is followed by an intracellular tyrosine kinase domain (see FIG. 2). Affinity of FGFRs for their ligands is highly diverse with different affinities for each family member of growth factors, see, e.g., C. J. Powers et al., Fibroblast growth factors, their receptors and signaling 7(3) Endocr. Relat. Cancer. 165-197 (2000). Table 1 lists some of the known FGF-FGFR signaling relationships of various FGFs and their FGFRs.

TABLE 1

| | FGFR Variants | | | | | | | |
|---|---|---|---|---|---|---|---|---|
| | FGFR1 | | FGFR2 | | FGFR3 | | | |
| Variant | IIIb | IIIc | IIIb | IIIc | IIIb | IIIc | FGFR4 | FGFR5 |
| Ligands | FGF-1 FGF-2 FGF-3 FGF-8 FGF-10 | FGF-1 FGF-2 FGF-4 FGF-5 FGF-6 FGF-8 FGF-17 | FGF-1 FGF-3 FGF-7 FGF-10 | FGF-1 FGF-2 FGF-4 FGF-5 FGF-6 FGF-8 FGF-9 FGF-17 | FGF-1 FGF-9 | FGF-1 FGF-2 FGF-4 FGF-8 FGF-9 | FGF-1 FGF-2 FGF-4 FGF-6 FGF-8 FGF-9 | FGF-1 FGF-2 |
| Tissues | Brain, bone, kidney, skin, lung, heart, muscle, neuron | | Brain, kidney, skin, lung, liver, glial cells | | Brain, CNS, kidney, skin, lung, testis | | Lung, liver, kidney | Brain, skin, lung, testis |

Table 1—FGFR variants and ligand affinities. FGFR variants, associated ligands, and tissue distribution, see, e.g., Powers et al, supra, (2000); and Reuss & von Bohlen und Halbach, supra, (2003).

Diversity in FGF signaling beyond the five receptors is achieved in part by the generation of alternatively spliced variants encoding distinct receptor isoforms, see, e.g., Bernhard Reuss & Oliver von Bohlen und Halbach, Fibroblast growth factors and their receptors in the central nervous system, 313(2) Cell Tissue Res. 139-157 (2003). The protein region that appears to have the highest influence on ligand binding specificity is a portion of the IgIII domain, for which isoforms encoded by three different splice variants have been identified. These three isoforms, designated IgIIIa, IgIIIb and IgIIIc, have relative binding affinities for different FGFR family members. Alternative splicing in the FGFR ligand binding domain, designated a and b, generates additional receptor isoforms with novel ligand affinities. Isoforms for IgIIIa, IgIIIb and IgIIIc have been identified for both FGFR1 and FGFR2. Thus far, the IgIIIa isoform of FGFR3 and the IgIIIa and IgIIIb isoforms of FGFR4 and FGFR5 have not been reported.

Figure 2:
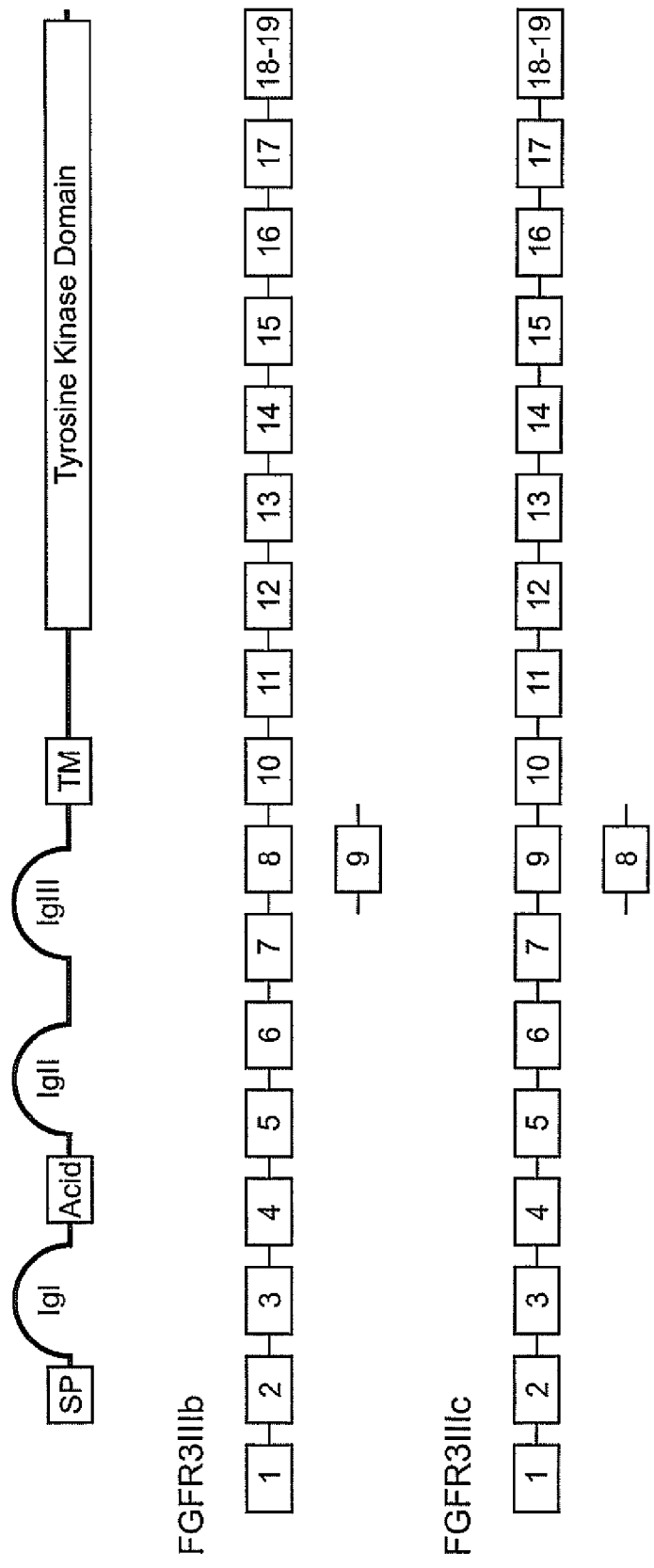
FIG. 2 shows a schematic of an FGFR3 and the alternatively spliced exons that result in FGFR3IIIb and FGFR3IIIc. The top diagram shows a generalized drawing of a FGFR3. The extracellular domain comprises a signal peptide (box labeled SP), three Ig-like domains (loops labeled IgI, IgII and IgIII) and an acid box (box labeled acid). A single membrane spanning region comprises the transmembrane domain (box labeled TM). The cytoplasmic portion of the receptor comprises the tyrosine kinase domain. The middle diagram shows a generalized drawing of the exons encoding a FGFR3IIIb isoform, where exon 9 is spliced out from the primary transcript during processing. The lower diagram shows a generalized drawing of the exons encoding a FGFR3IIIc isoform, where exon 8 is spliced out from the primary transcript during processing.
Figure 3A:
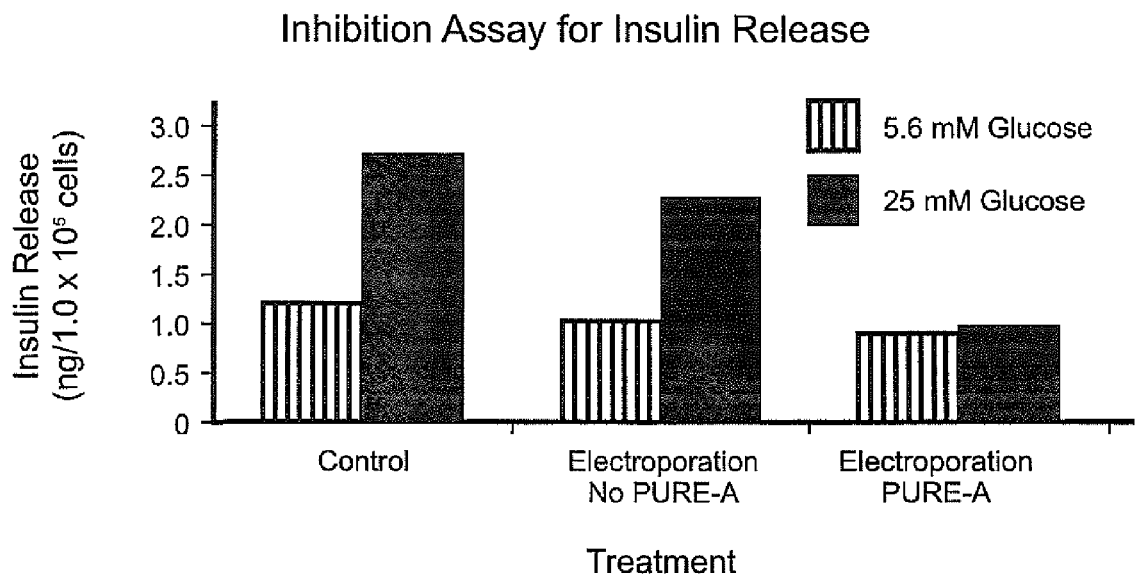
FIG. 3a shows the results of an inhibition of insulin release assay. The graph indicates that the addition of glucose to 25 mM induced insulin secretion from untreated cells (control) and cells subjected to electroporation without the addition of PURE-A (Electroporation No PURE-A). However, HIT-T15 cells into which PURE-A was introduced (Electroporation PURE-A) showed a decrease in insulin secretion from indicating these cells were unresponsive to induction of insulin secretion.
Figure 3B:
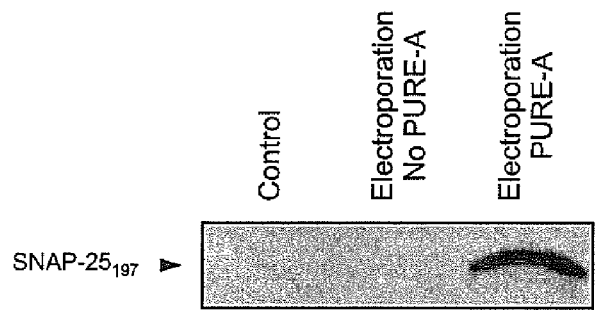
FIG. 3b shows the results of a SNAP-25 cleavage assay. Western blot analysis identified the presence of a BoNT/A SNAP-$25_{197}$ cleavage product in PURE-A treated cells (Electroporation PURE-A), but not in either control (Control and Electroporation No PURE-A), with equal amounts of protein loaded per lane and probed with an antibody that detects the BoNT/A SNAP-$25_{197}$ cleavage product.

As mentioned above, FGFR3 commonly exists in two isoforms, FGFR3IIIc and FGFR3IIIb, which arise following alternative splicing of the primary transcript in which either exon 8 or 9 respectively is skipped (see FIG. 2). However, additional isoforms exist. For example, an FGFR3 isoform has been described which lacks the acid box, see, e.g., Akio Shimizu et al, A novel alternatively spliced fibroblast growth factor receptor 3 isoform lacking the acid box domain is expressed during chondrogenic differentiation of ATDC5 cells, 276(14) J. Biol. Chem. 11031-11040 (2001). In another example, a novel, secreted isoform was recently identified, called FGFR3S, in which exons 8, 9 and 10 are spliced out creating a FGFR3 that lacks the second half of Igilic and the transmembrane domain, see, e.g., L-M. Sturla et al., FGFR3IIIS: a novel soluble FGFR3 spliced variant that modulates growth is frequently expressed in tumour cells, 89(7) Br. J. Cancer 1276-1284 (2003).

Aspects of the present invention provide, in part, a method of detecting BoNT/A activity by contacting a sample to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an embodiment, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment a method of detecting BoNT/A activity comprises contacting a sample to a cell that stably contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

As used herein "*botulinum* toxin serotype A" is synonymous with "BoNT/A," "type A," or similar terminology referring unambiguously to *Clostridium botulinum* neurotoxin type A, means any of a number of polypeptide neurotoxins, and derivatives thereof, which can be purified from *Clostridium botulinum* serotype A strains and which share FGFR3 as a cell surface receptor. Such neurotoxins include those found in or corresponding to the following strains and accession numbers listed in Table 2.

TABLE 2

| Strain | Accession No. |
|---|---|
| CL138 | AAQ16535 |
| 137 | AAQ16534 |
| 129 | AAQ16533 |
| 13 | AAQ16532 |
| 42N | AAQ16531 |
| Hall A-hyper | AAM75961 |
| 667Ab | CAA61124 |
| NCTC 2916 | CAA36289 |
| Allergan-Hall A | AAQ06331 |
| 62A | AAA23262 |
| Kyoto-F | CAA51824 |
| type A NIH | BAA11051 |
| NCTC 7272 | |
| 7I03-H | |
| Kumgo | AAO21363 |

As used herein, the term "Fibroblast Growth Factor 3 Receptor" is synonymous with "FGFR3" and means a FGFR3 peptide or peptidomimetic which binds BoNT/A in a manner that elicits a BoNT/A intoxication response. FGFR3s useful in the invention encompass, without limitation, wild type FGFR3s, naturally occurring FGFR3 variants, non-naturally FGFR3 variants, such as, e.g., genetically engineered variants produced by random mutagenesis or rational designed, and active fragments derived from a FGFR3s. As a non-limiting example, a human FGFR3, naturally occurring human FGFR3 variants, non-naturally human FGFR3 variants, and human FGFR3 fragments that retain the ability to selectively bind BoNT/A and mediate the intoxication process, can be useful as a BoNT/A receptor in aspects of the present invention. In another non-limiting example, a bovine FGFR3, naturally occurring bovine FGFR3 variants, non-naturally bovine FGFR3 variants, and bovine FGFR3 fragments that retain the ability to selectively bind BoNT/A and mediate the intoxication process, can be useful as a BoNT/A receptor in aspects of the present invention. In another non-limiting example, a rat FGFR3, naturally occurring rat FGFR3 variants, non-naturally rat FGFR3 variants, and rat FGFR3 fragments that retain the ability to selectively bind BoNT/A and mediate the intoxication process, can be useful as a BoNT/A receptor in aspects of the present invention. In still another non-limiting example, a mouse FGFR3, naturally occurring mouse FGFR3 variants, non-naturally mouse FGFR3 variants, and mouse FGFR3 fragments that retain the ability to selectively bind BoNT/A and mediate the intoxication process, can be useful as a BoNT/A receptor in aspects of the present invention. In another non-limiting example, a chicken FGFR3, naturally occurring chicken FGFR3 variants, non-naturally chicken FGFR3 variants, and chicken FGFR3 fragments that retain the ability to selectively bind BoNT/A and mediate the intoxication process, can be useful as a BoNT/A receptor in aspects of the present invention. In another non-limiting example, a frog FGFR3, naturally occurring frog FGFR3 variants, non-naturally frog FGFR3 variants, and frog FGFR3 fragments that retain the ability to selectively bind BoNT/A and mediate the intoxication process, can be useful as a BoNT/A receptor in aspects of the present invention. In another non-limiting example, a newt FGFR3, naturally occurring newt FGFR3 variants, non-naturally newt FGFR3 variants, and newt FGFR3 fragments that retain the ability to selectively bind BoNT/A and mediate the intoxication process, can be useful as a BoNT/A receptor in aspects of the present invention. In another non-limiting example, a zebrafish FGFR3, naturally occurring zebrafish FGFR3 variants, non-naturally zebrafish FGFR3 variants, and zebrafish FGFR3 fragments that retain the ability to selectively bind BoNT/A and mediate the intoxication process, can be useful as a BoNT/A receptor in aspects of the present invention. In is also understood that both nucleic acid molecules, such as, e.g., DNA and RNA, that encode a FGFR3 disclosed in the present specification and peptide molecules or peptidomimetics comprising a FGFR3 disclosed in the present specification are useful in aspects of the present invention. SEQ ID NO: 1, 3, 5, 7, 9, 11, 13, 15, 17, 19, 21, 23, 25 and 27 disclose nucleic acid molecules encoding representative of FGFR3s useful in aspects on the present invention, while SEQ ID NO: 2, 4, 6, 8, 10, 12, 14, 16, 18, 20, 22, 24, 26 and 28 disclose peptide molecules representative of FGFR3s useful in aspects on the present invention.

As used herein, the term "peptidomimetic" is used broadly to mean a peptide-like molecule that selectively binds BoNT/A as the peptide BoNT/A receptor upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and selectively bind BoNT/A as the peptide substrate upon which the peptidomimetic is derived, see, e.g., Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$—$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; β-substituted-2,3-methano amino acid; an $NC^\delta$ or $C^\alpha$—$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Thus, in aspects of this embodiment, the FGFR3 can be a human FGFR3IIIb that selectively binds BoNT/A which has, e.g., at least 70% amino acid identity with the FGFR3 of SEQ ID NO: 2, at least 75% amino acid identity with the FGFR3 of SEQ ID NO: 2, at least 80% amino acid identity with the FGFR3 of SEQ ID NO: 2, at least 85% amino acid identity with the FGFR3 of SEQ ID NO: 2, at least 90% amino acid identity with the FGFR3 of SEQ ID NO: 2 or at least 95% amino acid identity with the FGFR3 of SEQ ID NO: 2. In other aspects of this embodiment, the FGFR3 is a human FGFR3IIIb that that selectively binds BoNT/A which has, e.g., at most one, two, three, four, five, six, seven, eight, nine, or ten amino acid substitutions relative to the FGFR3 of SEQ ID NO: 2.

In other aspects of this embodiment, the FGFR3 can be a human FGFR3IIIc that selectively binds BoNT/A which has, e.g., at least 70% amino acid identity with the FGFR3 of SEQ ID NO: 4, at least 75% amino acid identity with the FGFR3 of SEQ ID NO: 4, at least 80% amino acid identity with the FGFR3 of SEQ ID NO: 4, at least 85% amino acid identity with the FGFR3 of SEQ ID NO: 4, at least 90% amino acid identity with the FGFR3 of SEQ ID NO: 4 or at least 95% amino acid identity with the FGFR3 of SEQ ID NO: 4. In other aspects of this embodiment, the FGFR3 is a human FGFR3IIIc that that selectively binds BoNT/A which has, e.g., at most one, two, three, four, five, six, seven, eight, nine, or ten amino acid substitutions relative to the FGFR3 of SEQ ID NO: 4.

In other aspects of this embodiment, the FGFR3 can be a human FGFR3IIIS that selectively binds BoNT/A which has, e.g., at least 70% amino acid identity with the FGFR3 of SEQ ID NO: 6, at least 75% amino acid identity with the FGFR3 of SEQ ID NO: 6, at least 80% amino acid identity with the FGFR3 of SEQ ID NO: 6, at least 85% amino acid identity with the FGFR3 of SEQ ID NO: 6, at least 90% amino acid identity with the FGFR3 of SEQ ID NO: 6 or at least 95% amino acid identity with the FGFR3 of SEQ ID NO: 6. In other aspects of this embodiment, the FGFR3 is a human FGFR3IIIS that that selectively binds BoNT/A which has, e.g., at most one, two, three, four, five, six, seven, eight, nine, or ten amino acid substitutions relative to the FGFR3 of SEQ ID NO: 6.

In other aspects of this embodiment, the FGFR3 can be a bovine FGFR3IIIc that selectively binds BoNT/A which has, e.g., at least 70% amino acid identity with the FGFR3 of SEQ ID NO: 8, at least 75% amino acid identity with the FGFR3 of SEQ ID NO: 8, at least 80% amino acid identity with the FGFR3 of SEQ ID NO: 8, at least 85% amino acid identity with the FGFR3 of SEQ ID NO: 8, at least 90% amino acid identity with the FGFR3 of SEQ ID NO: 8 or at least 95% amino acid identity with the FGFR3 of SEQ ID NO: 8. In other aspects of this embodiment, the FGFR3 is a bovine FGFR3IIIc that that selectively binds BoNT/A which has, e.g., at most one, two, three, four, five, six, seven, eight, nine, or ten amino acid substitutions relative to the FGFR3 of SEQ ID NO: 8.

In other aspects of this embodiment, the FGFR3 can be a mouse FGFR3IIIb that selectively binds BoNT/A which has, e.g., at least 70% amino acid identity with the FGFR3 of SEQ ID NO: 10, at least 75% amino acid identity with the FGFR3 of SEQ ID NO: 10, at least 80% amino acid identity with the FGFR3 of SEQ ID NO: 10, at least 85% amino acid identity with the FGFR3 of SEQ ID NO: 10, at least 90% amino acid identity with the FGFR3 of SEQ ID NO: 10 or at least 95% amino acid identity with the FGFR3 of SEQ ID NO: 10. In other aspects of this embodiment, the FGFR3 is a mouse FGFR3IIIc that selectively binds BoNT/A which has, e.g., at most one, two, three, four, five, six, seven, eight, nine, or ten amino acid substitutions relative to the FGFR3 of SEQ ID NO: 10.

In other aspects of this embodiment, the FGFR3 can be a mouse FGFR3IIIc that selectively binds BoNT/A which has, e.g., at least 70% amino acid identity with the FGFR3 of SEQ ID NO: 12, at least 75% amino acid identity with the FGFR3 of SEQ ID NO: 12, at least 80% amino acid identity with the FGFR3 of SEQ ID NO: 12, at least 85% amino acid identity with the FGFR3 of SEQ ID NO: 12, at least 90% amino acid identity with the FGFR3 of SEQ ID NO: 12 or at least 95% amino acid identity with the FGFR3 of SEQ ID NO: 12. In other aspects of this embodiment, the FGFR3 is a mouse FGFR3IIIc that that selectively binds BoNT/A which has, e.g., at most one, two, three, four, five, six, seven, eight, nine, or ten amino acid substitutions relative to the FGFR3 of SEQ ID NO: 12.

In other aspects of this embodiment, the FGFR3 can be a mouse FGFR3-delAcid that selectively binds BoNT/A which has, e.g., at least 70% amino acid identity with the FGFR3 of SEQ ID NO: 14, at least 75% amino acid identity with the FGFR3 of SEQ ID NO: 14, at least 80% amino acid identity with the FGFR3 of SEQ ID NO: 14, at least 85% amino acid identity with the FGFR3 of SEQ ID NO: 14, at least 90% amino acid identity with the FGFR3 of SEQ ID NO: 14 or at least 95% amino acid identity with the FGFR3 of SEQ ID NO: 14. In other aspects of this embodiment, the FGFR3 is a mouse FGFR3-delAcid that that selectively binds BoNT/A which has, e.g., at most one, two, three, four, five, six, seven, eight, nine, or ten amino acid substitutions relative to the FGFR3 of SEQ ID NO: 14.

In other aspects of this embodiment, the FGFR3 can be a rat FGFR3IIIb that selectively binds BoNT/A which has, e.g., at least 70% amino acid identity with the FGFR3 of SEQ ID NO: 16, at least 75% amino acid identity with the FGFR3 of SEQ ID NO: 16, at least 80% amino acid identity with the FGFR3 of SEQ ID NO: 16, at least 85% amino acid identity with the FGFR3 of SEQ ID NO: 16, at least 90% amino acid identity with the FGFR3 of SEQ ID NO: 16 or at least 95% amino acid identity with the FGFR3 of SEQ ID NO: 16. In other aspects of this embodiment, the FGFR3 is a rat FGFR3IIIb that that selectively binds BoNT/A which has, e.g., at most one, two, three, four, five, six, seven, eight, nine, or ten amino acid substitutions relative to the FGFR3 of SEQ ID NO: 16.

In other aspects of this embodiment, the FGFR3 can be a rat FGFR3IIIc that selectively binds BoNT/A which has, e.g., at least 70% amino acid identity with the FGFR3 of SEQ ID NO: 18, at least 75% amino acid identity with the FGFR3 of SEQ ID NO: 18, at least 80% amino acid identity with the FGFR3 of SEQ ID NO: 18, at least 85% amino acid identity with the FGFR3 of SEQ ID NO: 18, at least 90% amino acid identity with the FGFR3 of SEQ ID NO: 18 or at least 95% amino acid identity with the FGFR3 of SEQ ID NO: 18. In other aspects of this embodiment, the FGFR3 is a rat FGFR3IIIc that that selectively binds BoNT/A which has, e.g., at most one, two, three, four, five, six, seven, eight, nine, or ten amino acid substitutions relative to the FGFR3 of SEQ ID NO: 18.

In other aspects of this embodiment, the FGFR3 can be a chicken FGFR3 that selectively binds BoNT/A which has, e.g., at least 70% amino acid identity with the FGFR3 of SEQ ID NO: 20, at least 75% amino acid identity with the FGFR3 of SEQ ID NO: 20, at least 80% amino acid identity with the FGFR3 of SEQ ID NO: 20, at least 85% amino acid identity with the FGFR3 of SEQ ID NO: 20, at least 90% amino acid identity with the FGFR3 of SEQ ID NO: 20 or at least 95% amino acid identity with the FGFR3 of SEQ ID NO: 20. In other aspects of this embodiment, the FGFR3 is a chicken FGFR3 that that selectively binds BoNT/A which has, e.g., at most one, two, three, four, five, six, seven, eight, nine, or ten amino acid substitutions relative to the FGFR3 of SEQ ID NO: 20.

In other aspects of this embodiment, the FGFR3 can be a frog FGFR3-1 that selectively binds BoNT/A which has, e.g., at least 70% amino acid identity with the FGFR3 of SEQ ID NO: 22, at least 75% amino acid identity with the FGFR3 of SEQ ID NO: 22, at least 80% amino acid identity with the FGFR3 of SEQ ID NO: 22, at least 85% amino acid identity with the FGFR3 of SEQ ID NO: 22, at least 90% amino acid identity with the FGFR3 of SEQ ID NO: 22 or at least 95% amino acid identity with the FGFR3 of SEQ ID NO: 22. In other aspects of this embodiment, the FGFR3 is a frog FGFR3 that that selectively binds BoNT/A which has, e.g., at most one, two, three, four, five, six, seven, eight, nine, or ten amino acid substitutions relative to the FGFR3 of SEQ ID NO: 22.

In other aspects of this embodiment, the FGFR3 can be a frog FGFR3-2 that selectively binds BoNT/A which has, e.g., at least 70% amino acid identity with the FGFR3 of SEQ ID NO: 24, at least 75% amino acid identity with the FGFR3 of SEQ ID NO: 24, at least 80% amino acid identity with the FGFR3 of SEQ ID NO: 24, at least 85% amino acid identity with the FGFR3 of SEQ ID NO: 24, at least 90% amino acid identity with the FGFR3 of SEQ ID NO: 24 or at least 95% amino acid identity with the FGFR3 of SEQ ID NO: 24. In other aspects of this embodiment, the FGFR3 is a frog FGFR3 that that selectively binds BoNT/A which has, e.g., at most one, two, three, four, five, six, seven, eight, nine, or ten amino acid substitutions relative to the FGFR3 of SEQ ID NO: 24.

In other aspects of this embodiment, the FGFR3 can be a newt FGFR3 that selectively binds BoNT/A which has, e.g., at least 70% amino acid identity with the FGFR3 of SEQ ID NO: 26, at least 75% amino acid identity with the FGFR3 of SEQ ID NO: 26, at least 80% amino acid identity with the FGFR3 of SEQ ID NO: 26, at least 85% amino acid identity with the FGFR3 of SEQ ID NO: 26, at least 90% amino acid identity with the FGFR3 of SEQ ID NO: 26 or at least 95% amino acid identity with the FGFR3 of SEQ ID NO: 26. In other aspects of this embodiment, the FGFR3 is a newt FGFR3 that that selectively binds BoNT/A which has, e.g., at most one, two, three, four, five, six, seven, eight, nine, or ten amino acid substitutions relative to the FGFR3 of SEQ ID NO: 26.

In other aspects of this embodiment, the FGFR3 can be a zebrafish FGFR3 that selectively binds BoNT/A which has, e.g., at least 70% amino acid identity with the FGFR3 of SEQ ID NO: 28, at least 75% amino acid identity with the FGFR3 of SEQ ID NO: 28, at least 80% amino acid identity with the FGFR3 of SEQ ID NO: 28, at least 85% amino acid identity with the FGFR3 of SEQ ID NO: 28, at least 90% amino acid identity with the FGFR3 of SEQ ID NO: 28 or at least 95% amino acid identity with the FGFR3 of SEQ ID NO: 28. In other aspects of this embodiment, the FGFR3 is a zebrafish FGFR3 that that selectively binds BoNT/A which has, e.g., at most one, two, three, four, five, six, seven, eight, nine, or ten amino acid substitutions relative to the FGFR3 of SEQ ID NO: 28.

Aspects of the present invention provide, in part, a method of detecting BoNT/A activity by contacting a sample to a cell that contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an embodiment, a method of detecting BoNT/A activity comprises contacting a sample to a cell that transiently contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment a method of detecting BoNT/A activity comprises contacting a sample to a cell that stably contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

As used herein, the term "synaptic vesicle glycoprotein 2" is synonymous with "SV2" and means a SV2 peptide or peptidomimetic which associates with FGFR3 in a manner that enhances BoNT/A binding, thereby eliciting a BoNT/A intoxication response. SV2s useful in the invention encompass, without limitation, wild type SV2s, naturally occurring SV2s variants, non-naturally SV2s variants, such as, e.g., genetically engineered variants produced by random mutagenesis or rational designed, and active fragments derived from a SV2s. In addition, any SV2 which associates with FGFR3 in a manner that enhances BoNT/A binding, thereby eliciting a BoNT/A intoxication response can be useful in practicing aspect of this invention, including, without limitation, vertebrate SV2s, such as, e.g., mammalian SV2s, bird SV2s, amphibian SV2s, and fish SV2s, and invertebrate SV2s, such as, e.g., insect SV2s and worm SV2s. As a non-limiting example, a human SV2, naturally occurring human SV2 variants, non-naturally human SV2 variants, and human SV2 fragments that retain the ability to selectively associate with FGFR3 in a manner that enhances BoNT/A binding, thereby mediating the intoxication process, can be useful as a BoNT/A receptor in aspects of the present invention. In another non-limiting example, a primate SV2, naturally occurring primate SV2 variants, non-naturally primate SV2 variants, and primate SV2 fragments that retain the ability to selectively associate with FGFR3 in a manner that enhances BoNT/A binding, thereby mediating the intoxication process, can be useful as a BoNT/A receptor in aspects of the present invention. In another non-limiting example, a bovine SV2, naturally occurring bovine SV2 variants, non-naturally bovine SV2 variants, and bovine SV2 fragments that retain the ability to selectively associate with FGFR3 in a manner that enhances BoNT/A binding, thereby mediating the intoxication process, can be useful as a BoNT/A receptor in aspects of the present invention. In another non-limiting example, a rat SV2, naturally occurring rat SV2 variants, non-naturally rat SV2 variants, and rat SV2 fragments that retain the ability to selectively associate with FGFR3 in a manner that enhances BoNT/A binding, thereby mediating the intoxication process, can be useful as a BoNT/A receptor in aspects of the present invention. In another non-limiting example, a mouse SV2, naturally occurring mouse SV2 variants, non-naturally mouse SV2 variants, and mouse SV2 fragments that retain the ability to selectively associate with FGFR3 in a manner that enhances BoNT/A binding, thereby mediating the intoxication process, can be useful as a BoNT/A receptor in aspects of the present invention.

Cell compositions comprising a FGFR3 and a SV2 can enhance the selective binding of BoNT/A relative to a composition not containing a SV2. Non-limiting examples of a SV2 include a SV2A, a SV2B, and a SV2C. Other non-limiting examples of a SV2 include SEQ ID NO: 33, SEQ ID NO: 34, SEQ ID NO: 35, and SEQ ID NO: 36. Thus, in an embodiment, a composition comprises a FGFR3 and a SV2. In aspects of this embodiment, a composition comprises a FGFR3 and a SV2, such as, e.g., a SV2A, a SV2B, a SV2C, or any combination thereof. In aspects of this embodiment, a composition comprises a FGFR3 and a SV2, such as, e.g., SEQ ID NO: 33, SEQ ID NO: 34, SEQ ID NO: 35, SEQ ID NO: 36, or any combination thereof.

Thus, in an embodiment, the methods disclosed in the present invention comprise a SV2 that enhances the selective binding of BoNT/A. in aspects of this embodiment, a SV2 that enhances the selective binding of BoNT/A has, e.g., at least 70% amino acid identity with the SV2 of SEQ ID NO: 33, SEQ ID NO: 34, SEQ ID NO: 35, or SEQ ID NO: 36, at least 75% amino acid identity with the SV2 of SEQ ID NO: 33, SEQ ID NO: 34, SEQ ID NO: 35, or SEQ ID NO: 36, at least 80% amino acid identity with the FGFR3 of SEQ ID NO: 2, at least 85% amino acid identity with the SV2 of SEQ ID NO: 33, SEQ ID NO: 34, SEQ ID NO: 35, or SEQ ID NO: 36, at least 90% amino acid identity with the FGFR3 of SEQ ID NO: 2 or at least 95% amino acid identity with the SV2 of SEQ ID NO: 33, SEQ ID NO: 34, SEQ ID NO: 35, or SEQ ID NO: 36. In other aspects of this embodiment, the SV2 that selectively binds BoNT/A has, e.g., at most one, two, three, four, five, six, seven, eight, nine, or ten amino acid substitutions relative to the SEQ ID NO: 33, SEQ ID NO: 34, SEQ ID NO: 35, or SEQ ID NO: 36.

In other aspects of this embodiment, a SV2 that enhances the selective binding of BoNT/A has, e.g., at least one, two or three non-contiguous amino acid substitutions relative to SEQ ID NO: 33, SEQ ID NO: 34, SEQ ID NO: 35, or SEQ ID NO: 36. In other aspects of this embodiment, a SV2 that enhances the selective binding of BoNT/A has, e.g., at most one, two or three non-contiguous amino acid substitutions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at least one, two or three non-contiguous amino acid deletions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at most one, two or three non-contiguous amino acid deletions relative to SEQ ID NO: 33, SEQ ID NO: 34, SEQ ID NO: 35, or SEQ ID NO: 36. In still other aspects of this embodiment, a SV2 that enhances the selective binding of BoNT/A has, e.g., at least one, two or three non-contiguous amino acid additions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at most one, two or three non-contiguous amino acid additions relative to SEQ ID NO: 33, SEQ ID NO: 34, SEQ ID NO: 35, or SEQ ID NO: 36.

In other aspects of this embodiment, a SV2 that enhances the selective binding of BoNT/A has, e.g., at least one, two or three contiguous amino acid substitutions relative to SEQ ID NO: 33, SEQ ID NO: 34, SEQ ID NO: 35, or SEQ ID NO: 36. In other aspects of this embodiment, a SV2 that enhances the selective binding of BoNT/A has, e.g., at most one, two or three contiguous amino acid substitutions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at least one, two or three contiguous amino acid deletions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at most one, two or three contiguous amino acid deletions relative to SEQ ID NO: 33, SEQ ID NO: 34, SEQ ID NO: 35, or SEQ ID NO: 36. In still other aspects of this embodiment, a SV2 that enhances the selective binding of BoNT/A has, e.g., at least one, two or three contiguous amino acid additions relative to SEQ ID NO: 33, SEQ ID NO: 34, SEQ ID NO: 35, or SEQ ID NO: 36. In yet other aspects of this embodiment, a SV2 that enhances the selective binding of BoNT/A has, e.g., at most one, two or three contiguous amino acid additions relative to SEQ ID NO: 33, SEQ ID NO: 34, SEQ ID NO: 35, or SEQ ID NO: 36.

Other aspects of the present invention provide, in part, the optional use of a polysialogangliosides, especially those of the G1b series, such as, e.g., GD1a, GD1b, GD3, GQ1b, or GT1b. Cell compositions comprising a FGFR3 and a polysialoganglioside can increase the selective binding of BoNT/A relative to a composition not containing a polysialoganglioside. Thus, in an embodiment, a composition comprises a FGFR3 and optionally a polysialoganglioside. In aspects of this embodiment, a composition comprises a FGFR3 and optionally a G1b polysialoganglioside, such as, e.g., GD1a, GD1b, GD3, GQ1b, or GT1b.

Thus, in an embodiment, a method of detecting BoNT/A activity comprises contacting a sample to a cell that contains an exogenous FGFR3 and optionally a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment, a method of detecting BoNT/A activity comprises contacting a sample to a cell that transiently contains an exogenous FGFR3 and a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment a method of detecting BoNT/A activity comprises contacting a sample to a cell that stably contains an exogenous FGFR3 and a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspects of the present invention provide, in part, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspects of the present invention provide, in part, a method of detecting BoNT/A activity comprises contacting a sample to a cell that transiently contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. As used herein, the term "transiently containing" means a FGFR3, a SV2, or both a FGFR3 and a SV2 that is temporarily introduced into a cell in order to perform the assays disclosed in the present specification. Thus, aspects of a cell transiently containing a FGFR3, a SV2, or both a FGFR3 and a SV2 disclosed in the specification can include a cell that contains a FGFR3, a SV2, or both a FGFR3 and a SV2 for, e.g., at most about one day, at most about two days, at most about three days, at most about four days, at most about five days, and at most about six days, at most about seven days, at most about eight days, at most about nine days and at most about ten days.

In an aspect of this embodiment, the FGFR3 can be encoded by the nucleic acid molecule from a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In an aspect of this embodiment, a method of detecting BoNT/A activity comprises contacting a sample to a cell that transiently contains a nucleic acid molecule encoding an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains a nucleic acid molecule encoding an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that transiently contains a nucleic acid molecule encoding an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains a nucleic acid molecule encoding an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. Thus in an embodiment, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In an aspect of this embodiment, a method of detecting BoNT/A activity comprises contacting a sample to a cell that transiently contains an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that transiently contains an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In an aspect of this embodiment, a SV2 can be encoded by the nucleic acid molecule, such as, e.g., those encoding for a SV2A, a SV2B, or a SV2C. In other aspects of this embodiment, a SV2 can be encoded by the nucleic acid molecule, such as, e.g., those encoding for SEQ ID NO: 33, SEQ ID NO: 34, SEQ ID NO: 35, or SEQ ID NO: 36. In an aspect of this embodiment, a method of detecting BoNT/A activity comprises contacting a sample to a cell that transiently contains a nucleic acid molecule encoding an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, a SV2 can be, such as, e.g., a SV2A, a SV2B or a SV2C. In other aspects of this embodiment, a SV2 can be, such as, e.g., SEQ ID NO: 33, SEQ ID NO: 34, SEQ ID NO: 35, or SEQ ID NO: 36. In another aspect of this embodiment, a method of detecting BoNT/A activity comprises contacting a sample to a cell that transiently contains an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspects of the present invention provide, in part, a method of detecting BoNT/A activity comprises contacting a sample to a cell that stably contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspect of the present invention provide, in part, a method of detecting BoNT/A activity comprises contacting a sample to a cell that stably contains an exogenous FGFR3, an exogenous SV2, or both an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. As used herein, the term "stably containing" means a FGFR3, a SV2, or a both a FGFR3 and a SV2 that is introduced into a cell and maintained for long periods of time in order to perform the assays of the present specification. Stably-maintained nucleic acid molecules encompass stably-maintained nucleic acid molecules that are extra-chromosomal and replicate autonomously and stably-maintained nucleic acid molecules that are integrated into the chromosomal material of the cell and replicate non-autonomously. Thus aspects of a cell stably containing a FGFR3, a SV2, or a both a FGFR3 and a SV2 disclosed in the specification may include a cell that contains a FGFR3, a SV2, or a both a FGFR3 and a SV2 for, e.g., at least ten days, at least 20 two days, at least 30 days, at least forty days, at least 50 days, and at least 60 days, at least 70 days, at least 80 days, at least 90 days and at least 100 days. Other aspects of a cell stably containing a FGFR3, a SV2, or a both a FGFR3 and a SV2 disclosed in the specification may include a cell that contains a FGFR3, a SV2, or a both a FGFR3 and a SV2 for, e.g., at least 100 days, at least 200 days, at least 300 days, at least 400 days, and at least 500 days. Still other aspects of a cell stably containing a FGFR3, a SV2, or a both a FGFR3 and a SV2 disclosed in the specification may include a cell that permanently contains a FGFR3, a SV2, or a both a FGFR3 and a SV2.

In an aspect of this embodiment, the FGFR3 can be encoded by the nucleic acid molecule from a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In an aspect of this embodiment, a method of detecting BoNT/A activity comprises contacting a sample to a cell that stably contains a nucleic acid molecule encoding an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains a nucleic acid molecule encoding an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that stably contains a nucleic acid molecule encoding an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains a nucleic acid molecule encoding an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In an aspect of this embodiment, a method of detecting BoNT/A activity comprises contacting a sample to a cell that stably contains an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that stably contains an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In an aspect of this embodiment, a SV2 can be encoded by the nucleic acid molecule, such as, e.g., those encoding for a SV2A, a SV2B, or a SV2C In other aspects of this embodiment, a SV2 can be encoded by the nucleic acid molecule, such as, e.g., those encoding for SEQ ID NO: 33, SEQ ID NO: 34, SEQ ID NO: 35, or SEQ ID NO: 36 In an aspect of this embodiment, a method of detecting BoNT/A activity comprises contacting a sample to a cell that stably contains a nucleic acid molecule encoding an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, a SV2 can be, such as, e.g., a SV2A, a SV2B, or a SV2C. In another aspect of this embodiment, a SV2 can be, such as, e.g., SEQ ID NO: 33, SEQ ID NO: 34, SEQ ID NO: 35, or SEQ ID NO: 36. In another aspect of this embodiment, a method of detecting BoNT/A activity comprises contacting a sample to a cell that stably contains an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

As mentioned above, a nucleic acid molecule can be used to express a FGFR3 and/or a SV2 disclosed in the present specification. It is envisioned that any and all methods for introducing a nucleic acid molecule into a cell can be used. Methods useful for introducing a nucleic acid molecule into a cell including, without limitation, calcium phosphate-mediated, DEAE dextran-mediated, lipid-mediated, polybrene-mediated, polylysine-mediated, viral-mediated, microinjection, protoplast fusion, biolistic, electroporation and conjugation to an antibody, gramacidin S, artificial viral envelope or other intracellular carrier such as TAT, see, e.g., Introducing Cloned Genes into Cultured Mammalian Cells, pp. 16.1-16.62 (Sambrook & Russell, eds., Molecular Cloning A Laboratory Manual, Vol. 3, $3^{rd}$ ed. 2001); Alessia Colosimo et al., Transfer and expression of foreign genes in mammalian cells, 29(2) Biotechniques 314-318, 320-322, 324 (2000); Philip Washbourne & A. Kimberley McAllister, Techniques for gene transfer into neurons, 12(5) Curr. Opin. Neurobiol. 566-573 (2002); and Current Protocols in Molecular Biology, John Wiley and Sons, pp 9.16.4-9.16.11 (2000). One skilled in the art understands that selection of a specific method to introduce a nucleic acid molecule into a cell will depend, in part, on whether the cell will transiently contain a BoNT/A receptor or whether the cell will stably contain a BoNT/A receptor.

As mentioned above, a FGFR3 and/or SV2 disclosed in the present specification can be introduced into a cell. It is envisioned that any and all methods using a delivery agent to introduce a FGFR3 and/or a SV2 into a cell can be used. As used herein, the term "delivery agent" means any molecule that enables or enhances internalization of a covalently-linked, non-covalently-linked or in any other manner associated with a FGFR3 and/or a SV2 into a cell. Thus, the term "delivery agent" encompasses, without limitation, proteins, peptides, peptidomimetics, small molecules, nucleic acid molecules, liposomes, lipids, viruses, retroviruses and cells that, without limitation, transport a covalently or non-covalently linked substrate to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent useful in the invention also can be an agent that enables or enhances cellular uptake of a covalently linked FGFR3 and/or a SV2, such as, e.g., by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308 (Jun. 15, 2000); Gérard Chassaing & Alain Prochiantz, Peptides which can be Used as Vectors for the Intracellular Addressing of Active Molecules, U.S. Pat. No. 6,080,724 (Jun. 27, 2000); Alan Frankel et al., Fusion Protein Comprising TAT-derived Transport Moiert, U.S. Pat. No. 5,674,980 (Oct. 7, 1995); Alan Frankel et al., TAT-derived Transport Polypeptide Conjugates, U.S. Pat. No. 5,747,641 (May 5, 1998); Alan Frankel et al., TAT-derived Transport Polypeptides and Fusion Proteins, U.S. Pat. No. 5,804,604 (Sep. 8, 1998); Peter F. J. O'Hare et al., Use of Transport Proteins, U.S. Pat. No. 6,734,167 (May 11, 2004); Yao-Zhong Lin & Jack J. Hawiger, Method for importing biologically active molecules into cells, U.S. Pat. No. 5,807,746 (Sep. 15, 1998); Yao-Zhong Lin & Jack J. Hawiger, Method for importing biologically active molecules into cells, U.S. Pat. No. 6,043,339 (Mar. 28, 2000); Yao-Zhong Lin et al., Sequence and Method for Genetic Engineering of Proteins with Cell Membrane Translocating Activity, U.S. Pat. No. 6,248,558 (Jun. 19, 2001); Yao-Zhong Lin et al., Sequence and Method for Genetic Engineering of Proteins with Cell Membrane Translocating Activity, U.S. Pat. No. 6,432,680 (Aug. 13, 2002); Jack J. Hawiger et al., Method for importing biologically active molecules into cells, U.S. Pat. No. 6,495,518 (Dec. 17, 2002); Yao-Zhong Lin et al., Sequence and Method for Genetic Engineering of Proteins with Cell Membrane Translocating Activity, U.S. Pat. No. 6,780,843 (Aug. 24, 2004); Jonathan B. Rothbard & Paul A Wender, Method and Composition for Enhancing Transport Across Biological Membranes, U.S. Pat. No. 6,306,993 (Oct. 23, 2001); Jonathan B. Rothbard & Paul A Wender, Method and Composition for Enhancing Transport Across Biological Membranes, U.S. Pat. No. 6,495,663 (Dec. 17, 2002); and Pamela B. Davis et al., Fusion proteins for protein delivery, U.S. Pat. No. 6,287,817 (Sep. 11, 2001).

A delivery agent useful in the invention also can be an agent that enables or enhances cellular uptake of a non-covalently associated FGFR3 and/or a SV2. Methods that function in the absence of covalent linkage and methods of using such agents are described in, e.g., Gilles Divita et al, Peptide-mediated Transfection Agents and Methods of Use, U.S. Pat. No. 6,841,535 (Jan. 11, 2005); Philip L Feigner and Olivier Zelphati, Intracellular Protein Delivery Compositions and Methods of Use, U.S. Patent Publication No. 2003/0008813); and Michael Karas Intracellular Delivery of Small Molecules, Proteins and Nucleic Acids, U.S. Patent Publication 2004/0209797 (Oct. 21, 2004). Such peptide delivery agents can be prepared and used by standard methods and are commercially available, see, e.g. the Chariot™ Reagent (Active Motif, Carlsbad, Calif.); BioPORTER® Reagent (Gene Therapy Systems, Inc., San Diego, Calif.), BioTrek™ Protein Delivery Reagent (Stratagene, La Jolla, Calif.), and Pro-Ject™ Protein Transfection Reagent (Pierce Biotechnology Inc., Rockford, Ill.).

As mentioned above, a cell can stably contain a FGFR3, a SV2, or both a FGFR3 and a SV2 disclosed in the present specification. Methods useful for making and using a cells that stably contain a FGFR3, a SV2, or both a FGFR3 and a SV2 are described in, e.g., Elizabeth E. Plowright et al., Ectopic expression of fibroblast growth factor receptor 3 promotes myeloma cell proliferation and prevents apoptosis, 95(3) Blood 992-998 (2000); TC, see, e.g., Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999); M. Kana et al., Signal transduction pathway of human fibroblast growth factor receptor 3. Identification of a novel 66-kDa phosphoprotein, 272(10) J. Biol. Chem. 6621-6628 (1997); and Janet E. Henderson et al., Expression of FGFR3 with the G380R achondroplasia mutation inhibits proliferation and maturation of CFK2 chondrocytic cells, 15(1) J. Bone Miner. Res. 155-165 (2000).

Another aspect of the present invention provides, in part, an expression construct that allow for expression of a nucleic acid molecule encoding a FGFR3 and/or a SV2 disclosed in the present specification. These expression constructs comprise an open reading frame encoding a FGFR3 and/or a SV2 disclosed in the present specification, operably-linked to control sequences from an expression vector useful for expressing a FGFR3 and/or a SV2 in a cell. The term "operably linked" as used herein, refers to any of a variety of cloning methods that can ligate a nucleic acid molecule disclosed in the present specification into an expression vector such that a peptide encoded by the composition is expressed when introduced into a cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, nucleic acid ligation, bacterial transformation, nucleic acid purification, nucleic acid sequencing are routine procedures well within the scope of one skilled in the art and from the teaching herein. Non-limiting examples of specific protocols necessary to make an expression construct are described in e.g., MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). These protocols are routine procedures well within the scope of one skilled in the art and from the teaching herein.

A wide variety of expression vectors can be employed for expressing an open reading frame encoding a FGFR3 and/or a SV2 and include without limitation, viral expression vectors, prokaryotic expression vectors and eukaryotic expression vectors including yeast, insect and mammalian expression vectors. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing construct compositions disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and E. coli extracts. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins*, 80(9) CURRENT SCIENCE 1121-1128, (2001). These protocols are routine procedures well within the scope of one skilled in the art and from the teaching herein.

An expression construct comprising a nucleic acid molecule encoding a FGFR3 and/or a SV2 disclosed in the present specification can be operationally-linked to a variety of regulatory elements that can positively or negatively modulate, either directly or indirectly, the expression of a nucleic acid molecule, such as, e.g., constitutive, tissue-specific, inducible or synthetic promoters and enhancers. Non-limiting examples of constitutive regulatory elements include, e.g., the cytomegalovirus (CMV), herpes simplex virus thymidine kinase (HSV TK), simian virus 40 (SV40) early, 5' long terminal repeat (LTR), elongation factor-1α (EF-1α) and polybiquitin (UbC) regulatory elements. Non-limiting examples of inducible regulatory elements useful in aspects of the present invention include, e.g., chemical-inducible regulatory elements such as, without limitation, alcohol-regulated, tetracycline-regulated, steroid-regulated, metal-regulated and pathogenesis-related; and physical-inducible regulatory elements such as, without limitation, temperature-regulated and light-regulated. Such inducible regulatory elements can be prepared and used by standard methods and are commercially available, including, without limitation, tetracycline-inducible and tetracycline-repressible elements such as, e.g., Tet-On™ and Tet-Off™ (BD Biosciences-Clontech, Palo Alto, Calif.) and the T-REx™ (Tetracycline-Regulated Expression) and Flp-In™ T-REx™ systems (Invitrogen, Inc., Carlsbad, Calif.); ecdysone-inducible regulatory elements such as, e.g., the Complete Control® Inducible Mammalian Expression System (Stratagene, Inc., La Jolla, Calif.); isopropyl β-D-galactopyranoside (IPTG)-inducible regulatory elements such as, e.g., the LacSwitch® $^{II}$ Inducible Mammalian Expression System (Stratagene, Inc., La Jolla, Calif.); and steroid-inducible regulatory elements such as, e.g., the chimeric progesterone receptor inducible system, GeneSwitch™ (Invitrogen, Inc., Carlsbad, Calif.). The skilled person understands that these and a variety of other constitutive and inducible regulatory systems are commercially available or well known in the art and can be useful in the invention for controlling expression of a nucleic acid molecule which encodes a BoNT/A receptor.

In an embodiment, a nucleic acid molecule encoding a FGFR3 can optionally be linked to a regulatory element such as a constitutive regulatory element. In aspects of this embodiment, a nucleic acid molecule encoding a mammalian FGFR3 can optionally be linked to a regulatory element such as a constitutive regulatory element; a nucleic acid molecule encoding a bird FGFR3 can optionally be linked to a regulatory element such as a constitutive regulatory element; a nucleic acid molecule encoding an amphibian FGFR3 can optionally be linked to a regulatory element such as a constitutive regulatory element; and a nucleic acid molecule encoding a fish FGFR3 can optionally be linked to a regulatory element such as a constitutive regulatory element.

In another embodiment, a nucleic acid molecule encoding a FGFR3 can optionally be linked to a regulatory element such as an inducible regulatory element. In aspects of this embodiment, a nucleic acid molecule encoding a mammalian FGFR3 can optionally be linked to a regulatory element such as a inducible regulatory element; a nucleic acid molecule encoding a bird FGFR3 can optionally be linked to a regulatory element such as a inducible regulatory element; a nucleic acid molecule encoding an amphibian FGFR3 can optionally be linked to a regulatory element such as a inducible regulatory element; and a nucleic acid molecule encoding a fish FGFR3 can optionally be linked to a regulatory element such as a inducible regulatory element. In another aspect of this embodiment, expression of the nucleic acid molecule is induced using, e.g., tetracycline-inducible, ecdysone-inducible or steroid-inducible.

In an embodiment, a nucleic acid molecule encoding a SV2 can optionally be linked to a regulatory element such as a constitutive regulatory element. In another embodiment, a nucleic acid molecule encoding a SV2 can optionally be linked to a regulatory element such as an inducible regulatory element. In another aspect of this embodiment, expression of the nucleic acid molecule encoding a SV2 is induced using, e.g., tetracycline-inducible, ecdysone-inducible or steroid-inducible.

It is understood that a FGFR3 and/or a SV2 useful in aspects of the present invention optionally can include one or more additional components. As a non-limiting example, a flexible spacer sequence such as poly-glycine sequences can be included in a FGFR3 and/or a SV2 useful in the invention. A useful FGFR3 and/or a SV2 can further include, without limitation, one or more of the following: epitope-binding tags, such as. e.g., FLAG, Express™, human Influenza virus hemagluttinin (HA), human p62$^{c\text{-}Myc}$ protein (c-MYC), Vesicular Stomatitis Virus Glycoprotein (VSV-G), glycoprotein-D precursor of Herpes simplex virus (HSV), V5, and AU1; affinity-binding, such as. e.g., polyhistidine (HIS), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein; immunoglobulin hinge region; an N-hydroxysuccinimide linker; a peptide or peptidomimetic hairpin turn; or a hydrophilic sequence or another component or sequence that, for example, promotes the solubility or stability of a FGFR3. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual Portable Protocol No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Aspects of the present invention provide, in part, a cell that contains an exogenous FGFR3 wherein said cell is capable of being intoxicated by a BoNT/A; or a cell that contains an exogenous SV2 wherein said cell is capable of BoNT/A intoxication; or a cell that contains an exogenous FGFR3 and an exogenous SV2 wherein said cell is capable of BoNT/A intoxication. As used herein, the term "cell," means any eukaryotic cell that expresses at least one endogenous FGFR3, or can be engineered to express, at least one exogenous FGFR3 that binds BoNT/A. Such cells can optionally express at least one endogenous SV2, or can be engineered to express, at least one exogenous SV2. The term cell encompasses cells from a variety of organisms, such as, e.g., murine, rat, porcine, bovine, equine, primate and human cells; from a variety of cell types such as, e.g., neural and non-neural; and can be isolated from or part of a heterogeneous cell population, tissue or organism. It is understood that cells useful in aspects of the invention can included, without limitation, primary cells; cultured cells; established cells; normal cells; transformed cells; tumor cells; infected cells; proliferating and terminally differentiated cells; and stably or transiently transfected cells, including stably and transiently transfected cells. It is further understood that cells useful in aspects of the invention can be in any state such as proliferating or quiescent; intact or permeabilized such as through chemical-mediated transfection such as, e.g., calcium phosphate-mediated, diethyl-laminoethyl (DEAE) dextran-mediated, lipid-mediated, polyethyleneimine (PEI)-mediated, polybrene-mediated, and protein delivery agents; physical-mediated transfection, such as, e.g., biolistic particle delivery, micro-injection and electroporation; and viral-mediated transfection, such as, e.g., retroviral-mediated transfection. It is further understood that cells useful in aspects of the invention may include those which express a FGFR3 or a SV2 under control of a constitutive, tissue-specific, cell-specific or inducible promoter element, enhancer element or both.

As used herein, the term "cell capable of BoNT/A intoxication" means a cell that can enable the overall cellular mechanism whereby BoNT/A proteolytically cleaves a substrate, such as, e.g., SNAP-25, and encompasses the binding of BoNT/A to a low or high affinity receptor, the internalization of the toxin/receptor complex, the translocation of the BoNT/A light chain into the cytoplasm and the enzymatic target modification of a BoNT/A substrate. By definition, a cell capable of BoNT/A intoxication must express a FGFR3. As a non-limiting example, a neuronal or non-neuronal cell can be transiently or stably engineered to express an exogenous nucleic acid molecule encoding a FGFR3. As another non-limiting limiting example, a neuronal or non-neuronal cell can be transiently engineered to contain an exogenous FGFR3. As yet another non-limiting example, a neuronal or non-neuronal cell can be transiently or stably engineered to express an exogenous nucleic acid molecule encoding a SV2. As yet another non-limiting example, a neuronal or non-neuronal cell can be transiently engineered to contain an exogenous SV2. Other examples of useful cells include, without limitation, a neuronal or non-neuronal cell comprising an endogenous FGFR3 that is transiently or stably engineered to express an exogenous nucleic acid molecule encoding a SV2; a neuronal or non-neuronal cell comprising an endogenous FGFR3 that is transiently or stably engineered to express an exogenous SV2; a neuronal or non-neuronal cell comprising an endogenous SV2 that is transiently or stably engineered to express an exogenous nucleic acid molecule encoding a FGFR3; a neuronal or non-neuronal cell comprising an endogenous SV2 that is transiently or stably engineered to express an exogenous FGFR3; a neuronal or non-neuronal cell comprising an endogenous FGFR3 and an endogenous SV2; and a neuronal or non-neuronal cell that is transiently or stably engineered to express an exogenous FGFR3 and an exogenous SV2. In all the above combinations, a neuronal or non-neuronal cell can further comprise a ganglioside.

Cells useful in aspects of the invention include both neuronal and non-neuronal cells. Neuronal cells useful in aspects of the invention include, without limitation, primary neuronal cells; immortalized or established neuronal cells; transformed neuronal cells; neuronal tumor cells; stably and transiently transfected neuronal cells and further include, yet are not limited to, mammalian, murine, rat, primate and human neuronal cells. Non-limiting examples of neuronal cells useful in aspects of the invention include, e.g., peripheral neuronal cells, such as, e.g., motor neurons and sensory neurons; and CNS neuronal cells, such as, e.g., spinal cord neurons like embryonic spinal cord neurons, dorsal root ganglia (DRG) neurons, cerebral cortex neurons, cerebellar neurons, hippocampal neurons and motor neurons. Neuronal cells useful in the invention can be, for example, central nervous system (CNS) neurons; neuroblastoma cells; motor neurons, hippocampal neurons or cerebellar neurons and further can be, without limitation, Neuro-2A, SH-SY5Y, NG108-15, N1E-115 or SK-N-DZ cells. The skilled person understands that these and additional primary and established neurons can be useful in the cells and methods of the invention.

Neurons useful in aspects of the invention include, without limitation, primary cultures such as primary cultures of embryonic dorsal root ganglion (DRG) neurons. As one example, primary cultures of embryonic rat DRG neurons are described in Mary J. Welch et al., Sensitivity of embryonic rat dorsal root ganglia neurons to *Clostridium botulinum* neurotoxins, 38(2) Toxicon 245 258 (2000); and primary cultures of fetal spinal cord neurons, for example, primary cultures of murine fetal spinal cord neurons are described in Elaine A. Neale et al., *Botulinum* neurotoxin A blocks synaptic vesicle exocytosis but not endocytosis at the nerve terminal, 147(6) J. Cell Biol. 1249-1260 (1999), and John A. Chaddock et al., Inhibition of vesicular secretion in both neuronal and non-neuronal cells by a retargeted endopeptidase derivative of *Clostridium botulinum* neurotoxin type A, 68(5) Infect. Immun. 2587-2593 (2000). Thus, in an embodiment, a cell capable of BoNT/A intoxication can be a neuron that contains an exogenous FGFR3. In aspects of this embodiment, a neuron can be a neuron from, e.g., a primary culture, an embryonic dorsal root ganglion primary culture or a fetal spinal cord primary culture. As non-limiting examples, cells useful according to a method disclosed in the present specification can include, a primary neuronal cell that contains an exogenous FGFR3, an exogenous SV2, or an exogenous FGFR3 and an exogenous SV2, such as, e.g., a rat embryonic dorsal root ganglion (DRG) neuron that contains an exogenous FGFR3, an exogenous SV2, or an exogenous FGFR3 and an exogenous SV2 or a murine fetal spinal cord neuron that contains an exogenous FGFR3, an exogenous SV2, or an exogenous FGFR3 and an exogenous SV2.

Neuronal cell lines useful in aspects of the invention include, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines.

Neuroblastoma cell lines, such as, e.g., murine, rat, primate or human neuroblastoma cell lines can be useful in aspects of the invention. Neuroblastoma cell lines useful in aspects of the invention include, without limitation, BE(2)-C (ATCC CRL-2268; ECACC 95011817), BE(2)-M17 (ATCC CRL-2267; ECACC 95011816), C1300 (ECACC 93120817), CHP-212 (ATCC CRL-2273), CHP-126 (DSMZ ACC 304), IMR 32 (ATCC CRL-127; ECACC 86041809; DSMZ ACC 165), KELLY (ECACC 92110411; DSMZ ACC 355), LA-N-2, see, e.g., Robert C. Seeger et al., Morphology, growth, chromosomal pattern and fibrinolytic activity of two new human neuroblastoma cell lines, 37(5) Cancer Res. 1364-1371 (1977); and G. J. West et al., Adrenergic, cholinergic, and inactive human neuroblastoma cell lines with the action-potential Na+ ionophore, 37(5) Cancer Res. 1372-1376 (1977), MC-IXC (ATCC CRL-2270), MHH-NB-11 (DSMZ ACC 157), N18Tg2 (DSMZ ACC 103), N1E-115 (ATCC CCL-2263; ECACC 88112303), N4TG3 (DSMZ ACC 101), Neuro-2A (ATCC CCL-131; ECACC 89121404; DSMZ ACC 148), NB41A3 (ATCC CCL-147; ECACC 89121405), NS20Y (DSMZ ACC 94), SH-SY5Y (ATCC CRL-2266; ECACC 94030304; DSMZ ACC 209), SIMA (DSMZ ACC 164), SK-N-DZ (ATCC CRL-2149; ECACC 94092305), SK-N-F1 (ATCC CRL-2142, ECACC 94092304), SK-N-MC (ATCC HTB-10, DSMZ ACC 203) and SK-N-SH (ATCC HTB-11, ECACC 86012802). Thus, in an embodiment, a cell capable of BoNT/A intoxication can be a neuroblastoma cell that contains an exogenous FGFR3, an exogenous SV2, or an exogenous FGFR3 and an exogenous SV2. In aspects of this embodiment, a neuroblastoma cell can be, e.g., BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH. As non-limiting examples, cells useful for detecting BoNT/A activity according to a method disclosed in the present specification can include, a neuroblastoma cell that contains an exogenous FGFR3, an exogenous SV2, or an exogenous FGFR3 and an exogenous SV2, such as, e.g., a SH-SY5Y cell that contains an exogenous FGFR3, an exogenous SV2, or an exogenous FGFR3 and an exogenous SV2; a Neuro-2a cell that contains an exogenous FGFR3, an exogenous SV2, or an exogenous FGFR3 and an exogenous SV2; and a N1E-115 cell that contains an exogenous FGFR3; and a SK-N-DZ cell that contains an exogenous FGFR3, an exogenous SV2, or an exogenous FGFR3 and an exogenous SV2.

Neuronal hybrid cell lines, such as, e.g., murine, rat, primate and human hybrid neuronal cell lines can be useful in aspects of the invention. Such hybrid cell lines include neuroblastoma/glioma hybrids, such as, e.g., N18 (ECACC 88112301), NG108-15 (ATCC HB-12317, ECACC 88112302) and NG115-401L (ECACC 87032003); neuroblastoma/motor neuron hybrids, such as, e.g., NSC-19 and NSC-34, which express motor neuron characteristics, display a multipolar neuron-like phenotype, express high levels of choline acetyltransferase (CHAT), generate action potentials, express neurofilament triplet proteins and synthesize, store and release acetylcholine, see, e.g., N. R. Cashman et al., Neuroblastoma×spinal cord (NSC) hybrid cell lines resemble developing motor neurons, 194(3) Dev. Dyn. 209-221 (1992); and Christopher J. Eggett et al., Development and characterisation of a glutamate-sensitive motor neuronal cell line, 74(5) J. Neurochem. 1895-1902 (2000); neuroblastoma/root ganglion neuron hybrids, such as, e.g., F11, see, e.g., Doros Platika et al., Neuronal traits of clonal cell lines derived by fusion of dorsal root ganglia neurons with neuroblastoma cells, 82(10) Proc. Natl. Acad. Sci. U.S.A. 3499-3503 (1985), ND-E (ECACC 92090915), ND-U1 (ECACC 92090916), ND7/23 (ECACC 92090903), ND8/34 (ECACC 92090904) and ND27 (ECACC 92090912); neuroblastoma/hippocampal neuron hybrids, such as, e.g., HN-33, see, e.g., Henry J. Lee et al., Neuronal properties and trophic activities of immortalized hippocampal cells from embryonic and young adult mice. 10(6) J. Neurosci. 1779-1787 (1990). Thus, in an embodiment, a cell capable of BoNT/A toxin intoxication can be a hybrid neuron that contains an exogenous FGFR3, an exogenous SV2, or an exogenous FGFR3 and an exogenous SV2. In aspects of this embodiment, a hybrid neuron can be, e.g., a neuroblastoma/glioma hybrid cell that contains an exogenous FGFR3, an exogenous SV2, or an exogenous FGFR3 and an exogenous SV2, a neuroblastoma/motor neuron hybrid cell that contains an exogenous FGFR3, an exogenous SV2, or an exogenous FGFR3 and an exogenous SV2, a neuroblastoma/root ganglion neuron hybrid cell that contains an exogenous FGFR3, an exogenous SV2, or an exogenous FGFR3 and an exogenous SV2 and a neuroblastoma/hippocampal neuron hybrid cell that contains an exogenous FGFR3, an exogenous SV2, or an exogenous FGFR3 and an exogenous SV2. In further aspects of this embodiment, a neuroblastoma/glioma hybrid can be, e.g., N18, NG108-15 and NG115-401L. In further aspects of this embodiment, a neuroblastoma/motor neuron hybrid can be, e.g., NSC-19 and NSC-32. In further aspects of this embodiment, a neuroblastoma/root ganglion neuron hybrid can be, e.g., F11, ND-E, ND-U1, ND7/23, ND8/34 and ND27. In further aspects of this embodiment, a neuroblastoma/hippocampal neuron hybrid can be, e.g., HN-33. As non-limiting examples, cells useful for detecting BoNT/A activity according to a method disclosed in the present specification can include, a neuronal hybrid cell, such as, e.g., a NG108-15 cell that contains an exogenous FGFR3, an exogenous SV2, or an exogenous FGFR3 and an exogenous SV2.

Spinal cord cell lines, such as, e.g., murine, rat, primate or human spinal cord cell lines can be useful in aspects of the invention and include, without limitation, TE 189.T (ATCC CRL-7947) and M4b, see, e.g., Ana M. Cardenas et al., Establishment and characterization of immortalized neuronal cell lines derived from the spinal cord of normal and trisomy 16 fetal mice, an animal model of Down syndrome, 68(1) J. Neurosci. Res. 46-58 (2002). As an example, a human spinal cord cell line can be generated from precursors of human embryonic spinal cord cells (first trimester embryos) that are immortalized with a tetracycline repressible v-myc oncogene as described in Ronghao Li et al., Motoneuron differentiation of immortalized human spinal cord cell lines, 59(3) J. Neurosci. Res. 342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP 2 and choline acetyltransferase, and can release acetylcholine upon appropriate stimulation, see, e.g., Cardenas et al., supra, (2002). Thus, in an embodiment, a cell capable of BoNT/A intoxication can be a spinal cord cell that contains an exogenous FGFR3, an exogenous SV2, or an exogenous FGFR3 and an exogenous SV2. In aspects of this embodiment, a spinal cord cell that contains an exogenous FGFR3, an exogenous SV2, or an exogenous FGFR3 and an exogenous SV2 can be, e.g., a TE 189.T cell that contains an exogenous FGFR3, an exogenous SV2, or an exogenous FGFR3 and an exogenous SV2 and a M4b cell that contains an exogenous FGFR3, an exogenous SV2, or an exogenous FGFR3 and an exogenous SV2.

Central nervous system (CNS) cell lines, such as, e.g., murine, rat, primate and human CNS cell lines, can be useful in aspects of the invention. A useful CNS cell line can be, for example, a human CNS cell line immortalized with a tetracycline repressible v-myc oncogene as described in Dinah W. Sah et al., Bipotent progenitor cell lines from the human CNS, 15(6) Nat. Biotechnol. 574-580 (1997). Upon repression of the oncogene, the cells differentiate into neurons. Thus, in an embodiment, a cell capable of BoNT/A intoxication can be a CNS cell that contains an exogenous FGFR3, an exogenous SV2, or an exogenous FGFR3 and an exogenous SV2.

Cerebral cortex cell lines, such as, e.g., murine, rat, primate and human cerebral cortex cell lines, can be useful in aspects of the invention and include, without limitation, CNh, see, e.g., Ana M. Cardenas et al., Calcium signals in cell lines derived from the cerebral cortex of normal and trisomy 16 mice, 10(2) Neuroreport 363-369 (1999), HCN-1a (ATCC CRL-10442) and HCN-2 (ATCC CRL-10742). As an example, murine cortex primary cultures from 12-16 days embryos can be immortalized, for example, by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation, see, e.g., David D. Allen et al., Impaired cholinergic function in cell lines derived from the cerebral cortex of normal and trisomy 16 mice, 12(9) Eur. J. Neurosci. 3259-3264 (2000). Thus, in an embodiment, a cell capable of BoNT/A intoxication can be a cerebral cortex cell that contains an exogenous FGFR3, an exogenous SV2, or an exogenous FGFR3 and an exogenous SV2. In aspects of this embodiment, a cerebral cortex cell that contains an exogenous FGFR3, an exogenous SV2, or an exogenous FGFR3 and an exogenous SV2 can be, e.g., a CNh cell that contains an exogenous FGFR3, an exogenous SV2, or an exogenous FGFR3 and an exogenous SV2, HCN-1a cell that contains an exogenous FGFR3, an exogenous SV2, or an exogenous FGFR3 and an exogenous SV2 and HCN-2 cell that contains an exogenous FGFR3, an exogenous SV2, or an exogenous FGFR3 and an exogenous SV2.

Dorsal root ganglia cell lines, such as, e.g., murine, rat, primate and human dorsal root ganglia cell lines, can be useful in aspects of the invention and include, without limitation, G4b, see, e.g., David D. Allen et al., A dorsal root ganglia cell line derived from trisomy 16 fetal mice, a model for Down syndrome, 13(4) Neuroreport 491-496 (2002). Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine, see, e.g., Allen et al., supra, (2002). Thus, in an embodiment, a cell capable of BoNT/A intoxication can be a dorsal root ganglia cell that contains an exogenous FGFR3, an exogenous SV2, or an exogenous FGFR3 and an exogenous SV2. In aspects of this embodiment, a dorsal root ganglia cell can be, e.g., a G4b cell that contains an exogenous FGFR3, an exogenous SV2, or an exogenous FGFR3 and an exogenous SV2.

Hippocampal cell lines, such as, e.g., murine, rat, primate and human hippocampal lines can be useful in aspects of the invention and include, without limitation, HT-4, see, e.g., K. Frederiksen et al., Immortalization of precursor cells from the mammalian CNS, 1(6) Neuron 439-448 (1988) and HT-22, see, e.g., John B. Davis and Pamela Maher, Protein kinase C activation inhibits glutamate-induced cytotoxicity in a neuronal cell line, 652(1) Brain Res. 169-173 (1994). As a non-limiting example, the murine hippocampal cell line HT-22 can be useful in the invention. As a further non-limiting example, the immortalized HN33 hippocampal cell line can be useful in the invention. This hippocampal cell line was derived from the fusion of primary neurons from the hippocampus of postnatal day 21 mice with the N18TG2 neuroblastoma cell line, and, when differentiated, shares membrane properties with adult hippocampal neurons in primary culture, see, e.g., Henry J. Lee et al., Neuronal Properties and Trophic Activities of Immortalized Hippocampal Cells from Embryonic and Young Adult Mice, 19(6) J. Neurosci. 1779-1787 (1990); and Henry J. Lee et al., Immortalized young adult neurons from the septal region: generation and characterization, 52(1-2) Brain Res. Dev Brain Res. 219-228 (1990). Thus, in an embodiment, a cell capable of BoNT/A intoxication can be a hippocampal cell that contains an exogenous FGFR3, an exogenous SV2, or an exogenous FGFR3 and an exogenous SV2. In aspects of this embodiment, a hippocampal cell that contains an exogenous FGFR3, an exogenous SV2, or an exogenous FGFR3 and an exogenous SV2 can be, e.g., a HT-4 cell that contains an exogenous FGFR3, an exogenous SV2, or an exogenous FGFR3 and an exogenous SV2, a HT-22 cell that contains an exogenous FGFR3, an exogenous SV2, or an exogenous FGFR3 and an exogenous SV2 and a HN33 cell that contains an exogenous FGFR3, an exogenous SV2, or an exogenous FGFR3 and an exogenous SV2.

A variety of non-neuronal cells are useful in aspects of the invention. Non-neuronal cells useful in aspects of the invention include, without limitation, primary non-neuronal cells; immortalized or established non-neuronal cells; transformed non-neuronal cells; non-neuronal tumor cells; stably and transiently transfected non-neuronal cells and further include, yet are not limited to, mammalian, murine, rat, primate and human non-neuronal cells. Non-neuronal cells useful in aspects of the invention further include, without limitation, any of the following primary or established cells: anterior pituitary cells; adrenal cells, such as. e.g., chromaffin cells of the adrenal medulla; pancreatic cells, such as. e.g., pancreatic acinar cells, pancreatic islet β cells and insulinoma HIT or INS-1 cells; ovarian cells, such as. e.g., steroid-producing ovarian cells; kidney cells, such as. e.g., inner medullary collecting duct (IMCD) cells; stomach cells, such as, e.g., enterochromaffin cells; blood cells, such as. e.g., eurythrocytes, leucocytes, platelets, neutrophils, eosinophils, mast cells; epithelial cells, such as. e.g., those of the apical plasma membrane; fibroblasts; thyroid cells; chondrocytes; muscle cells; hepatocytes; glandular cells such as, e.g., pituitary cells, adrenal cells, chromaffin cells; and cells involved in glucose transporter (GLUT4) translocation. Thus, in an embodiment, a cell capable of BoNT/A intoxication can be a non-neuronal cell. In aspects of this embodiment, a non-neuronal cell can be from a primary or established non-neuronal cell line from the, e.g., anterior pituitary cells, adrenal cells, pancreatic cells, ovarian cells, kidney cells, stomach cells, blood cells, epithelial cells, fibroblasts, thyroid cells, chondrocytes, muscle cells, hepatocytes and glandular cells.

As non-limiting examples, cells useful for detecting BoNT/A activity according to a method disclosed in the present specification can include, a primary or established non-neuronal cell that contains an exogenous FGFR3, an exogenous SV2, or an exogenous FGFR3 and an exogenous SV2, such as, e.g., a chromaffin cell that contains an exogenous FGFR3, an exogenous SV2, or an exogenous FGFR3 and an exogenous SV2 or pancreatic acinar cell that contains an exogenous FGFR3, an exogenous SV2, or an exogenous FGFR3 and an exogenous SV2.

As discussed above, cells useful in the invention include neuronal and non-neuronal cells that express low or undetectable levels of endogenous receptor but which have been transfected with, or otherwise engineered to express, one or more exogenous nucleic acid molecules encoding one or more FGFR3s and/or SV2. Cells useful in aspects of the present invention further include, without limitation, transformed, tumor or other cells which over-express one or more exogenous FGFR3s and/or one or more exogenous SV2s. It is understood that the over-expressed receptor can be a wild type form of the receptor or can include one or more amino acid modifications as compared to the wild type receptor, with the proviso that the process of BoNT/A intoxication can still occur. As a non-limiting example, cells useful for detecting BoNT/A activity encompass those which express or over-express an exogenous mammalian FGFR3, such as, e.g., a human FGFR3, a bovine FGFR3, a rat FGFR3 or a mouse FGFR3. As another non-limiting example, cells useful for detecting BoNT/A activity encompass those which express or over-express an exogenous bird FGFR3, such as, e.g., chicken FGFR3. As another non-limiting example, cells useful for detecting BoNT/A activity encompass those which express or over-express an exogenous amphibian FGFR3, such as, e.g., a newt FGFR3 or a frog FGFR3. As another non-limiting example, cells useful for detecting BoNT/A activity encompass those which express or over-express an exogenous fish FGFR3, such as, e.g., a zebrafish FGFR3. As yet another non-limiting example, cells useful for detecting BoNT/A activity encompass those which express or over-express an exogenous SV2, such as, e.g., a SV2A, a SV2B, or a SV2C.

Thus, in an embodiment, a cell capable of BoNT/A intoxication can be a cell stably expressing an exogenous FGFR3, an exogenous SV2, or an exogenous FGFR3 and an exogenous SV2. In aspects of this embodiment, a cell capable of BoNT/A intoxication can be a cell stably expressing an exogenous mammalian FGFR3, such as, e.g., a human FGFR3, a bovine FGFR3, a rat FGFR3 or a mouse FGFR3. In other aspects of this embodiment, a cell capable of BoNT/A intoxication can be a cell stably expressing an exogenous bird FGFR3, such as, e.g., chicken FGFR3. In other aspects of this embodiment, a cell capable of BoNT/A intoxication can be a cell stably expressing an exogenous amphibian FGFR3, such as, e.g., a newt FGFR3 or a frog FGFR3. In other aspects of this embodiment, a cell capable of BoNT/A intoxication can be a cell stably expressing an exogenous fish FGFR3, such as, e.g., a zebrafish FGFR3. In other aspects of this embodiment, a cell capable of BoNT/A intoxication can be a cell stably expressing an exogenous SV2, such as, e.g., a SV2A, a SV2B, or a SV2C.

Aspects of the present invention provide, in part, detecting the presence of BoNT/A activity of said contacted cell relative to a control cell, where a difference in said BoNT/A activity of said contacted cell as compared to said control cell is indicative of BoNT/A activity. As used herein, the term "control cell" means a cell of the same or similar type as the contacted cell and grown under the same conditions but which is not contacted with any sample or is contacted with a defined negative sample or a defined positive sample. One skilled in the art understands that a variety of control cells are useful in the methods disclosed in the present specification and that a control cell can be a positive control cell or a negative control cell. A control cell can be, for example, a negative control cell such as a similar or identical cell containing the same or similar FGFR3 and/or a SV2 that is contacted with a similar, defined negative sample, which is known to lack active BoNT/A, or that is not contacted with any sample. A control cell also can be, for example, a positive control cell such as a similar or identical cell containing the same or similar FGFR3 and/or a SV2 contacted with a defined positive sample, which is known to include active BoNT/A.

A wide variety of assays can be used to determine the presence of BoNT/A activity, including direct and indirect assays for toxin uptake. Assays that determine BoNT/A binding or uptake properties can be used to assess BoNT/A activity. Such assays include, without limitation, cross-linking assays using labeled BoNT/A, such as, e.g., BoNT/A-SBED, see, e.g., Example II of the present specification and [$^{125}$I] BoNT/A, see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type Cl, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004). Antibodies useful for these assays include, without limitation, antibodies selected against a BoNT/A, antibodies selected against a BoNT/A receptor, such as, e.g., FGFR3 or a SV2, antibodies selected against a ganglioside, such as, e.g., GD1a, GD1b, GD3, GQ1b, or GT1b and selected against a test compound, such as, e.g., a molecule that selectively binds a BoNT/A receptor wherein selective binding modulates BoNT/A activity. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in detecting BoNT/A activity.

Assays that monitor the release of a molecule after exposure to BoNT/A can also be used to assess for the presence of BoNT/A activity. In these assays, inhibition of the molecule's release would occur in cells expressing a FGFR3 and/or a SV2 after BoNT/A treatment. As a non-limiting example the inhibition of insulin release assay disclosed in the present specification can monitor the release of a molecule after exposure to BoNT/A and thereby be useful in assessing whether a molecule selectively binds a BoNT/A receptor (see Example I). Other non-limiting assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and *botulinum* toxin type F, 90(3) Neuroscience 893-902 (1999); and Sara Stigliani et al., The sensitivity of catecholamine release to *botulinum* toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by *botulinum* toxin A or B, 236(3) Eur. J. Biochem. 877-886 (1996); and Patrick Foran et al., *Botulinum* neurotoxin C1 cleaves both syntaxin and SNAP-25 in intact and permeabilized chromaffin cells: correlation with its blockade of catecholamine release, 35(8) Biochemistry 2630-2636 (1996); and methods that measure inhibition of hormone release from endocrine cells, such as, e.g., anterior pituitary cells or ovarian cells. It is understood that these and similar assays for molecule release can be useful in assessing BoNT/A activity.

As non-limiting examples, an inhibition of insulin release assay can be used to determine the presence of BoNT/A activity in cells containing a FGFR3 and/or a SV2 and capable of secreting insulin; an inhibition of noradrenaline release assay can be used to determine BoNT/A activity in cells containing a FGFR3 and/or a SV2 and capable of secreting noradrenaline; and an inhibition of estrogen release assay can be used to determine BoNT/A activity in cells containing a FGFR3 and/or a SV2 and capable of secreting estrogen.

Assays that detect the cleavage of a BoNT/A substrate after exposure to BoNT/A can also be used to assess for the presence of BoNT/A activity. In these assays, generation of a BoNT/A cleavage-product would be detected after BoNT/A treatment. As a non-limiting example the SNAP-25 cleavage assay disclosed in the present specification can detect the cleavage of a BoNT/A substrate after exposure to BoNT/A and thereby be useful in assessing BoNT/A activity (see Example I). Other non-limiting limiting methods useful to detect the cleavage of a BoNT/A substrate after exposure to BoNT/A are described in, e.g., Lance E. Steward et al., FRET Protease Assays for *Botulinum* Serotype A/E Toxins, U.S. Patent Publication No. 2003/0143650 (Jul. 31, 2003); and Ester Fernandez-Salas et al., Cell-based Fluorescence Resonance Energy Transfer (FRET) Assays for Clostridial Toxins, U.S. Patent Publication 2004/0072270 (Apr. 15, 2004). It is understood that these and similar assays for BoNT/A substrate cleavage can be useful in assessing BoNT/A activity.

As non-limiting examples, Western blot analysis using an antibody that recognizes BoNT/A SNAP-25-cleaved product can be used to determine the presence of BoNT/A activity. Examples of anti-SNAP-25 antibodies useful for these assays include, without limitation, rabbit polyclonal anti-SNAP25$_{197}$ antiserum pAb anti-SNAP-25$_{197}$ #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

The methods disclosed in the present specification include, in part, a sample. As used herein, the term "sample" means any biological matter that contains or potentially contains an active BoNT/A. A variety of samples can be assayed according to a method disclosed in the present specification including, without limitation, purified, partially purified, or unpurified BoNT/A; recombinant single chain or di-chain toxin with a naturally or non-naturally occurring sequence; recombinant BoNT/A with a modified protease specificity; recombinant BoNT/A with an altered cell specificity; chimeric toxin containing structural elements from multiple BoNT/A species or subtypes; bulk BoNT/A; formulated BoNT/A product; and foods; cells or crude, fractionated or partially purified cell lysates, for example, engineered to include a recombinant nucleic acid encoding a BoNT/A; bacterial, baculoviral and yeast lysates; raw, cooked, partially cooked or processed foods; beverages; animal feed; soil samples; water samples; pond sediments; lotions; cosmetics; and clinical formulations. It is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, tissue samples obtained from a wound. Other such samples include mammalian tissue, mammalian saliva, mammalian excretions and mammalian feces. As non-limiting examples, a method of the invention can be useful for detecting the presence or activity of a BoNT/A in a food or beverage sample; to assay a sample from a human or animal, for example, exposed to a BoNT/A or having one or more symptoms of a BoNT/A exposure; to follow activity during production and purification of BoNT/A; or to assay formulated BoNT/A products such as pharmaceuticals or cosmetics.

It is envisioned that a wide variety of processing formats can be used in conjunction with the methods disclosed present specification, including, without limitation, manual processing, partial automated-processing, semi-automated-processing, full automated-processing, high throughput processing, high content processing, and the like or any combination thereof.

Other aspect of the present invention provide methods of reducing BoNT/A activity in a human comprising administering to said human a pharmaceutical composition comprising a molecule that selectively binds a FGFR3 wherein said selective binding reduces the ability of BoNT/A to bind to said FGFR3. In is envisioned that any molecule that can selectively bind to a FGFR3 in a manner that prevents BoNT/A binding to that same FGFR3 can be useful, including, without limitation, an anti-FGFR3 antibody, an FGF or an FGF agonist. In addition, a FGFR3, a FGFR3 fragment retaining BoNT/A selective binding activity, or peptidomimetic thereof can also be useful. Molecules that selectively bind a FGFR3, and thus useful in methods of reducing BoNT/A activity are described in, e.g., Avner Yayon et al., Antibodies that block receptor protein tyrosone kinase activation, methods of screening for and using thereof, International Publication No. WO 02/102972 (Dec. 27, 2002); Avner Yayon et al., Antibodies that block receptor protein tyrosone kinase activation, methods of screening for and using thereof, International Publication No. WO 02/102973 (Dec. 27, 2002); and Elisabeth Thomassen-Wolf et al., Antibodies that block receptor protein tyrosone kinase activation, methods of screening for and using thereof, International Publication No. WO 02/102854 (Dec. 27, 2002).

Other aspect of the present invention provide methods of reducing BoNT/A activity in a human comprising administering to said human a pharmaceutical composition comprising a molecule that selectively binds a SV2 wherein said selective binding reduces the ability of BoNT/A to bind to said SV2. In is envisioned that any molecule that can selectively bind to a SV2 in a manner that prevents BoNT/A binding to that same SV2 can be useful, including, without limitation, an anti-SV2 antibody or a SV2 agonist. In addition, a SV2, a SV2 fragment retaining BoNT/A selective binding activity or FGFR3 selective binding activity, or peptidomimetic thereof can also be useful.

Aspects of the present invention provide, in part, a method of reducing BoNT/A activity in a human by administering a pharmaceutical composition comprising a molecule that selectively binds a FGFR3 and/or a SV2. The administered composition can be formulated in a variety of pharmaceutically acceptable media, as described below. An effective dose of a composition disclosed in the present specification will depend upon the particular molecule selected, the route administration, and the particular characteristics of the human or other mammal, such as age, weight, general health and the like. An effective dose can be determined in an animal model prior to administration to humans. Compositions useful in aspects of the invention can be administered by a variety of routes to stimulate an immune response. As a non-limiting example, oral tolerance is well-recognized in the art (see, for example, Weiner, *Hospital Practice*, pp. 53-58 (Sep. 15, 1995). Those skilled in the art can readily determine for a particular composition, a suitable pharmacological composition, an appropriate antigen payload; route of administration; volume of dose; and pharmaceutical regimen useful in a particular animal, for example, humans.

As disclosed herein a pharmaceutical composition is administered to a human or other mammal to reduce BoNT/A activity. As used herein, the term "reduce," when used in reference to administering to a human or other mammal an effective amount of a pharmaceutical composition, means reducing a symptom of a condition characterized by exposure BoNT/A activity, or delaying or preventing onset of a symptom of a condition characterized by exposure to BoNT/A activity in the human or other mammal. For example, the term "reducing" can mean reducing a symptom of a condition characterized by exposure to BoNT/A activity by at least 30%, 40%, 60%, 70%, 80%, 90% or 100%. The effectiveness of a pharmaceutical composition in treating a condition characterized by exposure to BoNT/A activity can be determined by observing one or more clinical symptoms or physiological indicators associated with the condition. An improvement in a condition characterized by exposure to BoNT/A activity also can be indicated by a reduced need for a concurrent therapy. Those of skill in the art will know the appropriate symptoms or indicators associated with specific conditions and will know how to determine if a human or other mammal is a candidate for treatment with a pharmaceutical composition disclosed in the present specification. In particular, it is understood that those skilled in the art will be able to determine if a condition if characterized by exposure BoNT/A activity, for example, by comparison of levels of BoNT/A activity from the human or other mammal with a normal control cells.

The appropriate effective amount to be administered for a particular application of the methods can be determined by those skilled in the art, using the guidance provided herein. For example, an effective amount can be extrapolated from assays as described herein above. One skilled in the art will recognize that the condition of the patient can be monitored throughout the course of therapy and that the effective amount of a composition that is administered can be adjusted accordingly.

A pharmaceutical composition useful in aspects of the invention generally is administered in a pharmaceutical acceptable composition. As used herein, the term "pharmaceutically acceptable" refer to any molecular entity or composition that does not produce an adverse, allergic or other untoward or unwanted reaction when administered to a human or other mammal. As used herein, the term "pharmaceutically acceptable composition" refers to a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20 ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

A pharmaceutical composition useful in a method of the disclosure is administered to a human or other mammal in an effective amount. Such an effective amount generally is the minimum dose necessary to achieve the desired therapeutic effect, which can be, for example, that amount roughly necessary to reduce the symptoms associated with exposure to BoNT/A activity. For example, the term "effective amount" when used with respect to treating exposure to BoNT/A activity can be a dose sufficient to the symptoms, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the BoNT/A exposure, the age and weight of the patient, the patient's general physical condition, the cause of the BoNT/A exposure and the route of administration. Where repeated administration is used, the frequency of administration depends, in part, on the half-life of the pharmaceutical composition. Suppositories and extended release formulations can be useful in the invention and include, for example, dermal patches, formulations for deposit on or under the skin and formulations for intramuscular injection. It is understood that slow-release formulations also can be useful in the methods of the invention. The subject receiving the pharmaceutical composition can be any mammal or other vertebrate capable of experiencing exposure to BoNT/A activity, for example, a human, primate, horse, cow, dog, cat or bird.

Various routes of administration can be useful for reducing BoNT/A activity according to a method of the invention. A pharmaceutical composition useful in the methods of the invention can be administered to a mammal by any of a variety of means depending, for example, on the type and location of BoNT/A exposure to be treated, the pharmaceutical composition, or other compound to be included in the composition, and the history, risk factors and symptoms of the subject. Routes of administration suitable for the methods of the invention include both systemic and local administration. As non-limiting examples, a pharmaceutical composition useful for reducing BoNT/A activity can be administered orally or by subcutaneous pump; by dermal patch; by intravenous, subcutaneous or intramuscular injection; by topical drops, creams, gels or ointments; as an implanted or injected extended release formulation; as a bioerodible or non-bioerodible delivery system; by subcutaneous minipump or other implanted device; by intrathecal pump or injection; or by epidural injection. An exemplary list of biodegradable polymers and methods of use are described in, e.g., HANDBOOK OF BIODEGRADABLE POLYMERS (Abraham J. Domb et al., eds., Overseas Publishers Association, 1997); CONTROLLED DRUG DELIVERY: DESIGNING TECHNOLOGIES FOR THE FUTURE (Kinam Park & Randy J. Mrsny eds., American Chemical Association, 2000); Vernon G. Wong, *Method for Reducing or Preventing Transplant Rejection in the Eye and Intraocular Implants for Use Therefor*, U.S. Pat. No. 6,699,493 (Mar. 2, 2004); Vernon G. Wong & Mae W. L. Hu, *Methods for Treating Inflammation-mediated Conditions of the Eye*, U.S. Pat. No. 6,726,918 (Apr. 27, 2004); David A. Weber et al., *Methods and Apparatus for Delivery of Ocular Implants*, U.S. Patent Publication No. US2004/0054374 (Mar. 18, 2004); Thierry Nivaggioli et al., *Biodegradable Ocular Implant*, U.S. Patent Publication No. US2004/0137059 (Jul. 15, 2004). It is understood that the frequency and duration of dosing will be dependent, in part, on the relief desired and the half-life of the tolerogizing composition.

In particular embodiments, a method of the invention is practiced by peripheral administration of a pharmaceutical composition. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally."

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

Other aspect of the present invention provide methods of screening for a molecule able to compete with BoNT/A for selective binding to cells susceptible to BoNT/A intoxication by contacting said sample with a composition comprising an FGFR3 and detecting whether said molecule selectively binds said FGFR3, wherein selective binding of said molecule to said FGFR3 indicates that said molecule is able to compete with BoNT/A for selective binding to cells susceptible to BoNT/A intoxication, and wherein if said molecule is BoNT/A, said method does not comprise an $LD_{50}$ assay. Other aspect of the present invention provide methods of screening for a molecule able to compete with BoNT/A for selective binding to cells susceptible to BoNT/A intoxication by contacting said sample with a composition comprising a FGFR3, a SV2, or a FGFR3 and a SV2 and detecting whether said molecule selectively binds to a FGFR3 and/or a SV2, wherein selective binding of said molecule to a FGFR3 and/or a SV2 indicates that said molecule is able to compete with BoNT/A for selective binding to cells susceptible to BoNT/A intoxication, and wherein if said molecule is BoNT/A, said method does not comprise an $LD_{50}$ assay. As used herein, the term "selective" binding means that a binding agent is able to bind its target under physiological conditions, or in vitro conditions substantially approximating physiological conditions, to a statistically significantly greater degree (i.e., has a smaller $K_d$ or dissociation constant) than to other, non-target molecules on the surface of the neural cell. "$K_d$" is the molar concentration of the binding agent at which half the target molecules are bound by the binding agent. As used herein, the term "$LD_{50}$ assay" means an live animal-based in vivo assay of neurotoxin activity comprising detecting the dose of neurotoxin at which 50% of treated animals die, see, e.g., the Mouse Protection Assay (MPA), Charles L. Hatheway & Carol Dang, *Immunogenicity of the Neurotoxins of Clostridium botulinum*, 93-107 (Neurological Disease and Therapy-THERAPY WITH BOTULINUM TOXIN, Joseph Jankovic & Mark Hallett eds., Marcel Dekker, 1994).

It is envisioned that any and all assay conditions suitable for screening for a molecule able to compete with BoNT/A for selective binding to cells susceptible to BoNT/A intoxication can be useful, including, e.g., in vitro and in vivo assays. In addition, it is also foreseen that a wide variety of processing formats can be used in conjunction with the methods disclosed present specification, including, without limitation, manual processing, partial automated-processing, semi-automated-processing, full automated-processing, high throughput processing, high content processing, and the like or any combination thereof.

As disclosed above, any of the methods useful for detecting BoNT/A activity disclosed in the present specification and any of the compositions useful for practicing the methods useful for detecting BoNT/A activity disclosed in the present specification can be can be useful in screening for a molecule that competes with BoNT/A for the selectively binding to a FGFR3 and/or a SV2. Thus, in aspect of this embodiment, a FGFR3 can be encoded by the nucleic acid molecule from a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In another aspect of this embodiment, a FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g., a zebrafish FGFR3. In another aspect of this embodiment, a FGFR3 useful in screening for a molecule that competes with BoNT/A for the selectively binding to the FGFR3 can be transiently or stably contained in a cell. In another aspect of this embodiment, a composition useful in screening for a molecule that competes with BoNT/A for the selectively binding to a FGFR3 comprises a FGFR3 and optionally a SV2, such as, e.g., a SV2A, a SV2B, or a SV2C. In another aspect of this embodiment, a composition useful in screening for a molecule that competes with BoNT/A for the selectively binding to a FGFR3 comprises a FGFR3 and optionally a G1b polysialoganglioside, such as, e.g., GD1a, GD1b, GD3, GQ1b, or GT1b.

In another aspect of this embodiment, a cell can include cells, such as, e.g., neuronal cells including, without limitation, primary neuronal cells; immortalized or established neuronal cells; transformed neuronal cells; neuronal tumor cells; stably and transiently transfected neuronal cells expressing a FGFR3, SV2, or both a FGFR3 and a SV2, and further include, yet are not limited to, mammalian, murine, rat, primate and human neuronal cells. Other aspects of this embodiment include cells from, such as, e.g., neuronal cell lines including, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines. Non-limiting examples of neuronal cell lines include, e.g., neuroblastoma cell lines BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH; neuroblastoma/glioma hybrid cell lines N18, NG108-15 and NG115-401L; neuroblastoma/motor neuron hybrid cell lines NSC-19 and NSC-32; neuroblastoma/root ganglion neuron hybrid cell lines F11, ND-E, ND-U1, ND7/23, ND8/34 and ND27; the neuroblastoma/hippocampal neuron hybrid cell line HN-33; spinal cord cell lines TE 189.T and M4b; cerebral cortex cell lines CNh, HCN-1a and HCN-2; dorsal root ganglia cell line G4b; hippocampal cell lines HT-4, HT-22 and HN33; FGFR3 expressing cell lines H929, JIM-3, KMS-11, KMS-18, LB278, LB375, LB1017, LB2100, LP-1, OPM-2, PCL1 and UTMC-2. In further aspects of this embodiment, an FGFR3 expressing cell can be, e.g., H929, JIM-3, KMS-11, KMS-18, LB278, LB375, LB1017, LB2100, LP-1, OPM-2, PCL1 UTMC-2, B9, TC, L6 and CFK2. Other aspects of this embodiment include cells, such as, e.g., non-neuronal cells including, without limitation, primary non-neuronal cells; immortalized or established non-neuronal cells; transformed non-neuronal cells; non-neuronal tumor cells; stably and transiently transfected non-neuronal cells expressing a FGFR3, and further include, yet are not limited to, mammalian, murine, rat, primate and human non-neuronal cells. Other aspects of this embodiment include cells, such as, e.g., non-neuronal cells useful in aspects of the invention further include, without limitation, anterior pituitary cells; adrenal cells, pancreatic cells, ovarian cells, kidney cells, stomach cell, blood cells, epithelial cells, fibroblasts, thyroid cells, chondrocytes, muscle cells, hepatocytes, glandular cells and cells involved in glucose transporter (GLUT4) translocation.

The molecule to be tested in the screening method may be a "small" organic compound of synthetic origin, or may be a macromolecule (either of synthetic or biological origin) including without limitation, a polypeptide, such as, e.g., a growth factor, a neurotoxin, a modified neurotoxin, an antibody or an antibody derivative; a nucleic acid, such as, e.g., a nucleic acid aptomer; and a polysaccharide, such as, e.g., a ganglioside or a lectin. In one embodiment, the molecule is a synthetic molecule designed based on the tertiary structure and three dimensional conformation of FGF or an antibody that inhibits BoNT/A binding to a FGFR3. Such SAR (structure/activity relationship) analysis is routine in the art of medicinal chemistry, among other fields.

A wide variety of assays can be used to determine whether a molecule selectively binds a FGFR3, a SV2, or both a FGFR3 and a SV2, including direct and indirect assays for toxin uptake. Assays that determine BoNT/A binding or uptake properties can be used to assess whether a molecule selectively binds a FGFR3, a SV2, or both a FGFR3 and a SV2. Such assays include, without limitation, cross-linking assays using labeled BoNT/A, such as, e.g., BoNT/A-SBED, see, e.g., Example II of the present specification and [$^{125}$I] BoNT/A, see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type Cl, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004). Antibodies useful for these assays include, without limitation, antibodies selected against a BoNT/A, antibodies selected against a BoNT/A receptor, such as, e.g., FGFR3 or a SV2, antibodies selected against a ganglioside, such as, e.g., GD1a, GD1b, GD3, GQ1b, or GT1b and selected against a test compound, such as, e.g., a molecule that selectively binds a BoNT/A receptor wherein selective binding modulates BoNT/A activity. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in selecting a neuron or other cells useful in aspects of the invention.

Assays that monitor the release of a molecule after exposure to BoNT/A can also be used to assess whether a molecule selectively binds a FGFR3, a SV2, or both a FGFR3 and a SV2. In these assays, inhibition of the molecule's release would occur in cells expressing a FGFR3 after BoNT/A treatment. As a non-limiting example the inhibition of insulin release assay disclosed in the present specification can monitor the release of a molecule after exposure to BoNT/A and thereby be useful in assessing whether a molecule selectively binds a FGFR3 (see Example I). Other non-limiting assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and *botulinum* toxin type F, 90(3) Neuroscience 893-902 (1999); and Sara Stigliani et al., The sensitivity of catecholamine release to *botulinum* toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by *botulinum* toxin A or B, 236(3) Eur. J. Biochem. 877-886 (1996); and Patrick Foran et al., *Botulinum* neurotoxin C1 cleaves both syntaxin and SNAP-25 in intact and permeabilized chromaffin cells: correlation with its blockade of catecholamine release, 35(8) Biochemistry 2630-2636 (1996); and methods that measure inhibition of hormone release from endocrine cells, such as, e.g., anterior pituitary cells or ovarian cells. It is understood that these and similar assays for molecule release can be useful in assessing whether a molecule selectively binds a FGFR3, a SV2, or both a FGFR3 and a SV2.

As non-limiting examples, an inhibition of insulin release assay can be used to test whether a molecule selectively binds a FGFR3, a SV2, or a FGFR3 and a SV2 in FGFR3 and/or SV2 containing cells capable of secreting insulin; an inhibition of noradrenaline release assay using can be used to test whether a molecule selectively binds FGFR3, a SV2, or a FGFR3 and a SV2 in FGFR3 and/or SV2 containing cells capable of secreting noradrenaline; and an inhibition of estrogen release assay can be used to assay whether a molecule selectively binds a FGFR3, a SV2, or a FGFR3 and a SV2 in FGFR3 and/or SV2 containing cells and capable of secreting estrogen.

Assays that detect the cleavage of a BoNT/A substrate after exposure to BoNT/A can also be used to assess whether a molecule selectively binds a FGFR3, a SV2, or both a FGFR3 and a SV2. In these assays, generation of a BoNT/A cleavage-product would be detected in cells expressing a FGFR3, a SV2, or both a FGFR3 and a SV2 after BoNT/A treatment. As a non-limiting example the SNAP-25 cleavage assay disclosed in the present specification can detect the cleavage of a BoNT/A substrate after exposure to BoNT/A and thereby be useful in assessing whether a molecule selectively binds a BoNT/A receptor (see Example I). Other non-limiting methods useful to detect the cleavage of a BoNT/A substrate after exposure to BoNT/A are described in, e.g., Lance E. Steward et al., FRET Protease Assays for *Botulinum* Serotype A/E Toxins, U.S. Patent Publication No. 2003/0143650 (Jul. 31, 2003); and Ester Fernandez-Salas et al., Cell-based Fluorescence Resonance Energy Transfer (FRET) Assays for Clostridial Toxins, U.S. Patent Publication 2004/0072270 (Apr. 15, 2004). It is understood that these and similar assays for BoNT/A substrate cleavage can be useful in assessing whether a molecule selectively binds a FGFR3, a SV2, or both a FGFR3 and a SV2.

As non-limiting examples, Western blot analysis using an antibody that recognizes BoNT/A SNAP-25-cleaved product can be used to assay whether a molecule selectively binds a FGFR3, a SV2, or both a FGFR3 and a SV2. Examples of anti-SNAP-25 antibodies useful for these assays include, without limitation, rabbit polyclonal anti-SNAP25$_{197}$ antiserum pAb anti-SNAP-25$_{197}$ #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

Assays that detect competitive binding of a molecule with BoNT/A for selective binding to a FGFR3, a SV2, or both a FGFR3 and a SV2 can also be used to assess whether a molecule selectively binds a FGFR3, a SV2, or both a FGFR3 and a SV2. In these assays, a reduction in BoNT/A activity would be detected as the amount of a molecule that competes with BoNT/A for selective binding to a BoNT/A would increase. In a non-limiting example, the competitive inhibition assay using FGF ligands disclosed in the present specification can be used to detect the competitive binding of a molecule with BoNT/A for selective binding to a FGFR3 and thereby be useful in assessing whether a molecule selectively binds a BoNT/A receptor (see Example II). Thus in one aspect of this embodiment, competitive binding assays using a FGFR3-binding molecule with BoNT/A for selective binding to a FGFR3 can be used to assess whether a molecule selectively binds a FGFR3.

Other aspect of the present invention provide methods of rendering a cell susceptible to cleavage of SNARE proteins by BoNT/A, comprising inducing said cell to express a FGFR3, a SV2, or both a FGFR3 and a SV2. Other aspect of the present invention provide methods of transiently rendering a cell susceptible to cleavage of SNARE proteins by BoNT/A, comprising transiently inducing said cell to express a FGFR3. Other aspect of the present invention provide methods of stably rendering a cell susceptible to cleavage of SNARE proteins by BoNT/A, comprising stably inducing said cell to express a FGFR3, a SV2, or both a FGFR3 and a SV2.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin with a composition comprising a FGFR3 and detecting whether said neurotoxin selectively binds said FGFR3, wherein selective binding of said neurotoxin to said FGFR3 indicates that said neurotoxin is able to selective binding to cells susceptible to BoNT/A intoxication and wherein if said molecule is BoNT/A, said method does not comprise an $LD_{50}$ assay; packaging said neurotoxin for sale in a manner consistent with the requirements of said regulatory authority, and selling said neurotoxin.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity; packaging said neurotoxin for sale in a manner consistent with the requirements of said regulatory authority, and selling said neurotoxin.

In another embodiment, the invention is drawn to a polypeptide comprising at least the $H_C$ region of BoNT/A, which is produced from a bulk or formulated preparation wherein the bulk or formulated preparation is assayed for specific binding to neural cells using a method comprising contacting said polypeptide with a composition comprising FGFR3 receptor and, optionally, GT1b ganglioside, and detecting whether said polypeptide selectively binds FGFR3.

In another embodiment similar to the above aspect of the invention, the polypeptide comprises at least an FGFR3 binding domain, other than the $H_C$ domain of BoNT/A. Such a binding domain may comprise, for example, an FGF, such as FGF 1, FGF2, FGF4, FGF8 or FGF 9, or an anti-FGFR3 antibody. Further, the polypeptide may optionally contain a translocation domain such as the $H_N$ domain of BoNT/A. Additionally, the polypeptide will generally contain a clostridial neurotoxin light chain or variation thereof—the nature and/or source of the light chain can provide differences in the extent and half-life of the therapeutic effect of the polypeptide.

Thus, in this embodiment the claimed polypeptide is produced (which production may include purification, enzymatic treatment, and/or oxidation steps) from a bulk or formulation preparation. In one embodiment the preparation may be, for example, a cell lysate from fermentation of a BoNT/A-producing strain of Clostridium botulinum, or from a suitable mammalian, insect or bacterial host cell producing a recombinant version of BoNT/A. Such a bulk preparation may also be produced using cell-free transcription methodologies. In another embodiment the preparation may be purified BoNT/A formulated with associated stabilizing proteins, such as serum albumin. In each case, the preparation may comprise BoNT/A molecules which are denatured or otherwise incorrectly folded so as not to bind to the target cells. The potency and/or specific activity of the preparation, or of fractions purified from the preparation, can be detected by using the claimed assay method.

Alternatively, the polypeptide to be assayed may comprise only a portion of the entire BoNT/A molecule. For example, the bulk preparation may contain only the heavy chain of BoNT/A, as separate production of the heavy and light chains of the toxin may be a preferred way of avoiding accidental exposure to the neurotoxin by laboratory workers.

As another example of the above embodiment, the polypeptide may comprise a chimeric recombinant polypeptide which contains the Hc region of the heavy chain of BoNT/A (or some other FGFR3-binding moiety, such as FGF itself). The chimeric polypeptide comprises amino acid sequence regions additional to, or other than, those present in the wild-type BoNT/A BoNT/A molecule. For example, botulinum and tetanus toxins may be used as the basis for the creation of transport proteins, see, e.g., James Oliver Dolly et al., Modification of clostridial toxins for use as transport proteins, U.S. Pat. No. 6,203,794 (Mar. 20, 2001). The light chain of these transport proteins are generally either replaced by a therapeutic moiety or inactivated and coupled to such a therapeutic moiety. Additionally, chimeric neurotoxins can be made comprising polypeptides containing domains of more than one neurotoxin see, e.g., James Oliver Dolly et al., Activatable Recombinant Neurotoxins, International Publication No. WO 01/14570 (Mar. 1, 2001). Thus, this aspect of the invention also encompasses, as a embodiment, chimeric neurotoxins containing at least the $H_C$ domain of BoNT/A. Such molecules may be useful in modulating the time or extent of the inhibition of secretory vesicle release. Further, it may be desirable to target agents, such as therapeutic agents, to the extracellular surface of the neural cell membrane. Thus, such an agent may be joined (e.g., as a fusion protein or via post translational conjugation) to the $H_C$ portion of BoNT/A.

In such a case the cell lysate or conjugation reaction mixture may comprise a batch preparation in accordance with this aspect of the invention.

The above-referenced polypeptides are screened for binding and/or internalization essentially as mentioned above in the described screening method embodiment.

In yet another embodiment, the present invention is drawn to a method of marketing a polypeptide which contains a region capable of binding the FGFR3 receptor comprising obtaining permission from a governmental or regional drug regulatory authority to sell said polypeptide, wherein said polypeptide is first produced from a bulk preparation which is assayed for selective binding of said polypeptide to neural cells by contacting the bulk preparation containing said polypeptide with a composition comprising FGFR3 receptor, and optionally GT1b ganglioside, and detecting whether said polypeptide selectively binds FGFR3 under such conditions, packaging said polypeptide for sale in a manner consistent with the requirements of said regulatory authority, and offering said polypeptide for sale.

In this embodiment the invention is drawn to a method of marketing a polypeptide containing the $H_C$ region of a BoNT/A toxin. The polypeptide at issue in this embodiment of the invention is produced from a bulk preparation which is assayed for purity or activity using the screening method described previously. In a step of this method, permission is obtained from a regulatory body for the marketing of such polypeptide. In this context "permission" may be tacit or express; that is, permission or approval may be obtained from the regulatory authority for the sale of a therapeutic agent or composition comprising said polypeptide, in which case "permission" is marketing approval for the sale of such agent or composition. Alternatively, "permission", as used herein, may comprise the assent, either affirmatively given or manifested by its lack of objection, of such regulatory authority to the continued sale of a product containing a polypeptide assayed in this new manner. As before, the polypeptide may comprise BoNT/A, or a derivative thereof, or a fusion protein or conjugate containing the $H_C$ region of the BoNT/A heavy chain.

The therapeutic product comprising the polypeptide originally contained in the bulk preparation so assayed is labeled in accordance with the requirements of the regulatory authority. The product is then offered for sale. Offering for sale may comprise advertising or sales activity, educational seminars directed at doctors, hospitals, insurers, or patients, conversations with state, regional or governmental officials concerning subsidy reimbursement (such as Medicare or Medical).

Aspects of the present invention can also be described as follows:

1. A method of detecting BoNT/A activity by contacting a sample to a cell that contains an exogenous FGFR3 and an exogenous SV2 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.
2. The method according to 1, wherein said cell transiently contains an exogenous FGFR3.
3. The method according to 1, wherein said cell stably contains an exogenous FGFR3.
4. The method according to 1, wherein said FGFR3 is a mammalian FGFR3.
5. The method according to 4, wherein said mammalian FGFR3 is a human FGFR3.
6. The method according to 4, wherein said mammalian FGFR3 is a bovine FGFR3.
7. The method according to 4, wherein said mammalian FGFR3 is a mouse FGFR3.
8. The method according to 4, wherein said mammalian FGFR3 is a rat FGFR3.
9. The method according to 1, wherein said FGFR3 is a bird FGFR3.
10. The method according to 9, wherein said bird FGFR3 is a chicken FGFR3.
11. The method according to 1, wherein said FGFR3 is an amphibian FGFR3.
12. The method according to 11, wherein said amphibian FGFR3 is a frog FGFR3.
13. The method according to 11, wherein said amphibian FGFR3 is a newt FGFR3.
14. The method according to 1, wherein said FGFR3 is a fish FGFR3.
15. The method according to 15, wherein said fish FGFR3 is a zebrafish FGFR3.
16. The method according to 1, wherein said SV2 is SEQ ID NO: 33, SEQ ID NO: 34, SEQ ID NO: 35, or SEQ ID NO: 36.
17. The method according to 1, wherein said cell further contains a G1b polysialoganglioside.
18. The method according to 17, wherein said polysialoganglioside is selected from the group consisting of GD1a, GD1b, GD3, GQ1b, or GT1b.
19. The method according to 1, wherein said cell is a neuronal cell.
20. The method according to 19, wherein said neuronal cell is a primary neuronal cell.
21. The method according to 19, wherein said neuronal cell is an immortalized neuronal cell.
22. The method according to 19, wherein said neuronal cell is a transformed neuronal cell.
23. The method according to 19, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.
24. The method according to 1, wherein said cell is a non-neuronal cell.
25. The method according to 24, wherein said non-neuronal cell is a primary neuronal cell.
26. The method according to 24, wherein said non-neuronal cell is an immortalized neuronal cell.
27. The method according to 24, wherein said non-neuronal cell is a transformed neuronal cell.
28. The method according to 24, wherein said non-neuronal cell is selected from the group consisting of an anterior pituitary cell, an adrenal cell, a pancreatic cell, an ovarian cell, a kidney cell, a stomach cell, a blood cell, an epithelial cell, a fibroblast, a thyroid cell, a chondrocyte, a muscle cell, a hepatocyte, a glandular cell.
29. The method according to 1, wherein said sample is selected from the group consisting of a purified BoNT/A, a partially purified BoNT/A or unpurified BoNT/A.
30. The method according to 1, wherein said sample is selected from the group consisting of a bulk BoNT/A, a formulated BoNT/A, a cosmetics BoNT/A formulation or a clinical BoNT/A formulation.
31. The method according to 1, wherein said sample is a recombinant BoNT/A.
32. The method according to 1, wherein said sample is selected from the group consisting of a raw food, a cooked food, a partially cooked food or a processed food.

33. The method according to 1, wherein said sample is a sample taken from a mammal.

34. The method according to 33, wherein said mammalian sample is selected from the group consisting of a tissue, a saliva, an excretion or a feces.

35. A method of reducing BoNT/A activity in a human comprising administering to said human a pharmaceutical composition comprising a molecule that selectively binds a SV2 wherein said selective binding reduces the ability of BoNT/A to bind to said SV2.

36. A method according to 35, further comprising administering to said human a G1b polysialoganglioside.

37. The method according to 35, wherein said polysialoganglioside is selected from the group consisting of GD1a, GD1b, GD3, GQ1b, or GT1b.

38. A method of screening a for a molecule able to compete with BoNT/A for selective binding to cells susceptible to BoNT/A intoxication by contacting said sample with a composition comprising an FGFR3 and a SV2 and detecting whether said molecule selectively binds said FGFR3, wherein selective binding of said molecule to said FGFR3 indicates that said molecule is able to compete with BoNT/A for selective binding to cells susceptible to BoNT/A intoxication, and wherein if said molecule is BoNT/A, said method does not comprise an $LD_{50}$ assay.

39. The method according to 38, wherein said contacting step is performed in vitro.

40. The method according to 38, wherein said contacting step is performed in vivo.

41. The method according to 38, wherein said FGFR3 is expressed on the surface of a cell.

42. The method according to 40, wherein said cell transiently contains an exogenous FGFR3.

43. The method according to 40, wherein said cell stably contains an exogenous FGFR3.

44. The method according to 38, wherein said FGFR3 is a mammalian FGFR3.

45. The method according to 44, wherein said mammalian FGFR3 is a human FGFR3.

46. The method according to 44, wherein said mammalian FGFR3 is a bovine FGFR3.

47. The method according to 44, wherein said mammalian FGFR3 is a mouse FGFR3.

48. The method according to 44, wherein said mammalian FGFR3 is a rat FGFR3.

49. The method according to 38, wherein said FGFR3 is a bird FGFR3.

50. The method according to 49, wherein said bird FGFR3 is a chicken FGFR3.

51. The method according to 38, wherein said FGFR3 is an amphibian FGFR3.

52. The method according to 51, wherein said amphibian FGFR3 is a frog FGFR3.

53. The method according to 51, wherein said amphibian FGFR3 is a newt FGFR3.

54. The method according to 38, wherein said FGFR3 is a fish FGFR3.

55. The method according to 54, wherein said fish FGFR3 is a zebrafish FGFR3.

56. The method according to 38, wherein said SV2 is SEQ ID NO: 33, SEQ ID NO: 34, SEQ ID NO: 35, or SEQ ID NO: 36.

57. The method according to 38, wherein said composition further contains a G1b polysialoganglioside.

58. The method according to 57, wherein said polysialoganglioside is selected from the group consisting of GD1a, GD1b, GD3, GQ1b, or GT1b.

59. The method according to 38, wherein said cell is a neuronal cell.

60. The method according to 59, wherein said neuronal cell is a primary neuronal cell.

61. The method according to 59, wherein said neuronal cell is an immortalized neuronal cell.

62. The method according to 59, wherein said neuronal cell is a transformed neuronal cell.

63. The method according to 59, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

64. The method according to 38, wherein said cell is a non-neuronal cell.

65. The method according to 64, wherein said non-neuronal cell is a primary neuronal cell.

66. The method according to 64, wherein said non-neuronal cell is an immortalized neuronal cell.

67. The method according to 64, wherein said non-neuronal cell is a transformed neuronal cell.

68. The method according to 64, wherein said non-neuronal cell is selected from the group consisting of an anterior pituitary cell, an adrenal cell, a pancreatic cell, an ovarian cell, a kidney cell, a stomach cell, a blood cell, an epithelial cell, a fibroblast, a thyroid cell, a chondrocyte, a muscle cell, a hepatocyte, a glandular cell.

69. The method according to any one of claims 38-40, wherein said molecule is BoNT/A.

70. The method according to 69, wherein said molecule comprises a receptor binding domain of a BoNT/A heavy chain.

71. The method according to any one of claims 38-40, wherein said molecule is a molecule that selectively binds to the receptor binding domain of FGFR3 and is not BoNT/A 72. The method according to 71, wherein said molecule comprises an anti-FGFR3 antibody that binds to the receptor binding domain of FGFR3.

73. The method according to 71, wherein said molecule comprises a FGF that binds to the receptor binding domain of FGFR3.

74. The method according to 73, wherein said FGF molecule is selected from the group consisting of FGF1, FGF2, FGF4, FGF8 and FGF9.

75. The method according to any one of claims 38-40, wherein said molecule is a molecule that selectively binds to the receptor binding domain of FGFR3 and comprises a protease domain which cleaves a SNARE protein at a site other than that cleaved by BoNT/A light chain.

76. The method according to 75, wherein said protease domain comprises the active site of the light chain of a Clostridial toxin other than BoNT/A.

77. The method according to 76, wherein said protease domain comprises the active site of the light chain of BoNT/E.

78. A method of determining BoNT/A activity from a preparation comprising BoNT/A comprising the method of 38.

EXAMPLES

Example I

Figure 4A:
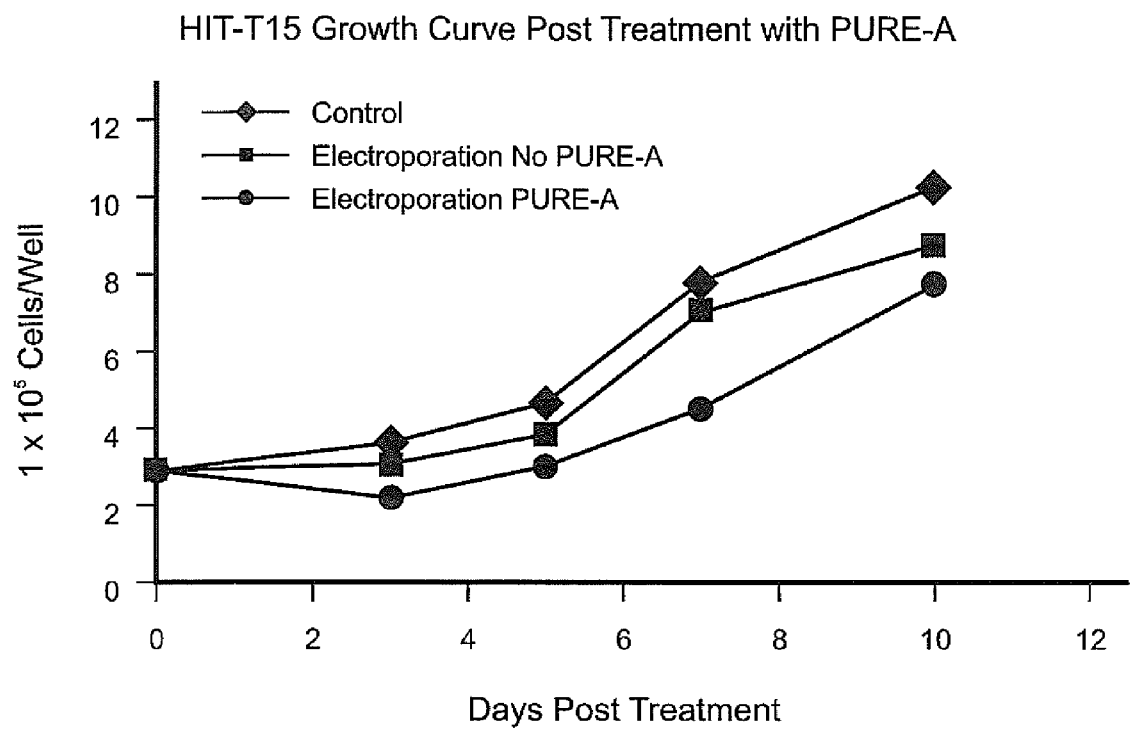
FIG. 4a shows the results on an inhibition release for insulin assay demonstrating that the presence of the toxin delayed growth in HIT-T15 cells when compared to controls, but toxin-treated cells were able to replicate normally after a recovery period.
Figure 4B:
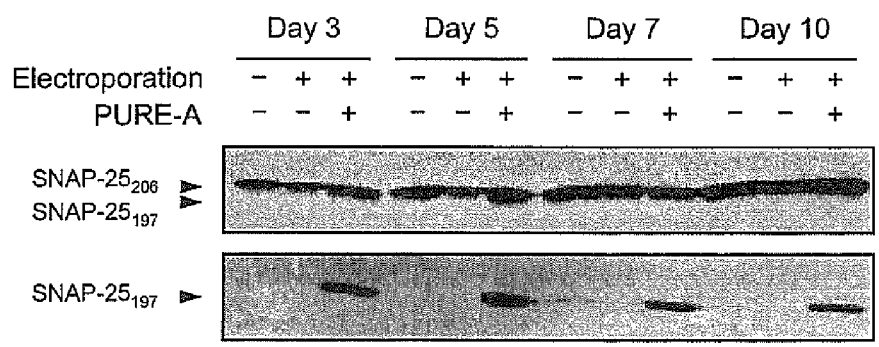
FIG. 4b shows a western blot analysis demonstrating that cleavage of SNAP-25 was detected at all time points tested when PURE-A was introduced into the cells, with equal amounts of protein loaded per lane and probed with an antibody that detects the BoNT/A SNAP-25$_{197}$ cleavage product.

Identification of a BoNT/A Receptor Using a Genetic Complementation Procedure 1. Identification of Cells Useful in Screening for a BoNT/A Receptor

1a. Identification of BoNT/A Receptor Lacking Cells Using an Inhibition Assay for Insulin Release To determine whether HIT-T15 cells express a receptor for BoNT/A, an inhibition assay for insulin release was performed. In response to glucose stimulation, the hamster insulinoma cell line HIT-T15 secretes insulin in a exocytic process that depends on the activity of SNAP-25 for vesicle docking and fusion. If HIT-T15 cells lack a BoNT/A receptor, these cells would be unable to uptake BoNT/A upon exposure to this toxin and insulin secretion could occur in the presence of high glucose in the media. However, if HIT-T15 cells contain a BoNT/A receptor, insulin secretion would be inhibited after BoNT/A treatment since the toxin could intoxicate the cell and cleave SNAP-25.

To conduct an inhibition assay for insulin release, a suitable seed density of approximately $1.5\times10^5$ cells/mL of HIT-T15 cells was plated into individual wells of 6-well, poly-D-lysine/Laminin coated, tissue culture plates containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach a density of about $5\times10^5$ cells/ml (6-16 hours). A group of HIT-T15 cells were treated with approximately 1 nM of PURE-A by introducing the toxin using electroporation using a GENE PULSER® II set at 960 pF and 0.28 kV (Bio-Rad Laboratories, Hercules, Calif.). An untreated control group underwent electroporation without PURE-A. The media from the wells containing treated and untreated electroporated cells was replaced with 3 mL of fresh complete DMEM supplement with either 5.6 mM glucose (low glucose) or 25 mM glucose (high glucose) and these cells were incubated in a 37° C. incubator under 5% carbon dioxide for approximately 1 hour to induce insulin secretion. The conditioned media was transferred to 15 mL tubes and the amount of insulin present in the condition media samples was determined using an Insulin ELISA assay (Peninsula Laboratories, Inc., San Carlos, Calif.). Exocytosis is expressed as the amount of insulin secreted per $1.5\times10^5$ cell/hr. Insulin release was detected in BoNT/A-untreated cells simulated by 25 mM glucose, but insulin secretion was inhibited in BoNT/A-treated cells (see FIG. 3*a*). These data indicate that the release of insulin in HIT-T15 cells is mediated, in part, by SNAP-25, but that these cells lack a BoNT/A receptor.

1b. Identification of BoNT/A Receptor Lacking Cells Using an Using a SNAP-25 Cleavage Assay To determine whether HIT-T15 cells express a receptor for BoNT/A, a SNAP-25 cleavage assay was performed. If HIT-T15 cells lack a BoNT/A receptor, then only the presence of the uncleaved SNAP-25 substrate would be detected after Western blot analysis. However, if HIT-T15 cells contain a BoNT/A receptor, then the toxin could intoxicate the cell and the presence of the cleaved BoNT/A SNAP-$25_{197}$ product would be detected.

To conduct a SNAP-25 cleavage assay, cells were grown in poly-D-lysine/Laminin coated 6-well plates and treated with PURE-A as described above in Example I, 1a. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl)piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,'N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/mL or higher concentration.

To detect for the presence of a cleaved BoNT/A substrate, samples were boiled for 5 min, and 40 µl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-200, polyoxyethylene (20) sorbitan monolaureate, 2% bovine serum albumin, 5% nonfat dry milk. Blocked membranes were incubated at 4° C. for overnight in Tris-Buffered Saline TWEEN-20° (25 mM Tris-Buffered Saline, 0.1% TWEEN-20®, polyoxyethylene (20) sorbitan monolaureate) containing a 1:5,000 dilution of rabbit polyclonal anti-SNAP25 antiserum pAb anti-SNAP25197 #1, a polyclonal antibody which is specific for the $SNAP25_{197}$-cleavage product and does not cross-react with full-length $SNAP25_{206}$, (Allergan, Inc., generated under contract with Zymed Laboratories Inc., South San Francisco, Calif.). Primary antibody probed blots were washed three times for 15 minutes each time in Tris-Buffered Saline TWEEN-200. Washed membranes were incubated at room temperature for 2 hours in Tris-Buffered Saline TWEEN-200 containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of the labeled BoNT/A $SNAP25_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A BoNT/A $SNAP25_{197}$-cleavage product was detected in HIT-T15 cell treated with BoNT/A but not untreated cells, indicating that HIT-T15 cells express SNAP-25 but not the BoNT/A receptor (see FIG. 3*b*).

1c. Assessment of BoNT/A Exposure on HIT-T15 Growth To evaluate if the presence of the toxin in the cells affect cell growth, HIT-T15 cells were electroporated as described above in Example I, 1a and monitored for 10 days. FIG. 4a demonstrates that the presence of the toxin delayed growth when compared to controls, but toxin-treated cells were able to replicate normally after a recovery period. Cell aliquots for days 3, 5, 7 and 10 were also tested for the presence of the BoNT/A SNAP-$25_{197}$ cleavage product using the SNAP-25 cleavage assay as described above in Example I, 1b. FIG. 4b shows that cleavage of SNAP-25 was detected by Western blot analysis at all time points assayed when PURE-A was introduced into the cells.

2. Identification of BoNT/A Receptor Using Genetic Complementation

To identify a BoNT/A receptor, a nucleic acid molecule encoding a BoNT/A receptor was cloned by genetic complementation. This procedure involves introducing a nucleic acid molecule encoding the BoNT/A receptor into a cell line that does not contain the receptor naturally by retroviral transduction, see, e.g., Mitchell H. Finer et al., Methods for Production of High Titer Virus and High Efficiency Retroviral Mediated Transduction of Mammalian Cells, U.S. Pat. No. 5,858,740 (Jul. 12, 1999).

2a. Production of a Retroviral Stock Containing pLIb Expression Constructs

To produce an retroviral stock containing expression constructs encoding human brain nucleic acid molecules, about $5 \times 10^5$ HEK 293-based cells (AmphoPack™ 293 cells; BD Biosciences Clontech, Palo Alto, Calif.) were plated in 60 mm tissue culture dishes containing 5 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach 60% to 80% confluency or a density of about 1 to $2 \times 10^6$ cells/ml (12-24 hours). On the day of transfection, the complete, supplemented DMEM media was replaced with 3 mL of OPTI-MEM Reduced Serum Medium. A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 pg of pLIB retroviral expression constructs containing nucleic acid molecules derived from human brain cells (BD Biosciences Clontech, Palo Alto, Calif.). This transfection is incubated at room temperature for approximately 20 minutes. The 500 µL transfection solution was then added to the AmphoPack™ 293 cells and the cells were incubated in a 37° C. incubator under 5% carbon dioxide for approximately 8-10 hours. The transfection media was replaced with 3 mL of fresh complete, supplemented DMEM and cells were incubated in a 37° C. incubator under 5% carbon dioxide for approximately 48-72 hours. The retrovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the retroviral particles is transferred to 2 mL cryovials in 1 mL aliquots and should contain approximately $5 \times 10^4$ to $5 \times 10^6$ tu/mL of retroviral particles. Aliquots can be stored at −80° C. until needed.

2b. Transduction of Cells with a Retroviral Stock Containing pLIB Expression Constructs To transduce cells with a retroviral stock containing expression constructs encoding human brain nucleic acid molecules, about $1.5 \times 10^5$ HIT-T15 cells were plated in 60 mm tissue culture dishes containing 5 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach 60% to 80% confluency or a density of about $5 \times 10^5$ cells/mL (6-16 hours). Cells are inoculated with the retroviral stock containing nucleic acid molecules derived from human brain cells (see Example I, 2a), using a suitable multiplicity of infection. Approximately 4-8 µg/mL of polybrene was then added and the cells were incubated for approximately 16-24 hours in a 37° C. incubator under 5% carbon dioxide. The transduction media is replaced with 5 mL of fresh complete, supplemented DMEM and the cells were incubated in a 37° C. incubator under 5% carbon dioxide for approximately four days. The transduced cells were then used to conduct a screening assay to identify a BoNT/A receptor. For greater details on procedures described in this example, see Retroviral Gene Transfer and Expression User Manual PT3132-1 (PR43789), BD Biosciences Clontech, Palo Alto, Calif., (Mar. 3, 2004).

2c. Screening of HIT-T15 Cells Expressing a Retroviral cDNA Library

Figure 5:
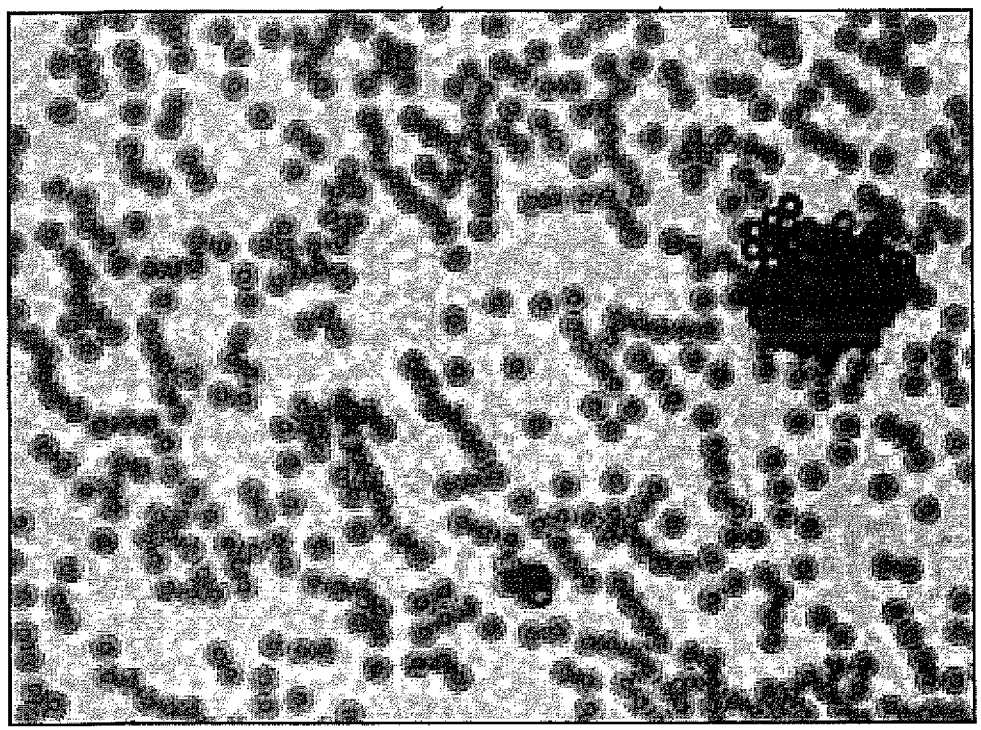
FIG. 5 shows HIT-T15 cells, transformed with a human brain cDNA library and selected using magnetic beads to which BONT/A had been bound. Individual colonies are visible in the dish and are surrounded by magnetic beads.

To screen for cells expressing a BoNT/A receptor, transduced HIT-T15 cells as described above in Example I, 2b were screened based on their ability to bind Dynex Beads coated with Pure A (ref). Approximately 7.5 mg of Dynabeads® magnetic beads (Dynal Biotechnology, LLC, Brown Deer, Wis.) coated with an antibody against the light chain of BONT/A was added to the media for 30 minutes at 4° C. and cells binding to the BoNT/A light chain were isolated as clumps of cells after exposure to a magnet. These isolated cells were washed once with PBS and transferred to new 60 mm tissue culture dishes containing 5 mL of complete DMEM. These cells were re-screened with 7.5 mg of Dynabeads® magnetic beads coated with PURE-A for 30 minutes at 4° C. and cells binding to PURE-A were isolated as clumps of cells after exposure to a magnet (see FIG. 5). These re-isolated cell colonies were transferred to 96-well plates containing 0.25 mL of complete DMEM and the cells were grown in a 37° C. incubator under 5% carbon dioxide until confluent.

Figure 6:
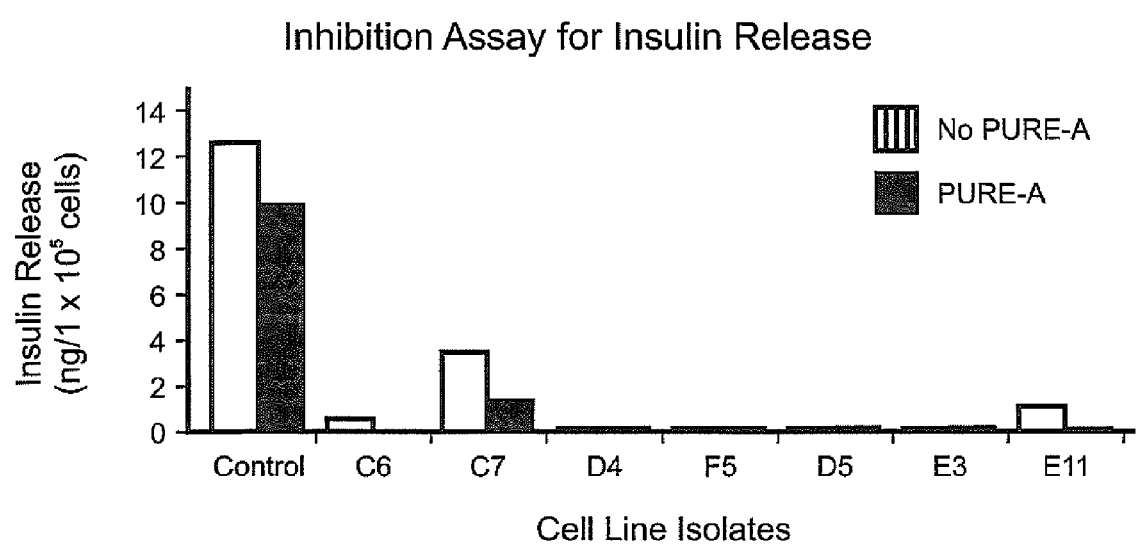
FIG. 6 shows the results of an assay of insulin release from HIT-T15 cells containing the putative BONT/A receptor. Cells were exposed to 1 nM PURE-A and assayed for inhibition of insulin release upon glucose stimulation.
Figure 7A:
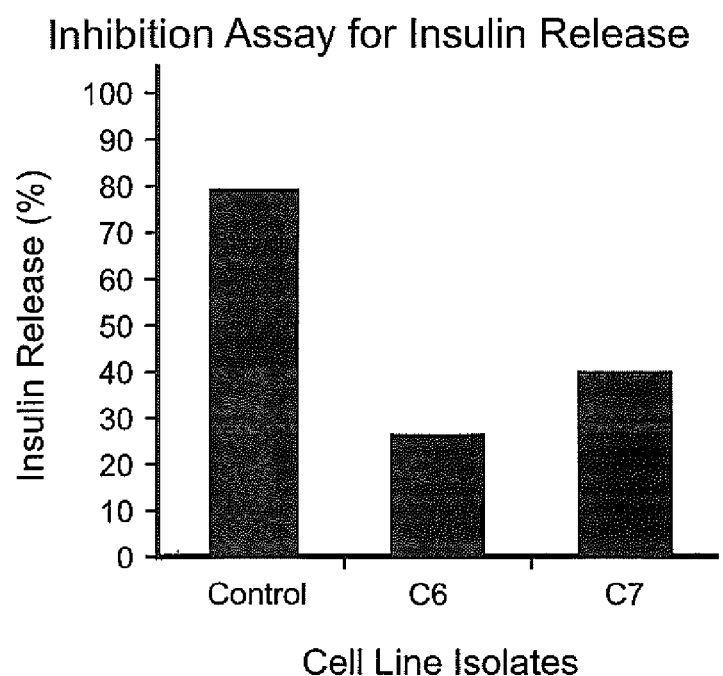
FIG. 7a shows the reduction of insulin release in representative HIT-T15 transformants C6 and C7 upon incubation with BONT/A.
Figure 7B:
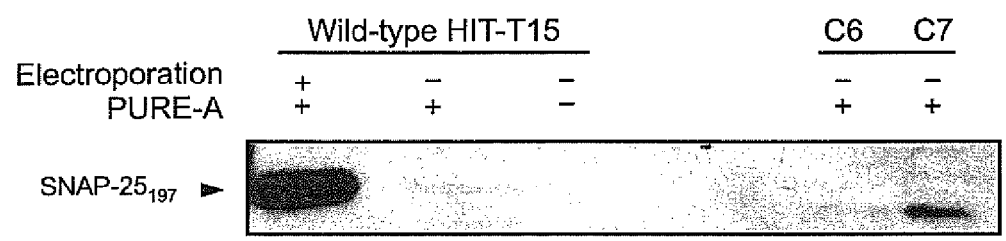
FIG. 7b shows a western blot analysis demonstrating that cleavage of SNAP-25 was detected in clones C6 and C7 incubated with BONT/A, with equal amounts of protein loaded per lane and probed with an antibody that detects the BoNT/A SNAP-25$_{197}$ cleavage product.

To test for the presence of a BoNT/A receptor, individual, cells contained in the 96-well plates were assayed using the inhibition assay for insulin release assay, as describes above in Example I, 1a. Cell lines containing a candidate BoNT/A receptor were selected based on the detection of the inhibition of insulin release. FIG. 6 show that transduced HIT-T15 cell lines C6 and C7 as candidate cell lines expressing a BoNT/A receptor. To confirm these results, expanded cultures of clones C6 and C7 as described above in Example I, 2-a and tested using the inhibition of insulin release assay and the SNAP-25 cleavage assay, as described above in Example I, 1b. The results indicate that a BoNT/A receptor is present in these cell lines based on the inhibition of insulin release (see FIG. 7a) and the presence of a BoNT/A SNAP$25_{197}$-cleavage product (see FIG. 7b).

2d. Cloning of BoNT/A Receptor

To isolate nucleic acid molecules encoding the BoNT/A receptor, DNA will be purified from the BoNT/A receptor-containing HIT-T15 cell isolates identified above in Example I, 2c and the nucleic acid molecule encoding the BoNT/A receptor will be cloned using polymerase chain reaction (PCR) method. Genomic DNA from the C7 cell line will be isolated by an alkaline lysis procedure and will be amplified in PCR reactions using the ADVANTAGE® Genomic PCR kit (BD Biosciences Clontech, Palo Alto, Calif.) and the following two oligonucleotides 5'-AGCCCTCACTCCT-TCTCTAG-3' (SEQ ID NO: 29) and 5'-ACCTACAG-GTGGGGTCTTTC ATTCCC-3' (SEQ ID NO: 30). Reactions will be incubated at 95° C. for 1 minute, followed by 25 cycles at 68° C. for 30 seconds and 95° C. for 30 seconds, followed by 1 cycle at 68° C. for 6 minutes and final incubation at 4° C. The resulting PCR product will be purified from the PCR reaction by the QIAquick Gel Extraction Kit (QIAGEN, Inc., Valencia, Calif.), and will subjected to a second PCR amplification. The oligonucleotides used in the second PCR will be nested primers designed to anneal to sequences found within the PCR product originally purified, and will have the following nucleotide sequences: 5'-CCCTGGGTCAAGCCCTTTGTACACC-3' (SEQ ID NO: 31) and 5'-TGCCAAACCTACA GGTGGGGTCTTT-3' (SEQ ID NO: 32). The resulting nested DNA product will be subcloned into a pTOPO®-XL vector using the TOPO® TA cloning method (Invitrogen, Inc, Carlsbad, Calif.). The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 μg/mL of Ampicillin, and will be placed in a 37° C. incubator for overnight growth. Ampicillin-resistant colonies will be analyzed using an alkaline lysis plasmid mini-preparation procedure and candidate receptor constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 μg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy will identified the sequence composition of the BoNT/A receptor contained in HIT-T15 C7 isolate.

Example II

Identification of a BoNT/A Receptor Using a Cross-linking Procedure

1. Identification of Cell Lines with High Affinity Uptake for BoNT/A

Distinct sensitivities to each of the BoNT serotypes might be expected based on the individual receptor systems for each different toxin serotype and their differing expression in different cell lines. The presence of a high affinity receptor system in a cell for BoNT can be characterized by two attributes: a rapid uptake of the neurotoxin by the cell, and a low neurotoxin concentration needed for cell intoxication. To identify a cell line having a high affinity receptor system for a BoNT/A, we tested cell lines using one of two different in vitro cleavage assay, one to determine the amount of toxin required for intoxication, the other to determine the length of time necessary for the cell to uptake the neurotoxin.

1a. Assay to Determine the BoNT/A Concentration Necessary for Cell Intoxication

In order to assess the amount of BoNT/A needed to intoxicate a cell, a panel of mammalian cell lines of neuronal origin (see Table 3) was screened to determine whether toxin exposure would result in the cleavage of endogenously expressed SNAP-25. A suitable seed density of cells from each line was plated into individual wells of 6-well, poly-D-lysine/Laminin coated, tissue culture plates containing 3 mL of a suitable medium (see Table 3), and grown in a 37° C. incubator under 5% carbon dioxide for approximately 24 hours. BoNT/A (Metabiologics, Inc., Madison, Wis.) was added at different concentrations (0 nM, 1 nM, 5 nM, 12.5 nM, 25 nM, 50 nM) in the culture medium containing the cells for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl)piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 8A:
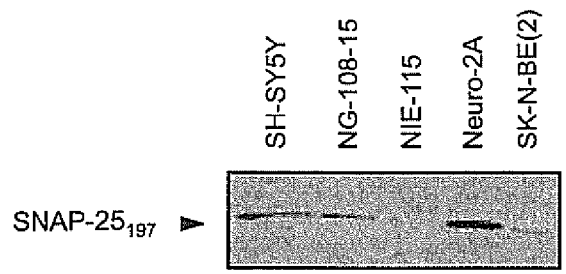
FIG. 8a shows a Western blot analysis used to identify cells capable of BoNT/A uptake. The blot shows five cell lines treated with 1 nM of PURE-A overnight, with equal amounts of protein loaded per lane and probed with an antibody that detects the BoNT/A SNAP-25197 cleavage product.

The presence of a BoNT/A SNAP25$_{197}$-cleavage product was determined by Western blot analysis as described above in Example I, 1b. A BoNT/A SNAP25$_{197}$-cleavage product was detected in the cell lines SH-SY5Y, NG108-15, N1E-115, Neuro-2A and SK-N-BE(2) after at least an 8 hour incubation with at least 5 nM BoNT/A, thereby indicating the ability of BoNT/A to intoxicate these cell lines (see FIG. 8a).

Figure 8B:
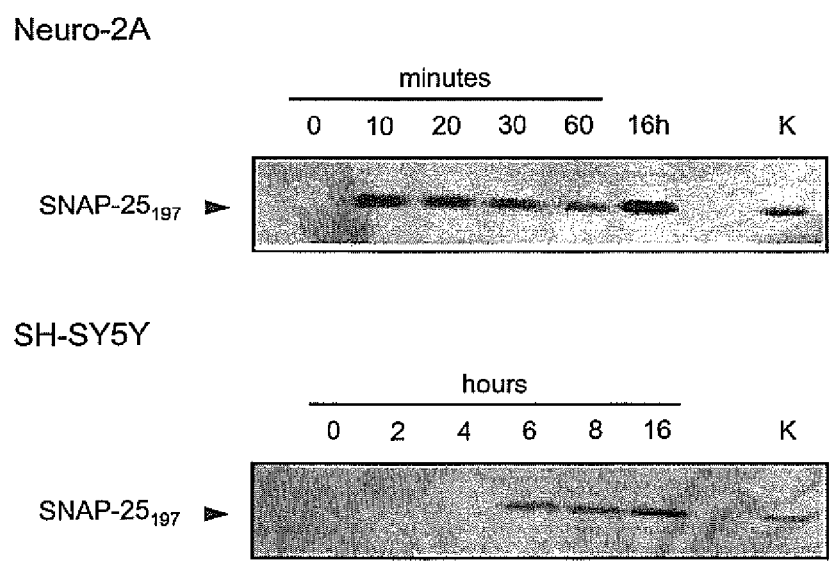
FIG. 8b shows Western blot analysis used to evaluate the time necessary for BoNT/A uptake. The blots show either Neuro-2A cells or SH-SY5Y cells treated with 1 nM of PURE-A for various lengths of time, with equal amounts of protein loaded per lane and probed with an antibody that detects the BoNT/A SNAP-25$_{197}$ cleavage product.
Figure 8C:
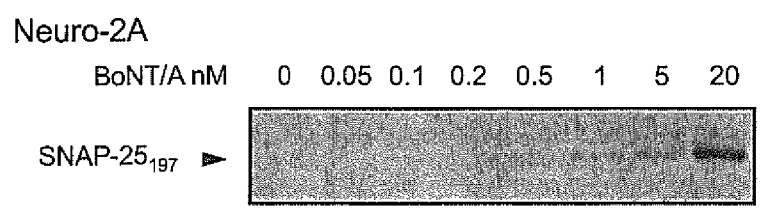
FIG. 8c shows a Western blot analysis used to evaluate the concentration range necessary of BoNT/A uptake. The blots show Neuro-2A cells treated with a range of PURE-A concentrations overnight, with equal amounts of protein loaded per lane and probed with an antibody that detects the BoNT/A SNAP-25$_{197}$ cleavage product.

The mouse neuroblastoma cell line Neuro-2A was further analyzed with lower concentrations of BoNT/A to determine the concentration of neurotoxin necessary to cleave endogenously expressed SNAP-25. Cells were grown in poly-D-lysine/Laminin coated 6-well plates as described above in Example II, 1a. BoNT/A (Metabiologics, Inc., Madison, Wis.) was added at different concentrations (0 nM, 0.05 nM, 0.1 nM, 0.2 nM, 0.5 nM, 1 nM, 5 nM and 20 nM) in the culture medium containing cells for either approximately 8 or approximately 16 hours. Toxin treated cells were harvested and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell line Neuro-2A after at least a 8 hour incubation with at least 0.5 nM BoNT/A, thereby indicating the ability of BoNT/A to intoxicate these cell lines (see FIG. 8c).

1b. Assay to Determine the Time Required by a Cell to Uptake BoNT/A

In order to assess the amount of time needed by a cell line to uptake BoNT/A, a panel of mammalian cell lines of neuronal origin was screened to determine the length of toxin exposure necessary to cleave endogenously expressed SNAP-25. Cells from each line were grown in poly-D-lysine/Laminin coated 6-well plates as described above in Example II, 1a. Approximately 1 nM BoNT/A (Metabiologics, Inc., Madison, Wis.) was added to the culture medium for 10 min, 20 min, 30 min, 60 min 2 hours, 4 hours, 6 hours, 8 hours or 16 hours. Toxin treated cells were collected and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell lines Neuro-2A, SH-SY5Y, and NG108-15 after at least an 8 hour incubation with 1 nM BoNT/A, thereby indicating the ability of these cell lines to rapidly uptake BoNT/A (see FIG. 8b).

were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration. The presence of a BoNT/A SNAP25$_{197}$-cleavage product was determined by

TABLE 3

Culture Conditions for Cell Lines

| Cell Line | Complete Culture Media | Passage Conditions | Seed Density (cells/mm$^2$) |
|---|---|---|---|
| SK-N-DZ | 90% DMEM, A | Trypsin/EDTA treatment, 1:4 dilution split every 2-3 day | $4.25 \times 10^3$ |
| SK-N-F1 | 90% DMEM, A | Trypsin/EDTA treatment, 1:4 dilution spilt twice a week | $4.25 \times 10^3$ |
| SK-N-SH | Ham's F12, DMEM or EMEM, B | Trypsin/EDTA treatment, 1:20 dilution split every 4-7 day | $4.25 \times 10^3$ |
| SH-SY5Y | EMEM and Ham's F12 1:1, C | Trypsin/EDTA treatment, 1:6 dilution split every 2-3 day | $4.25 \times 10^3$ |
| SK-N-BE(2) | EMEM and Ham's F12 1:1, D | Trypsin/EDTA treatment, 1:6 dilution split every 3 day | $4.25 \times 10^3$ |
| BE(2)-C | EMEM and Ham's F12 1:1, D | Trypsin/EDTA treatment, 1:4 dilution split every 2-3 day | $4.25 \times 10^3$ |
| BE(2)-M17 | EMEM and Ham's F12 1:1, D | Trypsin/EDTA treatment, 1:20 dilution split every 4-7 day | $4.25 \times 10^3$ |
| Neuro 2a | EMEM, E | Trypsin/EDTA treatment, 1:3 dilution split every 3 day | $4.25 \times 10^3$ |
| C1300 | RPMI 1640, B | Trypsin/EDTA treatment, 1:3 dilution split every 3 day | $4.25 \times 10^3$ |
| NB4 1A3 | Ham's F10, F | Trypsin/EDTA treatment, 1:3 dilution split every 3 day | $4.25 \times 10^3$ |
| N1E-115 | DMEM, G | Trypsin/EDTA treatment, 1:3 dilution split every 3 day | $4.25 \times 10^3$ |
| NG108-15 | DMEM, B | 1:4 dilution split every 1-2 days | $4.25 \times 10^3$ |
| HCN-1A | DMEM, H | Trypsin/EDTA treatment, 1:3 dilution split every 3 day | $4.25 \times 10^3$ |
| HCN-2 | DMEM, H | Trypsin/EDTA treatment, 1:3 dilution split every 3 day | $4.25 \times 10^3$ |
| TE 189.T | DMEM, H | Trypsin/EDTA treatment, 1:3 dilution split every 3 day | $4.25 \times 10^3$ |
| ND8/34 | DMEM, B | Trypsin/EDTA treatment, 1:3 dilution split every 3 day | $4.25 \times 10^3$ |

Figure 9A:
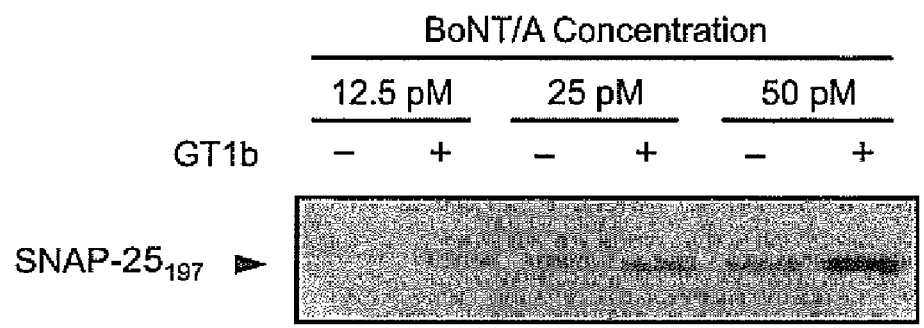
FIG. 9a shows a Western blot analysis evaluating the effects of ganglioside treatment on the uptake of BoNT/A. The blot shows Neuro-2A cells treated without or with 25 μg/mL of GT1b (– or +) and exposed overnight to three different concentrations of BoNT/A (12.5 pM, 25 pM or 50 pM), with equal amounts of protein loaded per lane and probed with an antibody that detects the BoNT/A SNAP-25$_{197}$ cleavage product.

A contains 1.5 g/L sodium bicarbonate, 0.1 mM Non-essential amino acids (NEAA), 4 mM Glutamine & 10% Fetal Calf serum (FCS)
B contains 2 mM Glutamine & 10% FCS
C contains 1.5 g/L sodium bicarbonate, 0.1 mM NEAA, 4 mM Glutamine, 1% sodium pyruvate, 1% penicillin/streptomycin (P/S) & 10% FCS
D contains 0.1 mM NEAA, 4 mM Glutamine, & 10% FCS
E contains 1.5 g/L sodium bicarbonate, 0.1 mM NEAA, 2 mM Glutamine, 1 mM sodium pyruvate & 10% FCS
F contains 2 mM Glutamine, 15% Horse Serum & 2.5% FCS
G contains 4.5 g/L glucose & 10% FCS
H contains 4 mM glucose & 10% FCS
Freeze medium comprises 95% culture medium and 5% DMSO 1c. Ganglioside Treatment to Increase High Affinity Uptake of BoNT/A by a Cell In order to assess the effect of ganglioside treatment on the ability of BoNT/A to intoxicate a cell, a Neuro-2A cell line was pre-treated with different gangliosides to determine whether these sugar moieties could increase the uptake of BoNT/A by these cells. Neuro-2A cells were plated at a suitable density into individual wells of 6-well, poly-D-lysine/Laminin coated, tissue culture plates containing 3 mL of a suitable medium (see Table 3), and grown in a 37° C. incubator under 5% carbon dioxide. After approximately 24 hours, the medium was replaced by a serum-free media and 25 μg/mL of one of the following gangliosides was added to individual wells: GD1a, GD1b, GD3, GQ1b, or GT1b (AXXORA, LLC, San Diego, Calif.). After an overnight 37° C. incubation period, the ganglioside-treated cells were washed three times with 1 ml of phosphate-buffered saline, pH 7.4 and then incubated at 37° C. with 1% serum media containing different concentrations (0 nM, 12.5 nM, 25 nM, 50 nM) of BoNT/A (Metabiologics, Inc., Madison, Wis.) for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl)piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells Western blot analysis as described above in Example II, 1a. An increase in BoNT/A SNAP25$_{197}$-cleavage product was detected in the Neuro-2A cell line treated with the ganglioside GT1b, thereby indicating that GT1b-treatment can increase the uptake of BoNT/A by Neuro-2A cells (see FIG. 9a).

1d. Ganglioside Treatment to Increase High Affinity Uptake of BoNT/E by a Cell

Figure 9B:
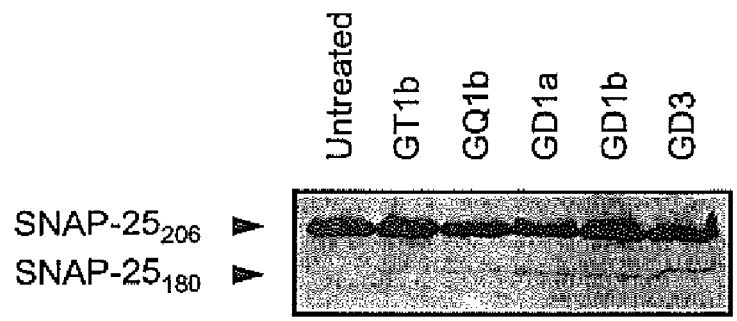
FIG. 9b shows a Western blot analysis evaluating the effects of ganglioside treatment on the uptake of BoNT/E. The blot shows Neuro-2A cells treated with either 25 μg/mL of GT1b, GQ1b, GD1a, GD1b or GD3 and exposed for approximately 5 hours to 14 nM of BoNT/E di-chain, with equal amounts of protein loaded per lane and probed with an antibody (SMI-81; Sternberger Monoclonals, Lutherville, Md.) that detects the uncleaved SNAP-25$_{206}$ substrate and the BoNT/E SNAP-25$_{180}$ cleavage product.

In order to assess the effect of ganglioside treatment on the ability of BoNT/E to intoxicate a cell, a Neuro-2A cell line was pre-treated with different gangliosides to determine whether these sugar moieties could increase the uptake of BoNT/E by these cells. Neuro-2A cells were grown in poly-D-lysine/Laminin coated 6-well plates and treated with gangliosides as described above in Example II, 1c. The ganglioside-treated cells were incubated with BoNT/E (Metabiologics, Inc., Madison, Wis.) at different concentrations (0 nM, 12.5 nM, 25 nM, 50 nM) in 1% serum media for either approximately 6 or approximately 16 hours. Toxin treated cells were harvested and lysed as described above in Example II, 1c. The presence of a BoNT/E SNAP25$_{180}$-cleavage product was determined by Western blot analysis as described above in Example I, 1b, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/E SNAP25$_{180}$-cleavage product. An increase in BoNT/E SNAP25$_{180}$-cleavage product was detected in the Neuro-2A cell lines treated with the gangliosides GD3, GD1b and GD1a, thereby indicating that GD3-treatment, GD1b-treatment or GD1a-treatment can increase the uptake of BoNT/E by Neuro-2A cells (see FIG. 9b).

2. Isolation of BoNT/A Receptor from Neuro-2A Cells

Neuro-2A cells were chosen to conduct ligand cross-linking experiments using BoNT/A since these cells had a rapid toxin uptake profile (about 10 minutes) and high affinity for BoNT/A. The trifunctional sulfo-SBED (Pierce Biotechnology, Inc., Rockford, Ill.) were used. The reagent sulfo-SBED contains three reactive groups (one of them designed to be UV-activated) and is designed to biotinylate a target protein.

To conjugate a cross-linking agent to a BoNT/A, approximately 100 μg of Pure A is centrifuged at 10,000×g at 4° C. for 10 minutes to pellet the toxin and brought up in a final volume of 900 μL of phosphate-buffered saline (pH 7.4). The solution is then transferred to the dark and 900 μL of 0.25 mM SBED, 1% DMSO solution is added and incubated in a 4° C. for two hours in a secondary container on shaking apparatus. The reaction is stopped by adding 50 μL of 1M TRIS (pH 7.4). The solution is inverted 6 times and incubated on ice for 30 minutes. The resulting PURE-A-SBED solution was used to conduct cross-linking experiments to identify a BoNT/A receptor.

To cross-link PURE-A to BoNT/A receptors present on Neuro-2A cells, about 1.5×10$^5$ Neuro-2A cells were plated in a 35 mm tissue culture dish containing 3 mL of complete EMEM, supplemented with 10% FBS, 2 mM glutamine (Invitrogen, Inc, Carlsbad, Calif.), 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached a density of about 5×10$^5$ cells/ml. The Neuro-2A cells were harvested by detaching the cells with a trypsin treatment, transferring the cells to 15 ml tubes, and centrifuging the cells at 5,000×g at 4° C. for 10 min. The cell pellet is washed three times with 9 mL of Tris-buffered saline, and then divided into aliquots of 4×10$^5$ cells. Each aliquot of cells is suspended in 12 mL cold Tris-buffered saline for a final density of 2×10$^7$ cells/mL, and placed on ice for 15 minutes. To one aliquot of cell suspension, 1 mL of PURE-A-SBED is added, final concentration is approximately 100 ug PURE A (33 nM). To a second cell aliquot, sulfo-SBED only is added and serves as a control for false positives. Both Neuro-2 cell suspensions were incubated at 4° C. for two hours in a secondary container using a shaking apparatus and then each cell solution is distributed in 13 aliquots of 1.0 mL. These aliquots were exposed to ultraviolet radiation (365 nm) at 4° C. for 15 minutes.

The cells were centrifugation at 5,000×g at 4° C. for 15 minutes and washed once with 1 mL cold Tris-buffered saline. Washed cells were lysed in 0.5 ml of lysis buffer containing 50 mM N-(2-hydroxyethyl)piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol, 1% (v/v) Triton-X® 100 (4-octylphenol polyethoxylate) and suitable protease inhibitors, with rotation overnight at 4° C. Lysed cells were centrifuged at 5,000 rpm at 4° C. for 10 min to eliminate debris, the supernatants were transferred to fresh siliconized tubes and 0.05 mL of avidin-beads were added to the cleared supernatants. This mixture was incubated at 4° C. for 3 hours. The avidin beads were then washed twice by centrifuging at 1000×g at 4° C. for 10 min to pellet beads, decanting the supernatant, adding 0.5 mL lysis buffer and incubating the solution at 4° C. for 10 minutes. The avidin beads were then washed twice with 0.5 mL phosphate-buffered saline (pH 7.4). Approximately 100 μL of SDS-PAGE loading buffer was added to the washed, pelleted avidin beads and boiled for 10 minutes. A 40 μL aliquot was then subjected to MOPS polyacrylamide gel electrophoresis using NuPAGE® Novex 4-12% Bis-Tris precast polyacrylamide gels (Invitrogen, Inc, Carlsbad, Calif.) under non-denaturing and denaturing, reducing conditions. FIG. 10a shows an approximately 250 kDa protein in non-reducing gels which represents the intact cross-linking reagent PURE-A-SBED toxin bound to the putative BoNT/A receptor. Same samples run under denaturing conditions and reveals an approximately 100 kDa protein was co-purified with PURE-A-SBED.

To determine the identity of the BoNT/A receptor isolated from the cross-linking experiments, western blot analysis was performed using antibodies to the cytoplasmic region of the polypeptides FGF 1 receptor (FGFR1), FGF 2 receptor (FGFR2), FGF 3 receptor (FGFR3) and FGF 4 receptor (FGFR4). Approximately 40 μL aliquots of the precipitated receptor-PureA complex, obtained as described above in Example II, 2, were separated by MOPS polyacrylamide gel electrophoresis using NuPAGE® Novex 4-12% Bis-Tris precast polyacrylamide gels (Invitrogen, Inc, Carlsbad, Calif.) under non-reducing and denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20®, polyoxyethylene (20) sorbitan monolaureate) containing one of the following primary antibody solutions: 1) a 1:1000 dilution of rabbit polyclonal anti-FGFR1 antiserum (Santa Cruz Biotechnologies, Inc., Santa Cruz, Calif.); 2) a 1:1000 dilution of goat polyclonal anti-FGFR2 antiserum (Santa Cruz Biotechnologies, Inc., Santa Cruz, Calif.); 3) a 1:1000 dilution of rabbit polyclonal anti-FGFR3 (C15) antiserum (Santa Cruz Biotechnologies, Inc., Santa Cruz, Calif.); or 4) a 1:1000 dilution of goat polyclonal anti-FGFR4 antiserum (Santa Cruz Biotechnologies, Inc., Santa Cruz, Calif.). Primary antibody probed blots were washed three times for 15 minutes each time in Tris-Buffered Saline TWEEN-20®. Washed membranes were incubated at room temperature for 2 hours in Tris-Buffered Saline TWEEN-20® containing either a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody for the FGFR1 and FGFR3 blots or a 1:20,000 dilution of rabbit polyclonal anti-goat immunoglobulin G, heavy and light chains (IgG, H+L) antibody conjugated to horseradish peroxidase (HRP; Pierce Biotechnology, Inc., Rockford, Ill.) for the FGFR2 and FGFR4 blots. Secondary antibody-probed blots were washed three times for 15 minutes each time in Tris-Buffered Saline TWEEN-200. Signal detection of the labeled BoNT/A SNAP25$_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A band was detected in toxin-receptor sample probed with anti-FGFR3 antiserum of approximately 97 kDa that is consistent with the size of FGFR3, indicating that FGFR3 is a BoNT/A receptor (see FIG. 10b).

3. Identification of BoNT/A Receptor from Various Cells

Several cells lines responsive to BoNT/A uptake were probed with antibodies raised against FGFR1, FGFR2, FGFR3 and FGFR4 in order to determine which FGFRs these cell lines express. In addition, cells from the BoNT/A unresponsive HIT-T15 wild-type cell line and the BoNT/A responsive HIT-T15 isolate C7 cell line, as described above in Example I, 2c and 2d, were examined.

Figure 11:
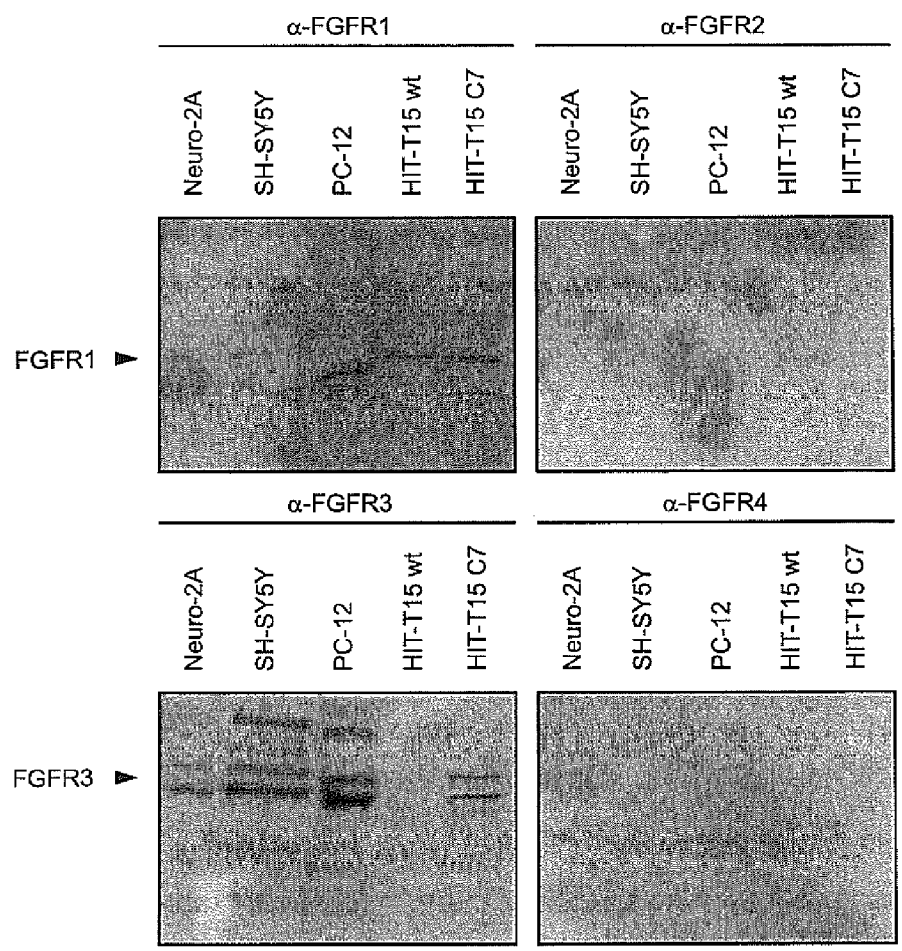
FIG. 11 shows a Western blot analysis used to determine the presence of FGFRs in five different cell lines. Only antibodies selectively binding to FGFR3 detected bands that correlated with cell lines that contained a BoNT/A receptor.

To determine the presence of FGFRs in cell lines responsive to BoNT/A exposure, cells were grown, harvested and lysed as described above in Example II, 1a, 1b or 2c and 40 µL aliquots were subjected to Western blot analysis as described above in Example II, 2. These results indicate that the BoNT/A responsive cell lines Neuro-2A, SH-SY5Y and HIT-T15-C7 all express FGFR3, while the BoNT/A unresponsive wild-type HIT-T15 does not (see FIG. 11). The data also from the revealed that FGFR2 and FGFR4 were not detected in any of the cell lines tested, while FGFR1 was present in all cell lines tested, including wild-type HIT-T15 cells that are unresponsive to BoNT/A exposure (see FIG. 11).

4. Competitive Competition Assays

To corroborate that BoNT/A toxin enters Neuro-2A cells through the FGFR3 we performed a competition experiment with PURE-A and analyzed the responsiveness of tested using the SNAP-25 cleavage assay, as described above in Example I, 1b. If BoNT/A and an FGFR3 ligand bind to the same receptor, then increasing amounts of FGF ligand should result in decreased responsiveness of a cell to BoNT/A exposure. However, if BoNT/A and an FGFR3 ligand bind to the different receptors, then increasing amounts of FGF ligand should have no effect of the responsiveness of a cell to BoNT/A exposure. Table 1, which Applicants do not claim is a complete tabulation of FGF receptors and species, shows certain members of the family of FGFRs and their known ligands and tissue distribution.

To determine whether ligands for FGFR3 can competitively compete with BoNT/A for binding to FGFR3, about 5×10$^5$ Neuro-2A cells were plated in individual wells of a 6-well, poly-D-lysine/Laminin coated, tissue culture plates containing 3 mL of EMEM, supplemented with 2 mM glutamine (Invitrogen, Inc, Carlsbad, Calif.), 1 mM sodium pyruvate (Invitrogen, Inc, Carlsbad, Calif.), 1.5 g/L sodium bicarbonate and 1× MEM non-essential amino acids solution (Invitrogen, Inc, Carlsbad, Calif.), and grown in a 37° C. incubator under 5% carbon dioxide until the cells reached confluency. Approximately 5 nM PURE-A (Metabiologics, Inc., Madison, Wis.) was added in conjunction with FGF1, FGF2 or both FGF1 and FGF2 at different concentrations (0 nM, 0.1 nM, 1 nM, 5 nM, 50 nM, 200 nM) in the culture medium containing the cells and incubated for at 37° C. for approximately 10 minutes Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1× SDS sample buffer at 1 mg/ml or higher concentration.

Figure 12:
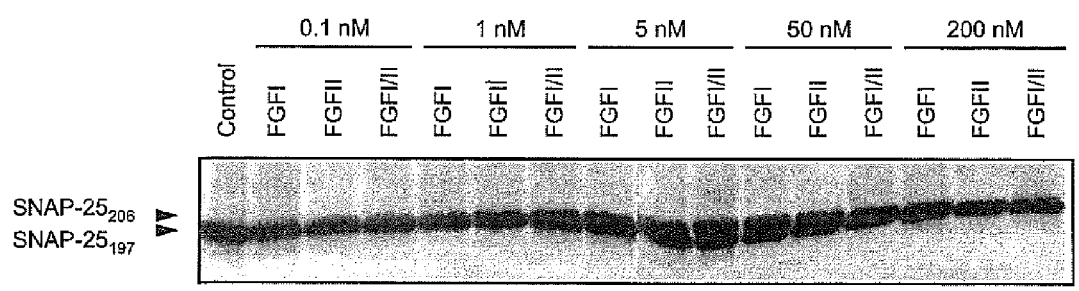
FIG. 12 shows the results of a receptor competition experiment in Neuro-2a cells using PURE-A and FGF ligands. A western blot analysis shows that both FGF1 and FGF2 effectively competed with BoNT/A for binding to the BoNT/A receptor, with equal amounts of protein loaded per lane and probed with antibody (SMI-81; Sternberger Monoclonals, Lutherville, Md.) that detects the uncleaved SNAP-25$_{206}$ substrate and the BoNT/E SNAP-25$_{180}$ cleavage product. The appearance of the uncleaved SNAP-25$_{206}$ substrate was detected when as little as 1 nM of FGF ligand was present and clearly visible when 5 nM of FGF ligands were present. Detectable levels of the BoNT/A SNAP-25$_{197}$ cleavage product was absent in FGF ligand treatments of 200 mM.

The presence of a BoNT/A SNAP25$_{197}$-cleavage product was determined by Western blot analysis as described above in Example II, 1a, with the exception that blocked PVDF membranes will be incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect both the uncleaved SNAP-25 substrate and BoNT/A SNAP25$_{197}$-cleavage product. An increasing amount an increasing amount of FGF ligands, indicating these FGF1 and FGF2 compete for the same receptor as BoNT/A and further confirming that FGFR3 is a BoNT/A receptor (see FIG. 12).

Example III

A fusion protein comprising the C terminal portion of the heavy chain of BoNT/A and the light chain of BoNT/E is tested for its ability to selectively bind and intoxicate BoNT/A susceptible cells. A preparation comprising dilutions of the fusion protein is incubated with HIT-T15 insulinoma cells expressing exogenous FGFR3 in the presence of GT1b ganglioside. The ability of the fusion peptide to bind and enter the insulinoma cells is detected by detecting secretion of insulin in response to the presence of glucose, as described above in Example I, 1a. By contrast, insulin secretion is unaffected in cells not expressing FGFR3.

The results of this assay show that amount of insulin secreted into the culture medium is decreased in a dose-dependent manner when the fusion protein is added to the culture medium. Western blots of cell lysates will show the conversion of full length SNAP-25 to the cleaved form typical of the proteolytic activity of the BoNT/E light chain protease. This assay therefore is useful in showing that the fusion peptide is able to bind and enter BoNT/A susceptible cells.

The same fusion protein is capable of intoxicating cells of the neuromuscular junction.

Example IV

A fusion protein comprising the receptor binding portion of an FGF species capable of binding FGFR3 (including FGF1, FGF2, FGF4 and FGF9) and the translocation domain and light chain of BoNT/E is tested for its ability to selectively bind and intoxicate BoNT/A susceptible cells. The assay is conducted as described in Example 1 above, with similar results; the detected cleaved SNAP-25 fragments are characteristic of BoNT/A intoxication.

Example V

BoNT/A, produced from fermentation of *Clostridium botulinum* is produced using standard fermentation techniques. Either or both the bulk preparation and purified, formulated versions of expressed toxin are tested for purity and activity as follows. A preparation comprising dilutions of the BoNT/A preparation is incubated with HIT-T15 insulinoma cells expressing exogenous FGFR3 in the presence of GT1b ganglioside. The ability of the toxin to bind and enter the insulinoma cells is detected by detecting secretion of insulin in response to the presence of glucose, as described above in Example I, 1a. The specific activity of the preparation can be calculated from the determined protein concentration and the activity of the preparation at various doses.

These data are submitted to the U.S. Food and Drug Administration by a pharmaceutical company as part of data demonstrating how BoNT/A is manufactured and tested. This information is considered by the FDA, who decides to permit the manufacture and sale of this lot of BoNT/A, and subsequent lots made and tested in a similar manner, as a therapeutic pharmaceutical product based in part on this bulk and/or formulation assay data.

The pharmaceutical comprising the BoNT/A is then offered for sale as a prescription medication.

Example VI

Same as Example V, however the polypeptide produced is the fusion neurotoxin of Example III, produced in *E. coli*. Both bulk and/or formulation lots of the fusion neurotoxin are tested as indicated above, the data submitted to the FDA, and a decision to grant marketing approval, or continued sales of such fusion polypeptide as a therapeutic agent, is made by the FDA based at least in part on such data. The pharmaceutical company then offers the fusion neurotoxin for sale as a prescription therapeutic agent.

Example VII

An in vitro assay is established using cloned FGFR3 bound to a solid support in the presence of ganglioside GT1b. The bound FGFR3 is first saturated with BoNT/A heavy chain (H chain) in phosphate buffered saline (PBS), and washed free of unbound FGF. A test compound from a combinatorial library of compounds is contacted with the receptor under substantially physiological conditions (e.g., PBS), and the eluate collected. The H chain concentration in the eluate is compared to the H chain concentration of a control eluate in which H chain was not first bound to FGFR3.

Test compounds which are able to strongly bind FGFR3 and compete with H chain for FGFR3 binding (for example, by the method described in this section) are candidates compounds for the development of an antidote to acute botulism poisoning.

Example VIII

Generation of Cells Stably Containing a FGFR3

1. Construction of pQBI25/FGFR3

To construct pQBI-25/FGFR3, a nucleic acid fragment encoding the amino acid region comprising FGFR3 of SEQ ID NO: 4 is amplified from a human brain cDNA library using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/FGFR3 construct is digested with restriction enzymes that 1) excise the insert containing the entire open reading frame encoding the FGFR3; and 2) enable this insert to be operably-linked to a pQBI-25 vector (Qbiogene, Inc., Irvine, Calif.). This insert is subcloned using a T4 DNA ligase procedure into a pQBI-25 vector that is digested with appropriate restriction endonucleases to yield pQBI-25/FGFR3. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the FGFR3 of SEQ ID NO: 4 operably-linked to the expression elements of the pQBI-25 vector.

2. Stably Transformed Cells Using a Recombinant Crossing-Over Procedure

To generate a stably-integrated cell line expressing a FGFR3 using a crossing over procedure, a suitable density ($1 \times 10^5$ to $1 \times 10^{6^6}$ cells) of appropriate cells, such as, e.g., HIT-T15 or Neuro2A, are plated in a 35 mm tissue culture dish containing 3 mL of complete, supplemented culture media and grown in a 37° C. incubator under 5% carbon dioxide until the cells reached a density appropriate for transfection. A 500 µL transfection solution is prepared by adding 250 µL of OPTI-MEM Reduced Serum Medium containing 15 µL of LipofectAmine 2000 (Invitrogen, Carlsbad, Calif.) incubated at room temperature for 5 minutes to 250 µL of OPTI-MEM Reduced Serum Medium containing 5 µg of expression construct encoding a FGFR3, such as, e.g., pQBI-25/FGFR3 (see Examples VIII, 1). This transfection was incubated at room temperature for approximately 20 minutes. The complete, supplemented media is replaced with 2 mL of OPTI-MEM Reduced Serum Medium and the 500 µL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 µg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 µg/mL of G418 until these cells reached a density of 6 to $20 \times 10^5$ cells/mL.

To test for expression of a FGFR3 from isolated cell lines that stably-integrated an expression construct encoding a FGFR3, such as, e.g., pQBI-25/FGFR3 (see Examples VIII, 1), approximately $1.5 \times 10^5$ cells from each cell line are plated in a 35 mm tissue culture dish containing 3 mL of G418-selective, complete, supplemented DMEM and are grown in a 37° C. incubator under 5% carbon dioxide until cells reached a density of about 5×10⁵ cells/ml (6-16 hours). Media is replaced with 3 mL of fresh G418-selective, complete, supplemented culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of a FGFR3, samples are separated by MOPS polyacrylamide gel electrophoresis and analyzed by Western blotting procedures as described above in Example II, 2 using a 1:1000 dilution of rabbit polyclonal anti-FGFR3 (C15) antiserum (Santa Cruz Biotechnologies, Inc., Santa Cruz, Calif.), in order to identify cell lines that have stably integrated and express the FGFR3 substrate.

Example IX

FGFR3 Phosphorylation Studies

1. Phosphorylation of FGFR-3 Exposed to FGF or BoNT/A

When bound by specific ligands, FGFR's are auto-phosphorylated on specific tyrosine residues. This begins the process of internalization of both the receptor and the ligand into the endosomal pathway. If BoNT/A binds to FGFR3, then exposure to BoNT/A should cause the auto-phosphorylation of FGFR3 in exposed cells.

To determine whether BoNT/A binding resulted in FGFR3 phosphorylation, approximately 1.5×10⁵ Neuro-2A cells were plated into the wells of 6-well, poly-D-lysine/Laminin coated, tissue culture plates containing 3 mL of serum-free EMEM, supplemented with 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached a density of about 5×10⁵ cells/ml. The serum-free media was replaced with fresh supplemented EMEM containing 1% FBS (Invitrogen, Inc, Carlsbad, Calif.) and either 5 nM FGF-2 (Biosource International, Camarillo, Calif.) or 5 nM of PURE/A (Metabiologics, Inc., Madison, Wis.). The cells were then incubated in a 37° C. incubator under 5% carbon dioxide for approximately 5 min, 10 min, 20 min and 30 min, with unexposed cells used as time 0. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl)piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 13A:
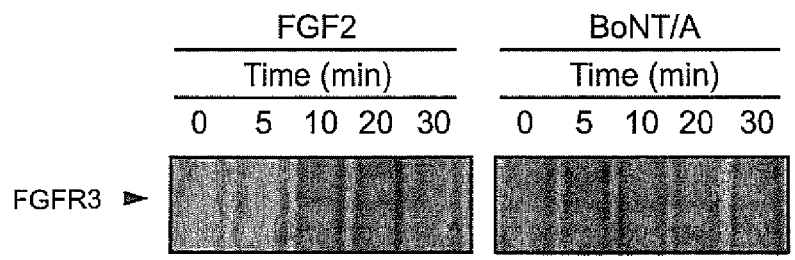
FIG. 13a shows a Western blot analysis indicating the presence of phosphorylated FGFR3 after exposure to FGF2 or BoNT/A. The blot shows Neuro-2A cells treated with either 5 nM FGF2 or 5 nM PURE-A for various lengths of time, with equal amounts of protein loaded per lane and probed with an antibody that detects FGFR3.

Supernatant containing 100 μg of protein was immunoprecipitated using 5 μg of anti-phosphotyrosine antibody attached to a sepharose bead (Zymed Laboratories, Inc., South San Francisco, Calif.). The immunoprecipitated product were subjected to Western blot analysis as described above in Example II, 4, with the blots being probed for FGFR3 (Santa Cruz Biotechnologies, Inc., Santa Cruz, Calif.). These experiments show that FGFR3 is phosphorylated upon either FGF2 or BoNT/A exposure, indicating that BoNT/A binds to FGFR3 (see FIG. 13a).

2. DMBI Inhibition of FGFR-3 Phosphorylation Exposed to FGF

Figure 13B:
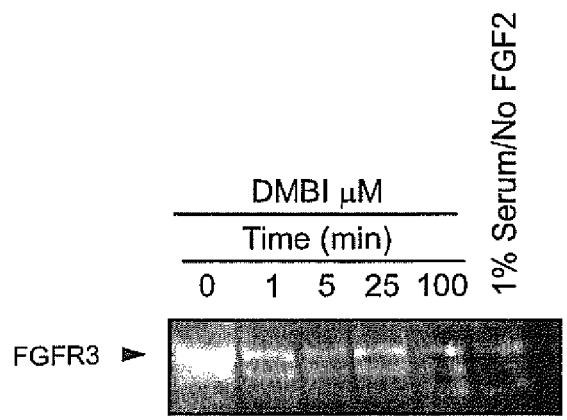
FIG. 13b shows a Western blot analysis indicating the reduction of phosphorylated FGFR3 when exposed to increasing amounts of DMBI. The blot shows Neuro-2A cells treated with 5 nM FGF2 for 10 minutes, with equal amounts of protein loaded per lane and probed with an antibody that detects phosphorylated FGFR3.

To determine whether DMBI inhibits BoNT/A-induced FGFR3 phosphorylation, Neuro-2A cells were plated and grown as described above in Example IX, 1. Neuro-2A cells were plated at a density of 5×10⁵ cells/well (6 well plate) and incubated overnight in serum-free media. The media was replaced with fresh serum-free supplemented EMEM containing 0, 1 μM, 5 μM, 20 μM, or 100 μM of DMBI (EMD Calbiochem, San Diego, Calif.) for 1 hour. DMBI inhibits the autophosphorylation and dimerization of FGFR and PDGF type receptors. The cells were then washed and fresh supplemented EMEM containing 1% FBS (Invitrogen, Inc, Carlsbad, Calif.) and 5 nM FGF-2 (Biosource International, Camarillo, Calif.). The cells were then incubated in a 37° C. incubator under 5% carbon dioxide for approximately 5 min, 10 min and harvested and immunoprecipitated as described above in Example IX, 1. The immunoprecipitated products were subjected to Western blot analysis as described above in Example II, 4, with the exception that the blots were probed with a primary antibody solution containing a 1:1000 dilution of a rabbit polyclonal anti-phosphotyrosine antiserum (Upstate USA, Inc., Charlottesville, Va.) and a secondary antibody solution containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.). These results indicate that DMBI effectively inhibits the phosphorylation of FGFR3 upon FGF2 exposure (see FIG. 13b).

3. DMBI Inhibition of BoNT/A Activity

Figure 13C:
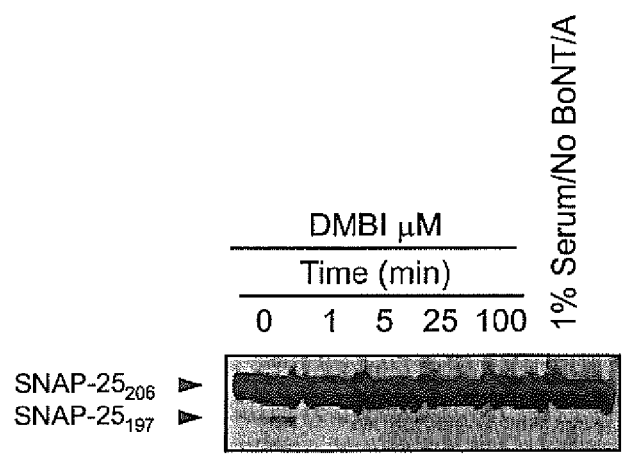
FIG. 13c shows a Western blot analysis indicating the reduction of SNAP-25$_{197}$ cleavage product when exposed to increasing amounts of DMBI. The blots show either Neuro-2A cells treated with 5 nM of PURE-A for 10 minutes, with equal amounts of protein loaded per lane and probed with an antibody that detects the BoNT/A SNAP-25$_{197}$ cleavage product.

To determine whether DMBI can inhibit BoNT/A activity, Neuro-2A cells were plated and grown as described above in Example IX, 1. The media was replaced with fresh serum-free supplemented EMEM containing 0, 1 μM, 5 μM, 20 μM, or 100 μM of DMBI (EMD Calbiochem, San Diego, Calif.) for 1 hour. DMBI inhibits the autophosphorylation and dimerization of FGFR and PDGF type receptors. The cells were then washed and fresh supplemented EMEM containing 1% FBS (Invitrogen, Inc, Carlsbad, Calif.) and 5 nM of PURE/A (Metabiologics, Inc., Madison, Wis.). The cells were then incubated in a 37° C. incubator under 5% carbon dioxide for approximately 5 min, 10 min and harvested as described above in Example IX, 1. Aliquots were tested for the presence of the BoNT/A SNAP-25₁₉₇ cleavage product using the SNAP-25 cleavage assay as described above in Example I, 1b. These results indicate a reduction in the amount of SNAP-25 cleavage product present, thereby indicating that DMBI effectively inhibits BoNT/A activity and confirming that this toxin in internalized by FGFR3 (see FIG. 13c).

Example X

SV2 Enhances BoNT/A Binding to FGFR3

To determine the role of SV2 in BoNT/A binding to FGFR3, the binding of BoNT/A to FGFR3, SV2 characterized using Surface plasmon resonance analysis. High affinity binding was observed between rBoNT/A-Hc and loop 2 and 3 of the extra cellular domain of FGFR3 (~25 nM). In comparison weak binding was observed with SV2C (250 nM). However, when SV2C was combined with sFGFR3 the binding of sFGFR3 to rBoNT/A-Hc was enhanced. In addition, a BIAcore chip surface covered with immobilized rBoNT/A-Hc could recover FGFR3 from cell membrane extracts. Moreover, cells over-expressing FGFR3 or FGFR3 and SV2C were more sensitive to BoNT/A uptake. Competition experiments demonstrated that sFGFR3 blocked BoNT/A uptake in Neuro-2a cells in a similar manner than an antibody to BoNT/A-Hc. Similarly, known ligands for FGFR3 like FGF1, FGF2 and FGF9, competed BoNT/A binding to neuronal cells, while FGF10, which is not a ligand for FGFR3, did not. Finally, we report that BoNT/A functions much like a natural agonist ligand for FGFR3, since treatment with BoNT/A leads to increased receptor phosphorylation comparable to treatment with native ligands. The data reported here supports a model where FGFR3 acts as a high affinity receptor for BoNT/A on the cell surface and suggests that SV2C may enhance or stabilize the interaction between FGFR3 and BoNT/A as part of a larger receptor complex in the membrane of neuronal cells.

The examples provided herein are simply illustrations of various aspects of the invention, which is to be understood to be defined solely by the claims which follow this specification.

What is claimed:

1. A method of detecting Botulinum toxin serotype A (BoNT/A) activity, the method comprising the steps of:
   a. contacting a sample to a cell that contains an exogenous Fibroblast Growth Factor Receptor 3(FGFR3), an exogenous synaptic vesicle glycoprotein 2(SV2), and a synaptosome-associated protein of 25000 Daltons (SNAP-25), wherein said cell is genetically engineered to express a nucleic acid molecule encoding said FGFR3 and a nucleic acid molecule encoding said SV2;
   wherein said cell is capable of BoNT/A intoxication; and
   b. detecting the presence of BoNT/A activity of said cell relative to a control cell, wherein the presence of SNAP-25 cleavage product from said cell is indicative of BoNT/A activity.

2. The method according to claim 1, wherein said SV2 is a SV2A, a SV2B, or a SV2C.

3. The method according to claim 1, wherein said SV2 SEQ ID NO: 33, SEQ ID NO: 34, SEQ ID NO: 35, or SEQ ID NO: 36.

4. The method according to claim 1, wherein said cell further contains a polysialoganglioside.

5. The method according to claim 4, wherein said polysialoganglioside is selected from the group consisting of GD1a, GD1b, GD3, GQ1b, or GT1b.

6. A method of detecting BoNT/A activity by, the method comprising the steps of:
   a. contacting a sample to a cell that contains FGFR3, an exogenous SV2, and a SNAP-25, wherein said cell is genetically engineered to express a nucleic acid molecule encoding said SV2; and
   wherein said cell is capable of BoNT/A intoxication and
   b. detecting the presence of BoNT/A activity of said cell relative to a control cell, wherein the presence of SNAP-25 cleavage product from said cell is indicative of BoNT/A activity.

7. The method according to claim 6, wherein said cell further contains a polysialoganglioside.

8. The method according to claim 7, wherein said polysialoganglioside is selected from the group consisting of GD1a, GD1b, GD3, GQ1b, or GT1b.

9. The method according to claim 1, wherein said exogenous FGFR3 is a mammalian FGFR3.

10. The method according to claim 9, wherein said mammalian FGFR3 is a human FGFR3, a bovine FGFR3, a mouse FGFR3, or a rat FGFR3.

11. The method according to claim 1, wherein said SNAP-25 is an exogenous SNAP-25 and said cell is genetically engineered to express a nucleic acid molecule encoding said exogenous SNAP-25.

12. The method according to claim 1, wherein said SNAP-25 is an endogenous SNAP-25.

13. The method according to claim 6, wherein said SV2 is a SV2A, a SV2B, or a SV2C.

14. The method according to claim 13, wherein said SV2 SEQ ID NO: 33, SEQ ID NO: 34, SEQ ID NO: 35, or SEQ ID NO: 36.

15. The method according to claim 6, wherein said FGFR3 is an exogenous FGFR3 and said cell is genetically engineered to express a nucleic acid molecule encoding said exogenous FGFR3.

16. The method according to claim 6, wherein said FGFR3 is a mammalian FGFR3.

17. The method according to claim 16, wherein said mammalian FGFR3 is a human FGFR3, a bovine FGFR3, a mouse FGFR3, or a rat FGFR3.

18. The method according to claim 6, wherein said FGFR3 is an endogenous FGFR3.

19. The method according to claim 6, wherein said SNAP-25 is an exogenous SNAP-25 and said cell is genetically engineered to express a nucleic acid molecule encoding said exogenous SNAP-25.

20. The method according to claim 6, wherein said SNAP-25 is an endogenous SNAP-25.

* * * * *

UNITED STATES PATENT AND TRADEMARK OFFICE
CERTIFICATE OF CORRECTION

PATENT NO.         : 7,645,570 B2
APPLICATION NO. : 12/047441
DATED                   : January 12, 2010
INVENTOR(S)        : Ester Fernandez-Salas et al.

It is certified that error appears in the above-identified patent and that said Letters Patent is hereby corrected as shown below:

Title Page; item (56);
On the face page, in column 2, under "U.S. Patent Documents", line 12, delete "424/" and insert -- 424/236.1 --, therefor.

On the face page, in column 2, under "U.S. Patent Documents", line 15, after "424/239.1" delete "236.1".

In column 1, line 19, delete "botulinum toxin" and insert -- Botulinum Toxin --, therefor.

In column 1, line 40, delete "Botulinum toxin" and insert -- Botulinum Toxin --, therefor.

In column 1, line 47, delete "botulinum toxin" and insert -- Botulinum Toxin --, therefor.

In column 2, line 19, delete "endocytosised" and insert -- endocytosed --, therefor.

In column 9, line 56, delete "Igilic" and insert -- IgIIIc --, therefor.

In column 22, line 44, delete "gramacidine" and insert -- gramicidin --, therefor.

In column 22, line 45, delete "TAT," and insert -- TAT., --, therefor.

In column 25, line 43, delete "polybiquitin" and insert -- polyubiquitin --, therefor.

In column 26, line 50, delete "hemagluttinin" and insert -- hemagglutinin --, therefor.

In column 27, line 3, delete "Manual" and insert -- Manual: --, therefor.

In column 27, line 62, before "example," delete "limiting". (Repeated Word)

In column 35, line 49, before "methods" delete "limiting". (Repeated Word)

In column 38, line 58, delete "20 ed. 2000);" and insert -- 20th ed. 2000); --, therefor.

In column 50, line 42, after "BoNT/A" insert -- . --.

In column 52, line 35, delete "TWEEN-200," and insert -- TWEEN-20®, --, therefor.

In column 52, line 47, delete "TWEEN-200," and insert -- TWEEN-20®, --, therefor.

CERTIFICATE OF CORRECTION (continued)
U.S. Pat. No. 7,645,570 B2

In column 52, line 49, delete "TWEEN-200," and insert -- TWEEN-20®, --, therefor.

In column 61, line 2, delete "TWEEN-200," and insert -- TWEEN-20®, --, therefor.

Signed and Sealed this

Twentieth Day of April, 2010

David J. Kappos
*Director of the United States Patent and Trademark Office*